(12) United States Patent
Mayweg et al.

(10) Patent No.: US 7,579,369 B2
(45) Date of Patent: Aug. 25, 2009

(54) CB 1 RECEPTOR INVERSE AGONISTS

(75) Inventors: Alexander Mayweg, Loerrach (DE);
 Hans Peter Marty, Basel (CH); Werner Mueller, Aesch (CH); Robert Narquizian, St. Louis (FR); Werner Neidhart, Hagenthal le Bas (FR); Philippe Pflieger, Schwoben (FR); Stephan Roever, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 84 days.

(21) Appl. No.: 11/801,727

(22) Filed: May 10, 2007

(65) Prior Publication Data

US 2007/0238754 A1    Oct. 11, 2007

Related U.S. Application Data

(62) Division of application No. 10/743,642, filed on Dec. 22, 2003, now Pat. No. 7,294,644.

(51) Int. Cl.
  *A61K 31/40* (2006.01)
  *C07D 233/64* (2006.01)
(52) U.S. Cl. ............. 514/400; 514/423; 548/333.5; 548/537
(58) Field of Classification Search ............ None
  See application file for complete search history.

(56) References Cited

U.S. PATENT DOCUMENTS

| | | | |
|---|---|---|---|
| 3,940,418 | A | 2/1976 | Hamilton |
| 5,596,106 | A | 1/1997 | Cullinan et al. |
| 5,624,941 | A | 4/1997 | Barth et al. |
| 6,613,789 | B2 | 9/2003 | Khanna et al. |
| 7,135,488 | B2 | 11/2006 | Guba et al. |

FOREIGN PATENT DOCUMENTS

| | | |
|---|---|---|
| EP | 576357 | 12/1993 |
| EP | 656354 | 6/1995 |
| EP | 658546 | 6/1995 |
| JP | 2006-513226 | 4/2006 |
| WO | WO9602248 | 2/1996 |
| WO | WO9719063 | 5/1997 |
| WO | WO0115609 | 3/2000 |
| WO | WO0046209 | 8/2000 |
| WO | WO0132663 | 5/2001 |
| WO | WO0164632 | 9/2001 |
| WO | WO0164633 | 9/2001 |
| WO | WO0164634 | 9/2001 |
| WO | WO0170700 | 9/2001 |
| WO | WO0228346 | 4/2002 |
| WO | WO 03/007887 A2 | 1/2003 |
| WO | WO 03/007887 A3 | 1/2003 |
| WO | WO 03/027069 | 4/2003 |
| WO | WO 03/027076 A2 | 4/2003 |
| WO | WO 03/027076 A3 | 4/2003 |
| WO | WO 03/027114 | 4/2003 |
| WO | WO 03/040107 | 5/2003 |

OTHER PUBLICATIONS

Pacheco, M., et al., Aminoalkylindoles: Actions on Specific G-Protein-Linked Receptors, Journal of Pharmacology and Experimental Therapeutics, 1991, pp. 170-183, v.257(1).
Casiano, F.M., et al., Putative Aminoalkylindoles (AAI) Antagonists, Problems of Drug Dependence 1990: Proceedings of the 52nd Annual Scientific Meeting The Committeee on Problems of Drug Dependence, 1991, pp. 295-296, v. 105.
Hosohata, K., et al., AM630 is a Competitive Cannabinoid Receptor Anatagonist in the Guinea Pig Brain, Life Sciences, 1997, pp. 115-118, v. 61(9).
Pertwee, R., et al., AM630, A Competitive Cannabinoid Receptor Antagonist, Life Sciences, 1995, pp. 1949-1955, v. 56(23/24).
Felder, C.C., et al., LY320135, a Novel Cannabinoid CB1 Receptor Antagonist, Unmasks Coupling of the CB1 Receptor to Stimulation of cAMP Accumulation, Journal of Pharmacology and Experimental Therapeutics, 1998, pp. 291-297, v. 284(1).
Kanyonyo, M. et al., 3-Alkyl-(5,5'-Diphenyl) Imidazolidinediones As New Cannabinoid Ligands, Bioorganic & Medicinal Chemistry Letters, 1999, pp. 2233-2236, v. 9.
Ooms, F., et al., Exploration of the Pharmacophore of 3-Alkyl-5-Arylimidazolidinediones as New $CB_1$ Cannabinoid Receptor Ligands and Potential Antagonists: Synthesis, Lipophilicity, Affinity, and Molecular Modeling, J. Med. Chem., 2002, pp. 1748-1756, v. 45(9).
Scalzo, M et al, *Il Farmaco, Ed. Sc.* 43(9), (1988) 665-676.
Scalzo, M et al, *Il Farmaco Ed Sc.* 43(9) (1988) 677-691.
Scalzo, M et al, *Eur. J. Med. Chem.* (188) 23(6) 587-591.
Cerreto, F et al, *Eur. J. Med. Chem.* 27(7) (1992) 701-708.
Ueda, T et al, *Tetrahedron Letters*, 29(36) 4607-4610, (1988).

*Primary Examiner*—Kamal A Saeed
(74) *Attorney, Agent, or Firm*—George W. Johnston; Dennis P. Tramaloni; Brian C. Remy

(57) ABSTRACT

The present invention relates to compounds of formula (I)

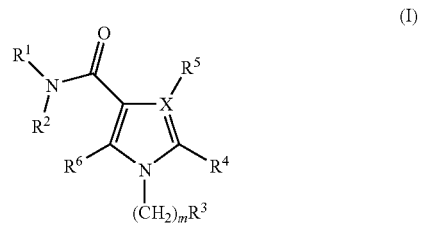

wherein $R^1$, $R^2$, $R^3$, $R^4$, $R^5$, $R^6$, m and X are as defined in the description and claims, and pharmaceutically acceptable salts thereof. The compounds are useful for the treatment and/or prophylaxis of diseases which are associated with the modulation of CB1 receptors.

26 Claims, No Drawings

CB 1 RECEPTOR INVERSE AGONISTS

PRIORITY TO RELATED APPLICATIONS

This application is a division of U.S. application Ser. No. 10/743,642, filed Dec. 22, 2003, which claims the benefit of European Patent Application No. 03000003.8, filed Jan. 2, 2003. The entire contents of the above-identified applications are hereby incorporated by reference.

BACKGROUND OF THE INVENTION

The present invention is concerned with novel pyrrole and imidazole derivatives, their manufacture, pharmaceutical compositions containing them and their use as medicaments.

The active compounds of the present invention are useful in treating obesity and other disorders.

Two different subtypes of cannabinoid receptors ($CB_1$ and $CB_2$) have been isolated and both belong to G protein coupled receptor superfamily. An alternative spliced form of $CB_1$, $CB_{1A}$, has also been described, but it did not exhibit different properties in terms of ligand binding and receptor activation than $CB_1$ (D. Shire, C. Carrillon, M. Kaghad, B. Calandra, M. Rinaldi-Carmona, G. Le Fur, D. Caput, P. Ferrara, J. Biol. Chem. 270 (8) (1995) 3726-31). The $CB_1$ receptor is mainly located in the brain, whereas the $CB_2$ receptor is predominately distributed in the peripherie primarily localized in spleen and cells of the immune system (S. Munro, K. L. Thomas, M. Abu-Shaar, Nature 365 (1993) 61-61). Therefore in order to avoid side effects a $CB_1$-selective compound is desirable.

$\Delta^9$-tetrahydrocannabinol ($\Delta^9$-THC) is the principal psychoactive compound in the Indian hemp (Y. Gaoni, R. Mechoulam, J. Am. Chem. Soc., 86 (1964) 1646), *canabis savita* (marijuanan), which is used in medicine since ages (R. Mechoulam (Ed.) in *"Cannabinoids as therapeutic Agents"*, 1986, pp. 1-20, CRC Press). $\Delta^9$-THC is a non-selective $CB_1/_2$ receptor agonist and is available in the USA as dronabinol (marinol®) for the alleviation of cancer chemotherapy-induced emesis (CIE) and the reversal of body weight loss experienced by AIDS patients through appetite stimulation. In the UK Nabolinone (LY-109514, Cesamet®), a synthetic analogue of $\Delta^9$-THC, is used for CIE (R. G. Pertwee, Pharmaceut. Sci. 3 (11) (1997) 539-545, E. M. Williamson, F. J. Evans, Drugs 60 (6) (2000) 1303-1314).

Anandamide (arachidonylethanolamide) was identified as the endogenous ligand (agonist) for $CB_1$ (R. G. Pertwee, Curr. Med. Chem., 6 (8) (1999) 635-664; W. A. Devane, L. Hanus, A. Breuer, R. G. Pertwee, L. A. Stevenson, G. Griffin, D. Gibson, A. Mandelbaum, A. Etinger, R. Mechoulam, Science 258 (1992) 1946-9). Anandamide and 2-arachidonoylglycerol (2-AG) modulate at the presynaptic nerve terminal negatively adenylate cyclase and voltage-sensitive $Ca^{2+}$ channels and activates the inwardly rectifying $K^+$ channel (V. Di Marzo, D. Melck, T. Bisogno, L. De Petrocellis, Trends in Neuroscience 21 (12) (1998) 521-8), thereby affecting neurotransmitter release and/or action, which decreases the release of neurotransmitter (A. C. Porter, C. C. Felder, Pharmacol. Ther., 90 (1) (2001) 45-60).

Anandamide as $\Delta^9$-THC also increases feeding through $CB_1$ receptor-mediated mechanism. $CB_1$ selective antagonists block the increase in feeding associated with administration of anandamide (C. M. Williams, T. C. Kirkham, Psychopharmacology 143 (3) (1999) 315-317; C. C. Felder, E. M. Briley, J. Axelrod, J. T. Simpson, K. Mackie, W. A. Devane, Proc. Natl. Acad. Sci. U.S.A. 90 (16) (1993) 7656-60) and caused appetite suppression and weight loss (G. Colombo, R. Agabio, G. Diaz, C. Lobina, R. Reali, G. L. Gessa, Life Sci. 63 (8) (1998) L113-PL117).

Leptin is the primary signal through which the hypothalamus senses nutritional state and modulates food intake and energy balance. Following temporary food restriction, CB1 receptor knockout mice eat less than their wild-type littermates, and the CB1 antagonist SR141716A reduces food intake in wild-type but not knockout mice. Furthermore, defective leptin signaling is associated with elevated hypothalamic, but not cerebellar, levels of endocannabinoids in obese db/db and ob/ob mice and Zucker rats. Acute leptin treatment of normal rats and ob/ob mice reduces anandamide and 2-arachidonoyl glycerol in the hypothalamus. These findings indicate that endocannabinoids in the hypothalamus may tonically activate CB1 receptors to maintain food intake and form part of the neural circuitry regulated by leptin (V. Di Marzo, S. K. Goparaju, L. Wang, J. Liu, S. Bitkai, Z. Jarai, F. Fezza, G. I. Miura, R. D. Palmiter, T. Sugiura, G. Kunos, Nature 410 (6830) 822-825).

SR-141716A, a CB1 selective antagonist/inverse agonist is undergoing currently phase III clinical trials for the treatment of obesity. In a double blind placebo-controlled study, at the doses of 5, 10 and 20 mg daily, SR 141716 significantly reduced body weight when compared to placebo (F. Barth, M. Rinaldi-Carmona, M. Arnone, H. Heshmati, G. Le Fur, *"Cannabinoid antagonists: From research tools to potential new drugs."* Abstracts of Papers, 222nd ACS National Meeting, Chicago, Ill., United States, Aug. 26-30, 2001).

Other compounds which have been proposed as CB1 receptor antagonists respectively inverse agonists are aminoalkylindols (AAI; M. Pacheco, S. R. Childers, R. Arnold, F. Casiano, S. J. Ward, J. Pharmacol. Exp. Ther. 257 (1) (1991) 170-183), like 6-bromo-(WIN54661; F. M. Casiano, R. Arnold, D. Haycock, J. Kuster, S. J. Ward, NIDA Res. Monogr. 105 (1991) 295-6) or 6-iodopravadoline (AM630, K. Hosohata, R. M. Quock, R. M; Hosohata, T. H. Burkey, A. Makriyannis, P. Consroe, W. R. Roeske, H. I. Yamamura, Life Sci. 61 (1997) 115-118; R. Pertwee, G. Griffin, S. Fernando, X. Li, A. Hill, A. Makriyannis, Life Sci. 56 (23-24) (1995) 1949-55). Arylbenzo[b]thiophene and benzo[b]furan (LY320135, C. C. Felder, K. E. Joyce, E. M. Briley, M. Glass, K. P. Mackie, K. J. Fahey, G. J. Cullinan, D. C. Hunden, D. W. Johnson, M. O. Chaney, G. A. Koppel, M. Brownstein, J. Pharmacol. Exp. Ther. 284 (1) (1998) 291-7) disclosed in WO9602248, U.S. Pat. No. 5,596,106, 3-alkyl-(5,5-diphenyl)imidazolidinediones (M. Kanyonyo, S. J. Govaerts, E. Hermans, J. H. Poupaert, D. M. Lambert, Bioorg. Med. Chem. Lett. 9 (15) (1999) 2233-2236.) as well as 3-alkyl-5-arylimidazolidinediones (F. Ooms, J. Wouters, O. Oscaro. T. Happaerts, G. Bouchard, P.-A. Carrupt, B. Testa, D. M. Lambert, J. Med. Chem. 45 (9) (2002) 1748-1756) are known to antagonize the $CB_1$ receptor respectively act as an inverse agonist on the $hCB_1$ receptor. WO0015609 (FR2783246-A1), WO0164634 (FR2805817-A1), WO0228346, WO0164632 (FR2805818-A1), WO0164633 (FR2805810-A1) disclosed substituted 1-bis(aryl)methyl-azetidines derivatives as antagonists of $CB_1$. In WO0170700 4,5-dihydro-1H-pyrazole derivatives are described as $CB_1$ antagonists. In several patents bridged and non-bridged 1,5-diphenyl-3-pyrazole-carboxamide derivatives are disclosed as $CB_1$ antagonists/inverse agonists (WO0132663, WO0046209, WO9719063, EP658546, EP656354, U.S. Pat. No. 5,624,941, EP576357, U.S. Pat. No. 3,940,418).

SUMMARY OF THE INVENTION

The present invention relates to compounds of formula (I):

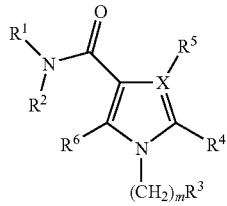

wherein $R^1$, $R^2$, $R^3$, $R^4$, $R^5$, $R^6$, m and X are as defined herewithin.

According to one aspect of the present invention there are provided selective, directly acting CB1 receptor antagonists respectively inverse agonists. Such antagonists/inverse antagonists are useful in medical therapy, particularly in the treatment and/or prevention of diseases which are associated with the modulation of CB1 receptors.

Unless otherwise indicated, the following definitions are set forth to illustrate and define the meaning and scope of the various terms used to describe the invention herein.

In this specification the term "lower" is used to mean a group consisting of one to eight, preferably of one to four carbon atom(s).

The term "halogen" refers to fluorine, chlorine, bromine and iodine, preferably to chlorine and fluorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl", alone or in combination with other groups, refers to a branched or straight-chain monovalent alkyl radical of one to eight carbon atoms, preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" refers to the group R'—O—, wherein R' is lower alkyl. Examples of lower alkoxy groups are e.g. methoxy, ethoxy, propoxy, isopropoxy, butoxy, isobutoxy and hexyloxy, with methoxy being especially preferred.

The term "lower alkylamino" refers to the group R'—NH—, wherein R' is lower alkyl.

The term "lower alkylsulfonyl" refers to the group R'—S(O)$_2$—, wherein R' is lower alkyl.

The term "halogenated lower alkyl" refers to a lower alkyl group wherein at least one of the hydrogens of the lower alkyl group is replaced by a halogen atom, preferably fluoro or chloro.

Among the preferred halogenated lower alkyl groups are trifluoromethyl, difluoromethyl, fluoromethyl and chloromethyl, with trifluoromethyl being especially preferred. The term "fluorinated lower alkyl" refers to a lower alkyl group wherein at least one of the hydrogens of the lower alkyl group is replaced by fluoro. Among the preferred fluorinated lower alkyl groups are trifluoromethyl, difluoromethyl and fluoromethyl, with trifluoromethyl being especially preferred.

The term "halogenated lower alkoxy" refers to a lower alkoxy group wherein at least one of the hydrogens of the lower alkoxy group is replaced by halogen, preferably by fluorine or chlorine.

Among the preferred halogenated lower alkoxy groups are fluorinated lower alkoxy groups such as trifluoromethoxy, difluoromethoxy and fluoromethoxy, with trifluoromethoxy being especially preferred. The term "fluorinated lower alkoxy" refers to a lower alkoxy group wherein at least one of the hydrogens of the lower alkoxy group is replaced by fluoro. Among the preferred fluorinated lower alkoxy groups are trifluoromethoxy, difluoromethoxy and fluoromethoxy, with trifluoromethoxy being especially preferred.

The term "cycloalkyl" refers to a monovalent carbocyclic radical of three to six, preferably three to five carbon atoms. This term is further exemplified by radicals such as cyclopropyl, cyclobutyl, cyclopentyl and cyclohexyl.

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

DETAILED DESCRIPTION OF THE INVENTION

The present invention relates to compounds of formula (I):

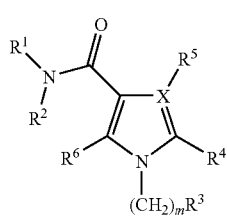

wherein
X is C or N;
$R^1$ is hydrogen or lower alkyl;
$R^2$ is lower alkyl or —(CH$_2$)$_n$—R$^{2a}$;
$R^{2a}$ is cycloalkyl, optionally mono-, di-, tri- or tetra-substituted, independently, by hydroxy, lower alkyl, lower alkoxy, fluorinated lower alkyl or fluorinated lower alkoxy; a 5-or 6-membered monovalent saturated heterocyclic ring containing one to three heteroatoms independently selected from nitrogen, oxygen and sulfur, said heterocyclic ring being optionally mono-, di- or tri-substituted, independently, by hydroxy, lower alkyl, lower alkoxy, amino, lower alkylamino, oxo, fluorinated lower alkyl or fluorinated lower alkoxy; a 5- or 6-membered monovalent heteroaromatic ring containing one to four heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino or cycloalkyl; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro;

$R^3$ is cycloalkyl, optionally mono-, di-, tri- or tetra-substituted, independently, by hydroxy, lower alkyl, lower alkoxy, fluorinated lower alkyl or fluorinated lower alkoxy; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro;

$R^4$ is a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino; naphthyl, which may optionally be mono-, di- or tri-substituted, independently, by hydroxy, lower alkyl, lower alkoxy, halogen, lower alkylamino, halogenated lower alkyl, halogenated lower alkoxy or nitro; or phenyl which may optionally be mono-, di- or tri-substituted, independently, by hydroxy, lower alkyl, lower alkoxy, halogen, nitro, halogenated lower alkyl, halogenated lower alkoxy, cyano, lower alkylsulfonyl or —$NR^7R^8$; or two adjacent substituents of the said phenyl residue together are —O—$(CH_2)_p$—O— or —$(CH_2)_2$—C(O)NH—;

$R^5$ and $R^6$ are each independently hydrogen, lower alkyl, halogen or fluorinated methyl;

$R^7$ and $R^8$ are each independently hydrogen or lower alkyl; or $R^7$ and $R^8$ together with the nitrogen atom to which they are attached form a 5- or 6-membered saturated or aromatic heterocyclic ring optionally containing one or two further heteroatoms independently selected from nitrogen, oxygen and sulfur, said saturated or aromatic heterocyclic ring being optionally substituted by hydroxy, lower alkyl, lower alkoxy, halogen, amino or lower alkylamino;

m is 1 or 2;

n is 0 or 1;

p is 1, 2 or 3;

or pharmaceutically acceptable salts thereof.

In one embodiment, the present invention relates to a compound of formula (I) as defined above, wherein $R^1$ is hydrogen or lower alkyl.

Preferable lower alkyl residues $R^1$ are methyl and ethyl, with methyl being especially preferred.

Most preferably, $R^1$ is hydrogen.

In another embodiment, the present invention relates to a compound of formula (I) as defined above, wherein $R^2$ is lower alkyl or —$(CH_2)_n$—$R^{2a}$.

Preferable lower alkyl residues $R^2$ are branched or straight chain alkyl residues with one to eight, preferably three to five carbon atoms, such as n-propyl, isopropyl, n-butyl, s-butyl, isobutyl, n-pentyl and 2-ethylhexyl. Most preferred lower alkyl residues $R^2$ are n-propyl, n-butyl, s-butyl, isobutyl and n-pentyl, with n-butyl being especially preferred. Preferable residues —$(CH_2)_n$—$R^{2a}$ are those wherein n is O and $R^{2a}$ is as defined below.

In one embodiment, $R^{2a}$ is cycloalkyl, optionally mono-, di-, tri- or tetra-substituted, independently, by hydroxy, lower alkyl, lower alkoxy, fluorinated lower alkyl or fluorinated lower alkoxy; a 5- or 6-membered monovalent saturated heterocyclic ring containing one to three heteroatoms independently selected from nitrogen, oxygen and sulfur, said heterocyclic ring being optionally mono-, di- or tri-substituted, independently, by hydroxy, lower alkyl, lower alkoxy, amino, lower alkylamino, oxo, fluorinated lower alkyl or fluorinated lower alkoxy; a 5-or 6-membered monovalent heteroaromatic ring containing one to four heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino or cycloalkyl; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro.

Preferable cycloalkyl residues $R^{2a}$ are cycloalkyl residues with three to six carbon atoms, such as cyclopropyl, cyclobutyl, cyclopentyl and cyclohexyl, which may optionally be mono-, di-, tri- or tetra-substituted, independently, by hydroxy, lower alkyl, lower alkoxy, fluorinated lower alkyl or fluorinated lower alkoxy, preferably by lower alkyl, such as methyl, and/or hydroxy. Most preferable unsubstituted cycloalkyl residues $R^{2a}$ are unsubstituted cyclopropyl, cyclobutyl, cyclopentyl and cyclohexyl, with cyclohexyl being especially preferred. Most preferable substituted cycloalkyl residues $R^{2a}$ are cyclopropyl, cyclobutyl, cyclopentyl and cyclohexyl, with 2-hydroxy-cyclohexyl being especially preferred. Preferable heterocyclic rings $R^{2a}$ are 5- or 6-membered, with 5-membered being especially preferred, and contain one to three, preferably one or two, heteroatoms independently selected from nitrogen, oxygen and sulfur, preferably selected form nitrogen and oxygen, said heterocyclic ring being optionally mono-, di- or tri-substituted, independently, by hydroxy, lower alkyl, lower alkoxy, amino, lower alkylamino, oxo, fluorinated lower alkyl or fluorinated lower alkoxy. Examples of heterocyclic rings $R^{2a}$ are tetrahydrofuranyl, piperidinyl and isoxazolyl, optionally substituted as defined above. Preferably, heterocyclic rings $R^{2a}$ are unsubstituted or substituted by lower alkyl, such as methyl, or by oxo. Most preferred heterocyclic rings $R^{2a}$ are tetrahydrofuranyl, 2,2-dimethyl-tetrahydrofuranyl, piperidinyl and isoxazolidinone. Preferable heteroaromatic rings $R^{2a}$ are 5- or 6-membered and contain one to four, preferably one, two or four, heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino or cycloalkyl. Examples of heteroaromatic rings $R^{2a}$ are thienyl, furyl, tetrazolyl, imidazolyl and pyrazolyl, optionally substituted as defined above. Preferably, heteroaromatic rings $R^{2a}$ are unsubstituted or mono-substituted by lower alkyl, such as methyl, or by cycloalkyl, such as cyclopropyl. Most preferable heteroaromatic rings $R^{2a}$ are thienyl, furyl, 2-methyl-furyl, tetrazolyl, imidazolyl and 3-cyclopropyl-pyrazolyl. Preferable phenyl residues $R^{2a}$ are optionally mono-, di- or tri-substituted, preferably mono- or di-substituted, independently, by lower alkoxy, such as methoxy, halogen, such as chloro, halogenated lower alkyl, such as trifluoromethyl, halogenated lower alkoxy, such as trifluoromethoxy, or nitro. Most preferable phenyl residues $R^{2a}$ are unsubstituted phenyl, 4-trifluoromethyl-phenyl, 4-chloro-phenyl, 3,4-dichloro-phenyl, 3,4-dimethoxy-phenyl, 2-nitro-phenyl and 4-trifluoromethoxy-phenyl.

In another embodiment, the present invention relates to a compound of formula (I) as defined above, wherein $R^3$ is cycloalkyl, optionally mono-, di-, tri- or tetra-substituted, independently, by hydroxy, lower alkyl, lower alkoxy, fluorinated lower alkyl or fluorinated lower alkoxy; or phenyl, which may optionally be mono-, di- or tri-substituted, independently, by hydroxy, lower alkyl, lower alkoxy, halogen, lower alkylamino, halogenated lower alkyl, halogenated lower alkoxy or nitro.

Preferable cycloalkyl residues $R^3$ are cycloalkyl residues with three to six carbon atoms, such as cyclopropyl, cyclobutyl, cyclopentyl and cyclohexyl, which may optionally be mono-, di-, tri- or tetra-substituted, independently, by hydroxy, lower alkyl, lower alkoxy, fluorinated lower alkyl or fluorinated lower alkoxy, preferably by lower alkyl, such as methyl, and/or hydroxyl. Most preferable unsubstituted cycloalkyl residues $R^3$ are unsubstituted cyclopropyl, cyclobutyl, cyclopentyl and cyclohexyl, with cyclohexyl being especially preferred. Most preferable substituted cycloalkyl residues $R^3$ are substituted cyclopropyl, cyclobutyl, cyclopentyl and cyclohexyl, with substituted cyclohexyl being especially preferred. Preferable phenyl residues $R^3$ are optionally mono-, di- or tri-substituted, preferably mono- or di-substituted, independently, by lower alkoxy, such as methoxy, halogen, such as chloro, halogenated lower alkyl, such as trifluoromethyl, halogenated lower alkoxy, such as trifluoromethoxy, or nitro. Most preferable phenyl residues $R^{2a}$ are unsubstituted phenyl, 4-trifluoromethyl-phenyl, 4-chloro-phenyl, 3,4-dichloro-phenyl, 3,4-dimethoxy-phenyl, 2-nitro-phenyl and 4-trifluoromethoxy-phenyl.

In another embodiment, the present invention relates to a compound of formula (I) as defined above, wherein $R^4$ is a 5- or 6-membered monovalent heteroaromatic ring containing one to three heteroatoms independently selected from nitrogen, oxygen and sulfur, said heteroaromatic ring being optionally mono-, di- or tri-substituted, independently, by hydroxy, lower alkyl, lower alkoxy, halogen, amino, lower alkylamino; naphthyl, which may optionally be mono-, di- or tri-substituted, independently, by hydroxy, lower alkyl, lower alkoxy, halogen, lower alkylamino, halogenated lower alkyl, halogenated lower alkoxy or nitro; or phenyl which may optionally be mono-, di- or tri-substituted, independently, by hydroxy, lower alkyl, lower alkoxy, halogen, nitro, halogenated lower alkyl, halogenated lower alkoxy, cyano, lower alkylsulfonyl or —$NR^7R^8$; or two adjacent substituents of the said phenyl residue together are —O—$(CH_2)_p$—O— or —$(CH_2)_2$—C(O)NH—. Preferable heteroaromatic rings $R^4$ are 5- or 6-membered, preferably 6-membered, and contain one to three, preferably one or two, heteroatoms independently selected from nitrogen, oxygen and sulfur, preferably nitrogen, said heteroaromatic ring being optionally mono-, di- or tri-substituted, independently, by hydroxy, lower alkyl, lower alkoxy, halogen, amino or lower alkylamino. Examples of heteroaromatic rings $R^4$ are pyridinyl, pyrimidinyl and pyrazinyl, preferably pyridinyl and pyrazinyl, optionally substituted as defined above. Preferably, heteroaromatic rings $R^4$ are unsubstituted or mono-substituted by lower alkyl, such as methyl and ethyl. Most preferable heteroaromatic rings $R^4$ are pyridinyl, pyrazinyl, 4-methyl-pyridinyl, 3-methyl-pyrazinyl, 3-ethyl-pyrazinyl and 3,5-dimethyl-pyrazinyl. Preferably, naphthyl residues $R^4$ are unsubstituted. Preferable phenyl residues $R^4$ are optionally mono-, di- or tri-substituted, independently, by hydroxy, lower alkyl, such as methyl and t-butyl, lower alkoxy, such as methoxy, halogen, such as chloro, fluoro and bromo, nitro, halogenated lower alkyl, such as trifluoromethyl, halogenated lower alkoxy, such as di- and trifluoromethoxy, cyano, lower alkylsulfonyl, such as methylsulfonyl, or by —$NR^7R^8$, wherein $R^7$ and $R^8$ are as defined below; or two adjacent substituents of the said phenyl residue together are —O—$(CH_2)_p$—O— or —$(CH_2)_2$—C(O)NH—, and p is 1, 2 or 3, preferably 2 or 3.

Preferable —$NR^7R^8$ substituents of a phenyl residue $R^4$ are those wherein $R^7$ and $R^8$ are each independently hydrogen or lower alkyl, such as methyl and ethyl. Preferably, both $R^7$ and $R^8$ are methyl or both $R^7$ and $R^8$ are ethyl. Further preferable —$NR^7R^8$ substituents of a phenyl residue $R^4$ are those wherein $R^7$ and $R^8$ together with the nitrogen atom to which they are attached form a 5- or 6-membered, preferably 5-membered, saturated or aromatic, preferably saturated, heterocyclic ring optionally containing one or two, preferably one, further heteroatom(s) independently selected from nitrogen, oxygen and sulfur, preferably selected from nitrogen and oxygen, said saturated or aromatic heterocyclic ring being optionally mono- or di-substituted, preferably mono-substituted, independently, by hydroxy, lower alkyl, lower alkoxy, halogen, amino or lower alkylamino, preferably by lower alkyl, such as methyl. Preferably, the said saturated or aromatic heterocyclic ring formed by $R^7$ and $R^8$ together with the nitrogen atom to which they are attached is unsubstituted and does not contain any further heteroatom. Most preferable saturated or aromatic heterocyclic ring formed by $R^7$ and $R^8$ together with the nitrogen atom to which they are attached are pyrrolidinyl, piperidinyl, piperazinyl, 4-methyl-piperazinyl, imidazolyl, and morpholino, with pyrrolidinyl being especially preferred. Preferably, —$NR^7R^8$ substituents of a phenyl residue $R^4$ are at the para-position. Most preferable phenyl residues $R^4$ are mono- or di-substituted, independently, by halogen, such as chloro and fluoro, halogenated lower alkyl, such as trifluoromethyl, lower alkoxy, such as methoxy, or mono-substituted at the para-position by a residue —$NR^7R^8$, preferably by pyrrolidinyl.

In another embodiment, the present invention relates to a compound of formula (I) as defined above, wherein $R^5$ and $R^6$ are each independently hydrogen, lower alkyl, halogen or fluorinated methyl.

Preferable lower alkyl residues $R^5$ and $R^6$ are methyl and ethyl, with methyl being especially preferred. Preferable halogen residues $R^5$ and $R^6$ are fluoro and chloro, with chloro being especially preferred. Preferable residue $R^5$ is lower alkyl, such as methyl. Preferable residues $R^6$ are hydrogen and lower alkyl, such as methyl.

In one embodiment of the present invention X is C. In another embodiment of the present invention X is N.

The symbol m is 1 or 2; more preferably, m is 1.

The symbol n is 0 or 1; more preferably, n is 0.

The symbol p is 1, 2 or 3; more preferably, p is 2 or 3.

Preferred compounds of general formula (I) are the compounds of Examples 1 to 66 and 67 to 306 (see section Examples below) and pharmaceutically acceptable salts thereof. Especially preferred are the compounds selected from the group consisting of:

Cyclohexylmethyl-5-(4-methoxy-phenyl)-2-methyl-1H-pyrrole-3-carboxylic acid butylamide, Cyclohexylmethyl-5-(3-methoxy-phenyl)-2-methyl-1H-pyrrole-3-carboxylic acid butylamide, Cyclohexylmethyl-2-methyl-5-(4-trifluoromethyl-phenyl)-1H-pyrrole-3-carboxylic acid butylamide, 5-(4-Chloro-phenyl)-1-cyclohexylmethyl-2-methyl-1H-pyrrole-3-carboxylic acid butylamide, Cyclohexylmethyl-2-methyl-5-p-tolyl-1H-pyrrole-3-carboxylic acid butylamide, Cyclohexylmethyl-5-(2-methoxy-phenyl)-2-methyl-1H-pyrrole-3-carboxylic acid butylamide, Cyclohexylmethyl-5-(4-fluoro-phenyl)-2-methyl-1H-pyrrole-3-carboxylic acid butylamide, Cyclohexylmethyl-5-(2,4-dimethoxy-phenyl)-2-methyl-1H-pyrrole-3-carboxylic acid butylamide, 5-(4-Bromo-phenyl)-1-cyclohexylmethyl-2-methyl-1H-pyrrole-3-carboxylic acid butylamide, 5-(3-Cyano-phenyl)-1-cyclohexylmethyl-2-methyl-1H-pyrrole-3-carboxylic acid butylamide, Cyclohexylmethyl-5-(2,4-dimethyl-phenyl)-2-methyl-1H-pyrrole-3-carboxylic acid butylamide, Cyclohexylmethyl-5-(4-difluoromethoxy-phenyl)-2-methyl-1H-pyrrole-3-carboxylic acid butylamide,
Cyclohexylmethyl-2-methyl-5-(4-pyrrolidin-1-yl-phenyl)-1H-pyrrole-3-carboxylic acid butylamide,
Cyclohexylmethyl-5-(2,5-dimethoxy-phenyl)-2-methyl-1H-pyrrole-3-carboxylic acid butylamide,
Cyclohexylmethyl-5-(3,4-difluoro-phenyl)-2-methyl-1H-pyrrole-3-carboxylic acid butylamide,
5-(3-Chloro-phenyl)-1-cyclohexylmethyl-2-methyl-1H-pyrrole-3-carboxylic acid butylamide,
Cyclohexylmethyl-2-methyl-5-(4-trifluoromethoxy-phenyl)-1H-pyrrole-3-carboxylic acid butylamide,
Cyclohexylmethyl-5-(3,4-dimethoxy-phenyl)-2-methyl-1H-pyrrole-3-carboxylic acid butylamide,
5-(2-Chloro-phenyl)-1-cyclohexylmethyl-2-methyl-1H-pyrrole-3-carboxylic acid butylamide,
Cyclohexylmethyl-2-methyl-5-(4-nitro-phenyl)-1H-pyrrole-3-carboxylic acid butylamide,
Cyclohexylmethyl-5-(2,5-dimethoxy-phenyl)-2-methyl-1H-pyrrole-3-carboxylic acid cyclohexylamide,
Cyclohexylmethyl-5-(2,5-dimethoxy-phenyl)-2-methyl-1H-pyrrole-3-carboxylic acid cyclopentylamide,
Cyclohexylmethyl-5-(2,5-dimethoxy-phenyl)-2-methyl-1H-pyrrole-3-carboxylic acid cyclobutylamide,
Cyclohexylmethyl-5-(2,5-dimethoxy-phenyl)-2-methyl-1H-pyrrole-3-carboxylic acid cyclopropylamide,
Cyclohexylmethyl-5-(2,5-difluoro-phenyl)-2-methyl-1H-pyrrole-3-carboxylic acid butylamide,
Cyclohexylmethyl-5-(4-hydroxy-3-methoxy-phenyl)-2-methyl-1H-pyrrole-3-carboxylic acid butylamide,
Cyclohexylmethyl-5-(3-fluoro-phenyl)-2-methyl-1H-pyrrole-3-carboxylic acid butylamide,
5-Benzo[1,3]dioxol-5-yl-1-cyclohexylmethyl-2-methyl-1H-pyrrole-3-carboxylic acid butylamide,
Cyclohexylmethyl-5-(2,5-dichloro-phenyl)-2-methyl-1H-pyrrole-3-carboxylic acid butylamide,
5-(3,5-Bis-trifluoromethyl-phenyl)-1-cyclohexylmethyl-2-methyl-1H-pyrrole-3-carboxylic acid butylamide,
5-(3,5-Bis-trifluoromethyl-phenyl)-1-cyclohexylmethyl-2-methyl-1H-pyrrole-3-carboxylic acid cyclohexylamide,
Cyclohexylmethyl-2-methyl-5-(4-pyrrolidin-1-yl-phenyl)-1H-pyrrole-3-carboxylic acid cyclohexylamide,
(R)-1-Cyclohexylmethyl-5-(2,5-dimethoxy-phenyl)-2-methyl-1H-pyrrole-3-carboxylic acid sec-butylamide,
5-(3,5-Bis-trifluoromethyl-phenyl)-1-(4-methoxy-benzyl)-2-methyl-1H-pyrrole-3-carboxylic acid cyclohexylamide,
Cyclohexylmethyl-5-(2,5-dimethoxy-phenyl)-2-methyl-1H-pyrrole-3-carboxylic acid piperidin-1-ylamide,
Cyclohexylmethyl-2-methyl-5-pyridin-2-yl-1H-pyrrole-3-carboxylic acid butylamide,
Cyclohexylmethyl-2-(2-methoxy-phenyl)-5-methyl-1H-imidazole-4-carboxylic acid butylamide,
Cyclohexylmethyl-2-(2-methoxy-phenyl)-5-methyl-1H-imidazole-4-carboxylic acid piperidin-1-ylamide,
and pharmaceutically acceptable salts thereof.

Additional particularly preferred compounds from examples 67 to 306 are
Cyclohexylmethyl-5-(2,5-dimethoxy-phenyl)-2-methyl-1H-pyrrole-3-carboxylic acid cyclopropylmethyl-amide
Cyclohexylmethyl-5-(2,5-dimethoxy-phenyl)-2-methyl-1H-pyrrole-3-carboxylic acid (furan-2-ylmethyl)-amide
Cyclohexylmethyl-5-(2,5-dimethoxy-phenyl)-2-methyl-1H-pyrrole-3-carboxylic acid (3-methyl-thiophen-2-ylmethyl)-amide
(S)-1-Cyclohexylmethyl-5-(2,5-dimethoxy-phenyl)-2-methyl-1H-pyrrole-3-carboxylic acid sec-butylamide 5-(5-Chloro-2-methoxy-4-methyl-phenyl)-1-cyclohexylmethyl-2-methyl-1H-pyrrole-3-carboxylic acid cyclohexylamide
5-(3,5-Bis-trifluoromethyl-phenyl)-1-cyclohexylmethyl-2-methyl-1H-pyrrole-3-carboxylic acid piperidin-1-ylamide
Cyclohexylmethyl-5-(5-fluoro-2-methoxy-phenyl)-2-methyl-1H-pyrrole-3-carboxylic acid piperidin-1-ylamide
5-(5-Chloro-2-methoxy-phenyl)-1-cyclohexylmethyl-2-methyl-1H-pyrrole-3-carboxylic acid piperidin-1-ylamide
5-(5-Chloro-2-methoxy-4-methyl-phenyl)-1-cyclohexylmethyl-2-methyl-1H-pyrrole-3-carboxylic acid piperidin-1-ylamide
5-(2-Chloro-5-trifluoromethyl-phenyl)-1-cyclohexylmethyl-2-methyl-1H-pyrrole-3-carboxylic acid ((1RS,2RS)-2-hydroxy-cyclohexyl)-amide
5-(2-Chloro-5-trifluoromethyl-phenyl)-1-cyclohexylmethyl-2-methyl-1H-pyrrole-3-carboxylic acid ((1R,2R)-2-hydroxy-cyclohexyl)-amide
5-(2,5-Bis-trifluoromethyl-phenyl)-1-cyclohexylmethyl-2-methyl-1H-pyrrole-3-carboxylic acid piperidin-1-ylamide
5-(2-Chloro-5-trifluoromethyl-phenyl)-1-cyclohexylmethyl-2-methyl-1H-pyrrole-3-carboxylic acid piperidin-1-ylamide
5-(2-Fluoro-5-trifluoromethyl-phenyl)-1-((1SR,2RS)-2-hydroxy-cyclohexylmethyl)-2-methyl-1H-pyrrole-3-carboxylic acid cyclohexylamide
5-(2-Fluoro-5-trifluoromethyl-phenyl)-1-((1RS,2RS)-2-hydroxy-cyclohexylmethyl)-2-methyl-1H-pyrrole-3-carboxylic acid cyclohexylamide
5-(2-Fluoro-5-trifluoromethyl-phenyl)-1-(1RS,2RS)-2-hydroxy-cyclohexylmethyl)-2-methyl-1H-pyrrole-3-carboxylic acid ((1R,2R)-2-hydroxy-cyclohexyl)-amide
5-(2,5-Bis-trifluoromethyl-phenyl)-1-(2-cyclopropyl-ethyl)-2-methyl-1H-pyrrole-3-carboxylic acid ((1R,2R)-2-hydroxy-cyclohexyl)-amide
5-(2-Chloro-5-trifluoromethyl-phenyl)-1-((1RS,2RS)-2-hydroxy-cyclohexylmethyl)-2-methyl-1H-pyrrole-3-carboxylic acid cyclohexylamide
Cyclohexylmethyl-2-methyl-5-(2-methyl-5-trifluoromethyl-phenyl)-1H-pyrrole-3-carboxylic acid ((1R,2R)-2-hydroxy-cyclohexyl)-amide and pharmaceutically acceptable salts thereof.

The present invention also relates to a process for the manufacture of compounds of formula (I) as defined above. The compounds of formula (I) can be manufactured by the methods given below, by the methods given in the Examples or by analogous methods. Appropriate reaction conditions for the individual reaction steps are known to the person skilled in the art. Starting materials are either commercially available or can be prepared by methods analogous to the methods given below or in the Examples or by methods known in the art.

The compounds of formula (I) may be prepared using the general methods described below:

Compounds of formula (I), wherein $R^1$ to $R^6$ and m are as previously defined and X═C, can be prepared by reaction of enamines of formula A with alfa-bromoketones of formula B according to methods known in the art (Scheme 1). For example, the reaction can be performed in an inert solvent, such as DMF, in the presence of a hindered base, such as 2,6-di-tert-butylpyridine or 2,6-lutidine.

Scheme 1

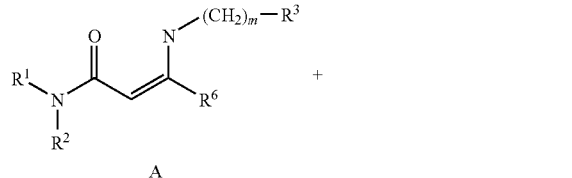

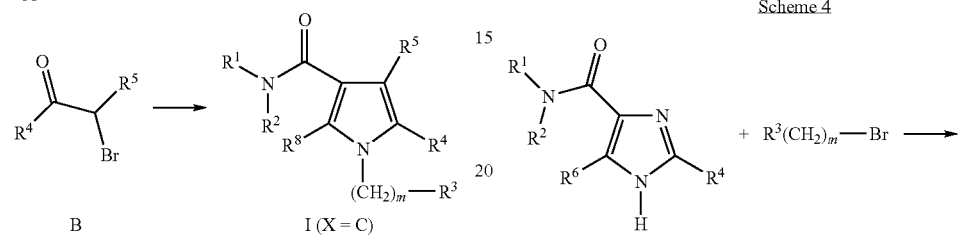

Enamines of formula A can be prepared from beta-ketoamides of formula C and amines of formula D by methods known in the art (Scheme 2). For example a beta-keto amide of formula C can be reacted with an amine of formula D in a suitable inert solvent (e.g. DMF) in the presence of a hindered base (e.g. 2,6-di-tert-butylpyridine) to yield enamine of formula A.

Scheme 2

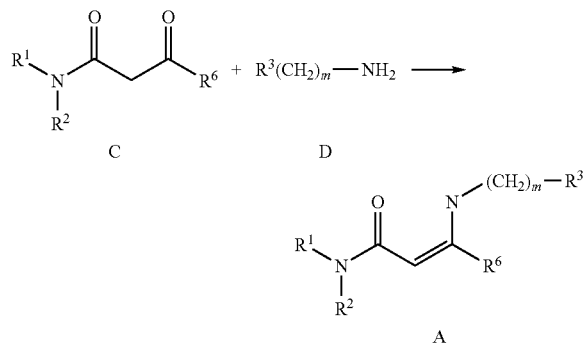

Beta-ketoamides of formula C can be purchased from commercial sources or can be prepared by methods known in the art. For example, beta-ketoamides of formula C wherein $R^6$=methyl can be prepared by reaction of amines of formula E with diketene in an inert solvent, such as dichloromethane (Scheme 3).

Scheme 3

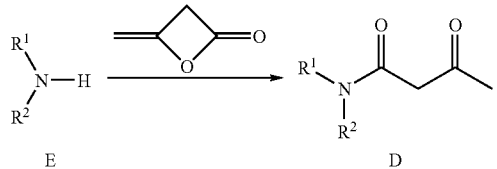

Compounds of formulae B and D are either known from the literature or can be purchased from commercial sources or else can be synthesized by methods known in the art.

Compounds of formula (I), wherein $R^1$ to $R^6$ and m are as previously defined and X=N, can be prepared by alkylation of imidazoles of formula F according to methods known in the art (Scheme 4). For example, imidazoles of formula F may be reacted with alkyl bromides of formula G in the presence of a base (e.g. potassium tert-butylate) in an inert solvent, such as acetonitrile.

Scheme 4

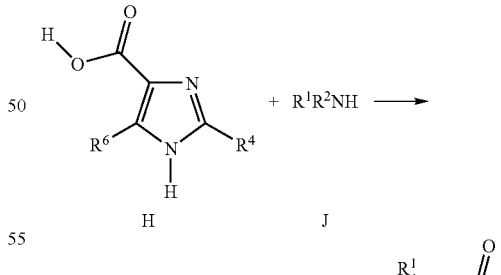

Compounds of formula H can be coupled with an appropriate amine of formula J by methods known in the art (Scheme 5). The reaction can be performed in a suitable inert solvent (e.g. DMF, dichloromethane, pyridine or THF) in the presence of a base (e.g. Hünigs' base) and an activating agent (e.g. TBTU=O-(Benzotriazol-1-yl)-N,N',N'-tetramethyluronium-tetrafluoroborat) to yield the corresponding amides of formula F.

Scheme 5

Compounds of formula H can be obtained by hydrolysis of compounds of formula K by methods known in the art (Scheme 6). For example, the reaction can proceed in a polar solvent (e.g. ethanol) in the presence of a base (e.g. sodium hydroxide).

Scheme 6

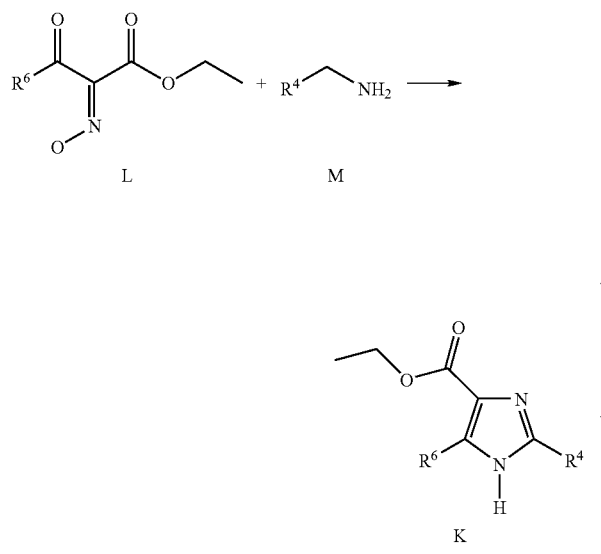

Imidazoles of formula K can be prepared by the reaction of 2-oximinoacetoacetates of formula L with an appropriate amine of formula M by methods known in the art (Scheme 7). For example, the reaction can proceed in a polar solvent (e.g. acetonitrile) at elevated temperature.

Scheme 7

Compounds of formula G, J, L and M are either known from the literature or can be purchased from commercial sources or else can be synthesized by methods known in the art.

Alternatively, compounds of formula (I), wherein $R^1$ to $R^6$ and m are as previously defined and X=C, can also be prepared from compounds of formula N by coupling with an appropriate amine of formula J by methods known in the art (Scheme 8). The reaction can be performed in a suitable inert solvent (e.g. DMF, dichloromethane, pyridine or THF) in the presence of a base (e.g. Hünigs' base) and an activating agent (e.g. TBTU=O-(Benzotriazol-1-yl)-N,N',N'-tetramethyl-uronium-tetrafluoroborate) to yield the corresponding amides of formula I Scheme 8

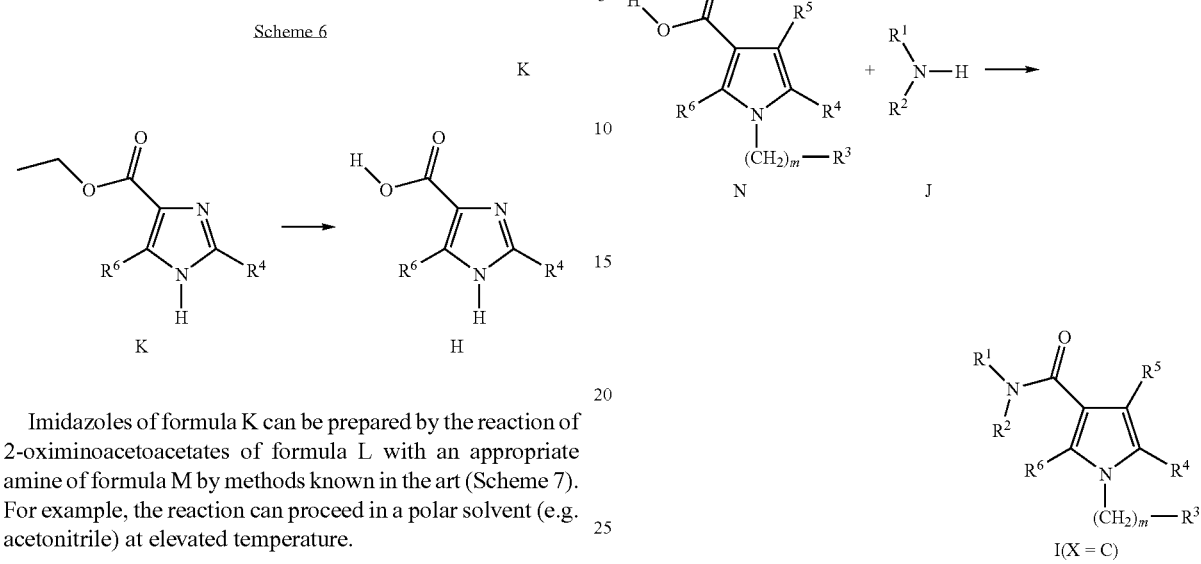

Compounds of formula N can be obtained by hydrolysis of compounds of formula O by methods known in the art (Scheme 9). For example, the reaction can proceed in a polar solvent (e.g. ethanol) in the presence of base (e.g. sodium hydroxide).

Scheme 9

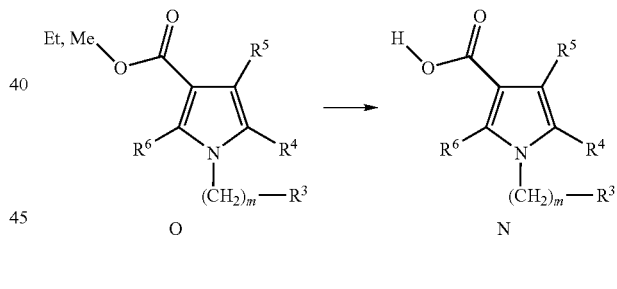

Compounds of formula O can be prepared by methods known in the art as exemplified in Scheme 10. For example they can be prepared by the condensation of amines or anilines of formula Q with 1,4-diketones of formula P.

Amines or anilines of formula Q are either known from the literature or can be purchased from commercial sources or else can be synthesized by methods know in the art.

Scheme 10

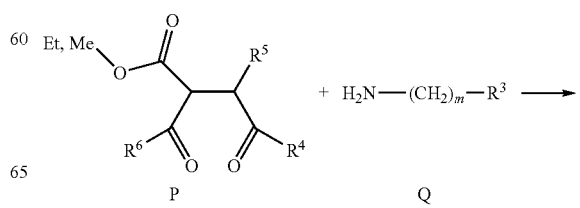

-continued

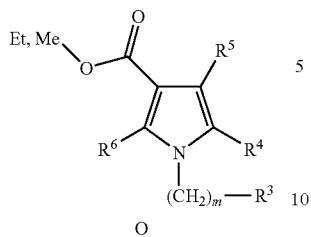

Diketones of formula P can be prepared by methods known from the literature. For example they can be produced by the reaction of ketoesters of formula R with bromoketones of formula S (Scheme 11).

Scheme 11

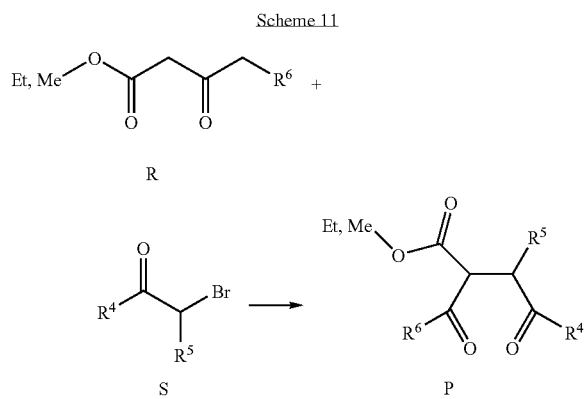

Ketoesters of formula R are either known from the literature or can be purchased from commercial sources or else can be synthesized by methods know in the art.

Bromoketones of formula S are either known from the literature or can be purchased from commercial sources or else can be synthesized by methods known in the art. For example they can be synthesized from the corresponding ketones of formula V by bromination methods using for example bromine or $CuBr_2$.

Ketones of formula V are either known from the literature or can be purchased from commercial sources or else can be synthesized by methods known in the art. For example the ketones of formula V can be produced from the corresponding carboxylic acids or acyl halides of formula T in two steps via Weinreb's amide of formula V.

Carboxylic acids of formula T are either known from the literature or can be purchased from commercial sources or else can be synthesized by methods know in the art.

Scheme 12

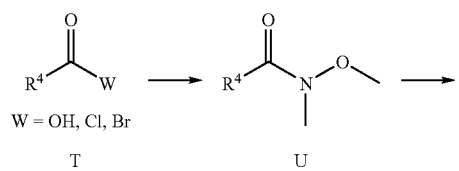

-continued

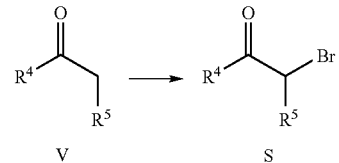

The invention further relates to compounds of formula (I) as defined above, when manufactured according to a process as defined above.

Some compounds of formula (I) may possess asymmetric centres and are therefore capable of existing in more than one stereoisomeric form. The invention thus also relates to compounds in substantially pure isomeric form at one or more asymmetric centres as well as mixtures, including racemic mixtures, thereof. Such isomers may be prepared by asymmetric synthesis, for example using chiral intermediate, or mixtures may be resolved by conventional methods, e.g., chromatography (chromatography with a chiral adsorbens or eluent), or use of a solving agent.

It will be appreciated, that the compounds of general formula (I) in this invention may be derivatised at functional groups to provide derivatives which are capable of conversion back to the parent compound in vivo.

As described above, the compounds of formula (I) or pharmaceutically acceptable salts thereof can be used as medicaments for the treatment and/or prophylaxis of diseases which are associated with the modulation of the CB1 receptors.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with the modulation of CB1 receptors.

In another embodiment, the invention relates to a method for the treatment and/or prophylaxis of diseases which are associated with the modulation of CB1 receptors, which method comprises administering a compound as defined above to a human being or animal.

The invention further relates to the use of compounds as defined above for the treatment and/or prophylaxis of diseases which are associated with the modulation of CB1 receptors.

In addition, the invention relates to the use of compounds as defined above for the preparation of medicaments for the treatment and/or prophylaxis of diseases which are associated with the modulation of CB1 receptors. Such medicaments comprise a compound as defined above.

In this context, the expression 'diseases associated with modulation of CB1 receptors' means diseases which can be treated and/or prevented by modulation of CB1 receptors. Such diseases encompass, but are not limited to, psychic disorders, especially anxiety, psychosis, schizophrenia, depression, abuse of psychotropes, for example for the abuse and/or dependence of a substances, including alcohole dependency and nicotine dependency, neuropathies, migraine, stress, epilepsy, dyskinesias, Parkinson's disease, amnesia, cognitive disorders, senile dementia, Alzheimer's disease, eating disorders, obesity, diabetes type II or non insulin dependent diabetes (NIDD), gastrointestinal diseases, vomiting, diarrhea, urinary disorders, cardiovascular disorders, infertility disorders, inflammations, infections, cancer, neuroinflammation, in particular in atherosclerosis, or the Guillain-Barré syndrome, viral encephalitis, cerebral vascular incidents and cranial trauma.

In a preferable aspect, the expression 'diseases associated with modulation of CB1 receptors' relates to eating disorders, obesity, diabetes type II or non insulin dependent diabetes (NIDD), neuroinflammation, diarrhea, abuse and/or dependence of a substances, including alcohole dependency and nicotine dependency. In a more preferable aspect, the said term related to eating disorders, obesity, diabetes type II or non insulin dependent diabetes (NIDD), abuse and/or dependence of a substances, including alcohole dependency and nicotine dependency, with obesity being especially preferred.

It is a further preferred object to provide a method of treatment or prevention of Type II diabetes (non-insulin dependent diabetes mellitus (NIDDM) in a human which comprises administration of a therapeutically effective amount of a compound according to formula (I) in combination or association with a therapeutically effective amount of a lipase inhibitor, particularly, wherein the lipase inhibitor is orlistat. Also an object of the invention is the method as described above for the simultaneous, separate or sequential administration of a compound according to formula (I) and a lipase inhibitor, particularly tetrahydrolipstatin.

It is a further preferred object to provide a method for the treatment or prevention of obesity and obesity related disorders which comprises administration of a therapeutically effective amount of a compound according to formula (I) in combination or association with a therapeutically effective amount of other drugs for the treatment of obesity or eating disorders so that together they give effective relief. Suitable other drugs include but are not limited to anorectic agents, lipase inhibitors and selective serotonin reuptake inhibitors (SSRI). Combinations or associations of the above agents may be encompassing separate, sequential or simultaneous administration.

Preferable lipase inhibitor is tetrahydrolipstatin.

Suitable anorectic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine, and pharmaceutically acceptable salts thereof.

Most preferable anorectic agents are sibutramine and phentermine.

Suitable selective serotonin reuptake inhibitors of use in combination with a compound of the present invention include: fluoxetine, fluvoxamine, paroxetine and sertraline, and pharmaceutically acceptable salts thereof.

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

In addition, to demonstrate CNS activities of the compounds of the present invention, the following in vivo assays may be used.

Method for Testing Task Learning and Spatial Memory

The Morris Water Maze is routinely used to assess task learning and spatial memory (Jaspers et al., Neurosci. Lett. 117:149-153, 1990; Morris, J. Neurosci. Methods 11:47-60, 1984). In this assay, animals are placed in a water pool which is divided into quadrants. One platform is hidden in one of the quadrants. The animal is placed in the water pool and is expected to locate the hidden platform within a predetermined time. During a number of training trials, the animal learns the location of the platform and escape from the pool. The animal receives multiple trials in this task. Total distance traveled, number of trials to locate platform, latency to find platform, and the swimming path is recorded for each animal. The animal's learning ability is measured by the length of time or number of trials required to find the hidden platform. Memory deficit or improvement is determined by the number of trials or the latency to find the platform at predetermined delay time after acquisition. Leaning and memory may be measured by the number of times that the animal crosses the quadrant where the platform was located during the acquisition phase.

Method for Testing Drug Dependence

Self-administration in animals is a predictor of a compound's abuse potential in humans. Modifications to this procedure may also be used to identify compounds that prevent or block the reinforcing properties of drugs that have abuse potential. A compound that extinguishes the self-administration of a drug may prevent that drug's abuse or its dependence. (Ranaldi et al., Psychopharmacol. 161:442-448, 2002; Campbell et al., Exp. Clin. Psychopharmacol. 8:312-25, 2000). In a self-administration test, animals are placed in the operant chambers containing both an active and inactive lever. Each response on the active lever produces an infusion of either the test compound or a drug known to be self-administered. Presses on the inactive lever have no effect, but are also recorded. Animals are then trained to self-administer compound/drug over a set period of time by having drug access during each daily session. Illumination of the chamber house light signals the beginning of the session and the availability of the compound/drug. When the session ends, the house light is turned off. Initially, a drug infusion occurs with every press of the active lever. Once lever-pressing behavior has been established, the number of presses to produce a drug infusion is increased. After stable compound/drug self-administration is obtained, the effect of a second compound on the drug-reinforced behavior may be evaluated. Administration of this second compound prior to the session can either potentiate, extinguish, or produce no change to the self-administrating behavior.

The following tests were carried out in order to determine the activity of the compounds of formula (I).

The affinity of the compounds of the invention for cannabinoid CB1 receptors was determined using membrane preparations of human embryonic kidney (HEK) cells in which the human cannabis CB1 receptor is transiently transfected using the Semliki Forest Virus system in conjunction with [3H]-CP-55,940 as radioligand. After incubation of a freshly prepared cell membrane preparation with the [3H]-ligand, with or without addition of compounds of the invention, separation of bound and free ligand was performed by filtration over glass-fiber filters. Radioactivity on the filter was measured by liquid scintillation counting.

The affinity of the compounds of the invention for cannabinoid CB2 receptors was determined using membrane preparations of human embryonic kidney (HEK) cells in which the human cannabis CB2 receptor is transiently transfected using the Semliki Forest virus system in conjunction with [3H]-CP-55,940 as radioligand. After incubation of a freshly prepared cell membrane preparation with the [3H]-ligand, with or without addition of compounds of the invention, separation of bound of bound and free ligand was performed by filtration over glassfiber filters. Radioactivity on the filter was measured by liquid scintillation counting.

The cannabinoid CB1 antagonistic activity of compounds of the invention was determined by functional studies using CHO cells in which human cannabinoid CB1 receptors are stably expressed (see M. Rinaldi-Carmona et. al., J. Pharmacol. Exp. Ther. 278 (1996) 871). The stable expression of the human cannabinoid receptor in cell systems was first described in Nature 1990, 346, 561-564 (CB1) and Nature 1993, 365, 61-65 (CB2) respectively. Adenylyl cyclase was stimulated using forskolin and measured by quantifying the amount of accumulated cyclic AMP. Concomitant activation of CB1 receptors by CB1 receptor agonists (e.g. CP-55,940 or (R)-WIN-55212-2) can attenuate the forskolin-induced accumulation of cAMP in a concentration dependent manner. This CB1 receptor mediated response can be antagonised by CB1 receptor antagonists such as the compounds of the invention.

The compounds of formula (I) show an excellent affinity for the CB1 receptor, determined with the experimental conditions described in Devane et. al. Mol. Pharmacol. 34 (1988) 605-613. The compounds of the present invention or their pharmaceutically acceptable salts are antagonists and selective for the CB1 receptor with affinities below $IC_{50}=2$ µM, preferably 1 nM to 100 nM. They exhibit at least a 10 fold selectivity against the CB2 receptor.

| Compound of Example | $IC_{50}$ [µM] |
|---|---|
| 19 | <2 |
| 21 | <2 |
| 41 | <2 |
| 52 | <2 |
| 54 | <2 |

-continued

| Compound of Example | $IC_{50}$ [µM] |
|---|---|
| 89 | <2 |
| 91 | <2 |
| 194 | <2 |
| 264 | <2 |
| 282 | <2 |
| 283 | <2 |
| 286 | <2 |
| 290 | <2 |
| 294 | <2 |
| 301 | <2 |

Effect of CB1 Receptor Antagonist/Inverse Agonist on CP 55,940-induced Hypothermia in NMRI Mice Animals Male NMRI mice were used in this study and were obtained from Research Consulting Company Ltd (RCC) of Füllinsdorf (Switzerland). Mice, weighing 30-31 g were used in this study. Ambient temperature is approximately 20-21° C. and relative humidity 55-65%. A 12 hours light-dark cycle is maintained in the rooms with all tests being performed during the light phase. Access to tap water and food are ad libitum.

Method

All measurements were made between 12:00 am and 5:00 pm. Mice were brought in this environment and habituated for at least two hours before the start of the experiment. They had always free access to food and water. For each dose, 8 mice were used. Rectal body temperature measurements were recorded by mean of a rectal probe (RET2 of Physitemp) and digital thermometer (Digi-sense n°8528-20 of Cole Parmer, Chicago USA). The probe was inserted about 3.5 cm in each mouse.

The body temperature was taken 15 min before administration of either Vehicle or CB1 receptor antagonist/inverse agonist. 30 or 90 min after i.p. or p.o. administration of this compound, respectively, rectal body temperature was recorded in order to evaluate any influence of the compound itself. The CB receptor agonist CP 55,940 (0.3 mg/kg) was immediately administered intravenously, then 20 min after i.v. administration of CP 55940, body temperature was again measured.

The in vivo activity of compounds of formula (1) was assessed for their ability to regulate feeding behaviour by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of compounds of formula (1) to decrease food intake, 8 animals were used in a cross-over study. Rats were individually housed in Plexiglas boxes with a grid on the floor and a paper was placed below the cage floor to collect any spillage. A food dispenser (becher) filled with a pre-weighed amount of food was presented to them for 2 h. At the end of the food intake session, rats returned to their home cage. Each rat was weighed before the start of the experiment and the amount of food consumed during this 2 h food intake session was recorded. Either various doses of test compound or vehicle was administered orally 60 min before the 2 h food intake session. A positive control Rimonabant (SR141716) was included in the experiment. An Anova analysis with repeated measures was used followed by a posthoc test Student Neumann-Keuls. *P<0.05 compared to Saline-treated rats.

Furthermore the utility of compounds of formula (1) in diseases or disorders may be demonstrated in animal disease models that have been reported in the literature. The following are examples of such animal disease models: a) reduction of sweet food intake in marmosets (Behavioural Pharm, 1998, 9, 179-181); b) reduction of sucrose and ethanol intake in mice (Psychopharm. 1997, 132, 104-106); c) increased motor activity and place conditioning in rats (Psychopharm. 1998, 135, 324-332; Psychopharmacol 2000, 151: 25-30); d) spontaneous locomotor activity in mice (J. Pharm. Exp. Ther. 1996, 277, 586-594); e) reduction in opiate self-administration in mice (Sci. 1999, 283, 401-404).

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

MS=mass spectrometry; ISP=ion spray (positive ion), corresponds to ESI (electrospray, positive ion); mp=melting point; TBTU=O-(Benzotriazol-1-yl)-N,N',N'-tetramethyluronium-tetrafluoroborate; DMF=dimethylformamide.

Example 1

Cyclohexylmethyl-5-phenyl-2-methyl-1H-pyrrole-3-carboxylic acid butylamide

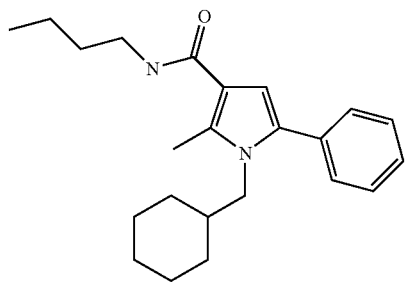

To a solution of 4.2 g of diketene in dichloromethane (70 ml) cooled at 0° C. was added over 1 hour a solution of 3.7 g of butylamine in 50 ml of dichloromethane. The reaction mixture was then stirred for one hour at 0° C. and was then allowed to stir at room temperature for another hour. The reaction mixture was concentrated in vacuo and the crude residue was partitioned in batches which were directly used in the next step.

To 2.0 g of the previous crude material in 55 ml of dimethylformamide was added 1.65 ml of cyclohexylmethylamine together with 1.4 ml of trimethyl orthoformate and the reaction mixture was stirred for 24 hours at room temperature.

3.4 ml of the previous solution was then transferred into another reaction vessel and 120 mg of 2-bromo-phenyl-ethanone was added together with 0.092 ml of 2,6-lutidine and the reaction mixture was stirred for another 24 hours at room temperature. After such time the reaction mixture was concentrated in vacuo and purified by column chromatography (50 g of SiO$_2$, n-Heptane-Ethyl acetate 0-80%) to yield 112 mg of the title compound as a light brown gum, MS (ISP) 353.4 (M+H)$^+$.

Examples 2-48 were synthesized in analogy to Example 1, using the indicated educts.

Example 2

Cyclohexylmethyl-5-(3,4-dichloro-phenyl)-2-methyl-1H-pyrrole-3-carboxylic acid butylamide

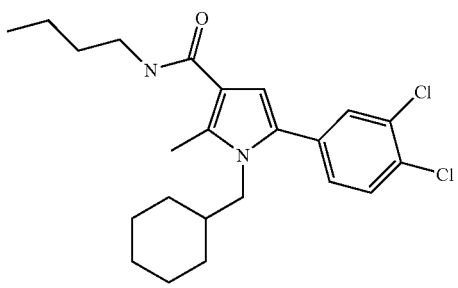

The title compound was obtained using butylamine as $R^1R^2NH$, aminoethylcyclohexane as $R^3$—$(CH_2)_m$—$NH_2$ and 2-bromo-3',4'-dichloroacetophenone, MS (ISP) 421.4 (M+H)$^+$.

Example 3

Cyclohexylmethyl-5-(4-methoxy-phenyl)-2-methyl-1H-pyrrole-3-carboxylic acid butylamide

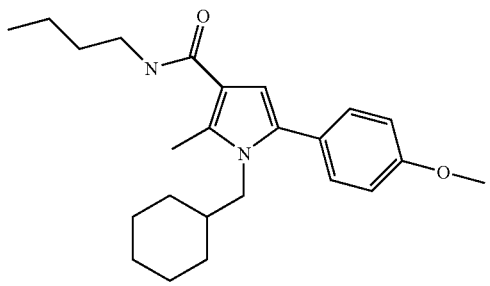

The title compound was obtained using butylamine as $R^1R^2NH$, aminoethylcyclohexane as $R^3$—$(CH_2)_m$—$NH_2$ and 2-bromo-4'-acetophenone, MS (ISP) 383.4 (M+H)$^+$.

Example 4

Cyclohexylmethyl-5-(3-methoxy-phenyl)-2-methyl-1H-pyrrole-3-carboxylic acid butylamide

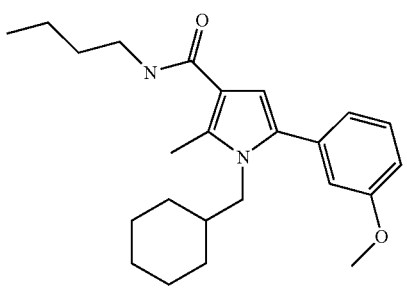

The title compound was obtained using butylamine as $R^1R^2NH$, aminoethylcyclohexane as $R^3$—$(CH_2)_m$—$NH_2$ and 2-bromo-3'-methoxyacetophenone, MS (ISP) 383.3 (M+H)$^+$.

Example 5

5-(4-Cyano-phenyl)-1-cyclohexylmethyl-2-methyl-1H-pyrrole-3-carboxylic acid butylamide

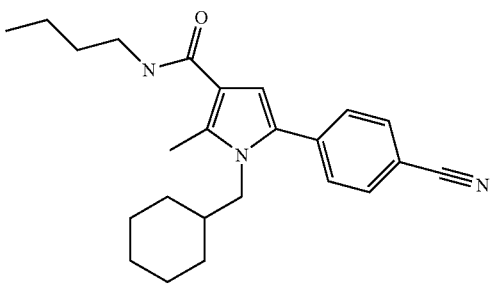

The title compound was obtained using butylamine as $R^1R^2NH$, aminoethylcyclohexane as $R^3$—$(CH_2)_m$—$NH_2$ and 2-bromo-4'cyanoacetophenone, MS (ISP) 378.4 (M+H)$^+$.

Example 6

Cyclohexylmethyl-2-methyl-5-(4-trifluoromethyl-phenyl)-1H-pyrrole-3-carboxylic acid butylamide

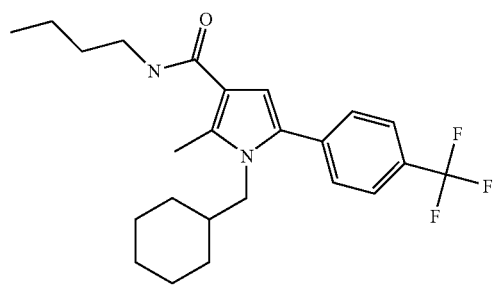

The title compound was obtained using butylamine as $R^1R^2NH$, aminoethylcyclohexane as $R^3$—$(CH_2)_m$—$NH_2$ and 2-bromo-4'-(trifluoromethyl)acetophenone, MS (ISP) 421.4 (M+H)$^+$.

Example 7

Cyclohexylmethyl-5-(3,5-di-tert-butyl-4-hydroxy-phenyl)-2-methyl-1H-pyrrole-3-carboxylic acid butylamide

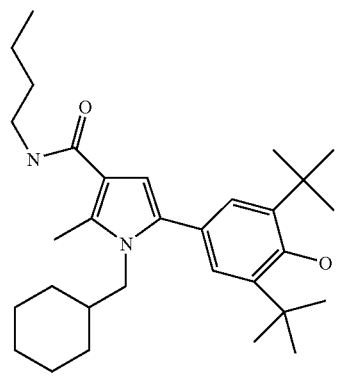

The title compound was obtained using butylamine as R¹R²NH, aminoethylcyclohexane as R³—(CH$_2$)$_m$—NH$_2$ and 2-bromo-1-(3,5-di-tert-butyl-4-hydroxy-phenyl)-ethanone.

Example 8

5-(4-Chloro-phenyl)-1-cyclohexylmethyl-2-methyl-1H-pyrrole-3-carboxylic acid butylamide

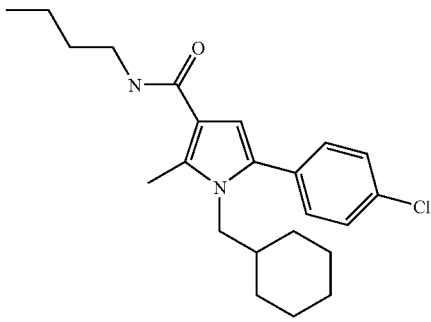

The title compound was obtained using butylamine as R¹R²NH, aminoethylcyclohexane as R³—(CH$_2$)$_m$—NH$_2$ and 2-bromo-4'-chloroacetophenone, MS (ISP) 387.3 (M+H)$^+$.

Example 9

Cyclohexylmethyl-2-methyl-5-p-tolyl-1H-pyrrole-3-carboxylic acid butylamide

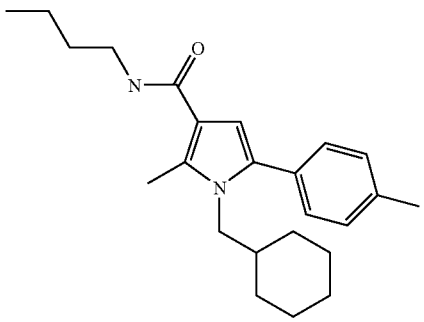

The title compound was obtained using butylamine as R¹R²NH, aminoethylcyclohexane as R³—(CH$_2$)$_m$—NH$_2$ and 2-bromo-4'-methylacetophenone, MS (ISP) 367.3 (M+H)$^+$.

Example 10

Cyclohexylmethyl-5-(2,4-dichloro-phenyl)-2-methyl-1H-pyrrole-3-carboxylic acid butylamide

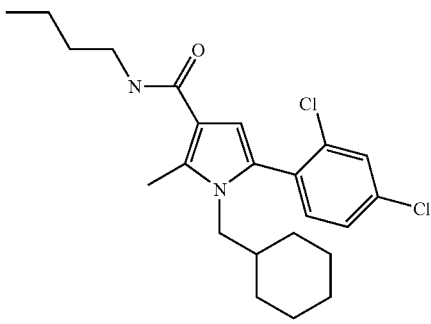

The title compound was obtained using butylamine as R¹R²NH, aminoethylcyclohexane as R³—(CH$_2$)$_m$—NH$_2$ and 2-bromo-2',4'-dichloroacetophenone, MS (ISP) 421.2 (M+H)$^+$.

Example 11

Cyclohexylmethyl-5-(2-methoxy-phenyl)-2-methyl-1H-pyrrole-3-carboxylic acid butylamide

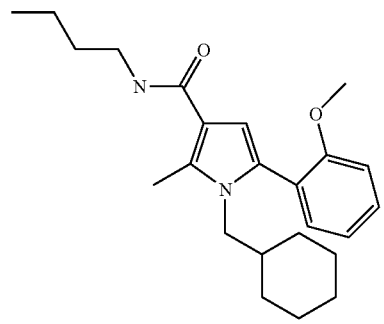

The title compound was obtained using butylamine as R¹R²NH, aminoethylcyclohexane as R³—(CH$_2$)$_m$—NH$_2$ and 2-bromo-2'-methoxyacetophenone, MS (ISP) 383.3 (M+H)$^+$.

Example 12

Cyclohexylmethyl-5-(4-fluoro-phenyl)-2-methyl-1H-pyrrole-3-carboxylic acid butylamide

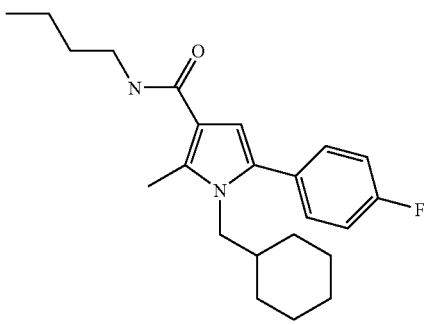

The title compound was obtained using butylamine as R¹R²NH, aminoethylcyclohexane as R³—(CH$_2$)$_m$—NH$_2$ and 2-bromo-4'-fluoroacetophenone, MS (ISP) 371.3 (M+H)$^+$.

Example 13

Cyclohexylmethyl-5-(2,4-dimethoxy-phenyl)-2-methyl-1H-pyrrole-3-carboxylic acid butylamide

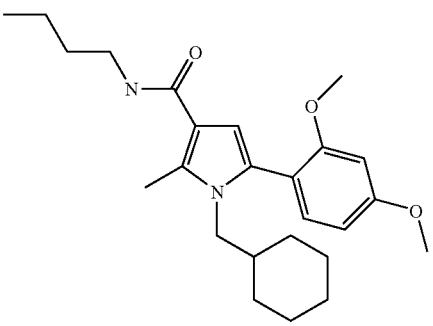

The title compound was obtained using butylamine as R¹R²NH, aminoethylcyclohexane as R³—(CH$_2$)$_m$—NH$_2$ and 2-bromo-2',4'-dimethoxyacetophenone, MS (ISP) 413.4 (M+H)$^+$.

Example 14

5-(4-Bromo-phenyl)-1-cyclohexylmethyl-2-methyl-1H-pyrrole-3-carboxylic acid butylamide

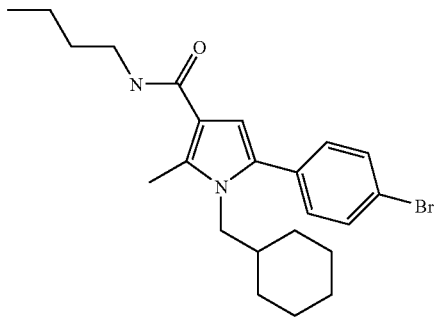

The title compound was obtained using butylamine as R¹R²NH, aminoethylcyclohexane as R³—(CH$_2$)$_m$—NH$_2$ and 2-bromo-4'-bromoacetophenone, MS (ISP) 433.3 (M+H)$^+$.

Example 15

5-(3-Cyano-phenyl)-1-cyclohexylmethyl-2-methyl-1H-pyrrole-3-carboxylic acid butylamide

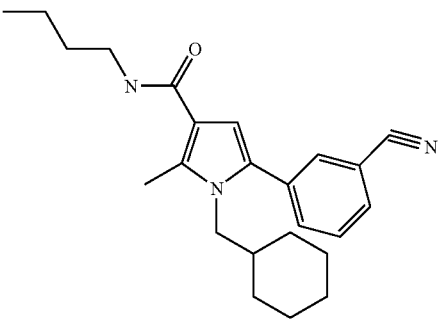

The title compound was obtained using butylamine as R¹R²NH, aminoethylcyclohexane as R³—(CH$_2$)$_m$—NH$_2$ and 2-bromo-3'-cyanoacetophenone, MS (ISP) 378.4 (M+H)$^+$.

Example 16

Cyclohexylmethyl-5-(2,4-dimethyl-phenyl)-2-methyl-1H-pyrrole-3-carboxylic acid butylamide

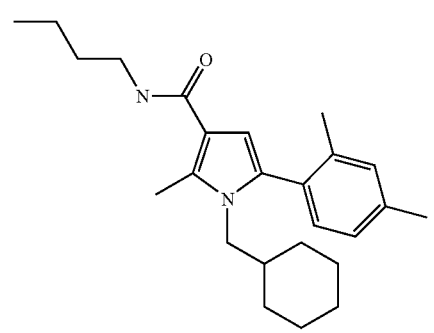

The title compound was obtained using butylamine as R¹R²NH, aminoethylcyclohexane as R³—(CH$_2$)$_m$—NH$_2$ and 2-bromo-2',4'-dimethylacetophenone, MS (ISP) 381.4 (M+H)$^+$.

Example 17

Cyclohexylmethyl-5-(4-difluoromethoxy-phenyl)-2-methyl-1H-pyrrole-3-carboxylic acid butylamide

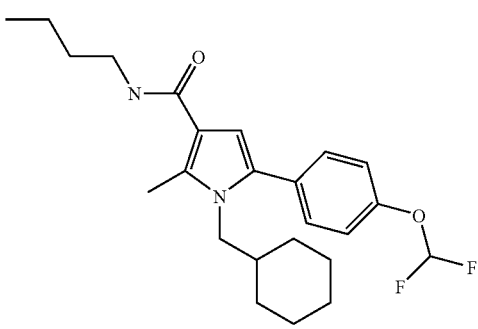

The title compound was obtained using butylamine as R¹R²NH, aminoethylcyclohexane as R³—(CH$_2$)$_m$—NH$_2$ and 2-bromo-4'-(difluoromethoxy)acetophenone, MS (ISP) 419.3 (M+H)$^+$.

Example 18

Cyclohexylmethyl-5-(3,4-dihydro-2H-benzo[b][1,4]dioxepin-7-yl)-2-methyl-1H-pyrrole-3-carboxylic acid butylamide

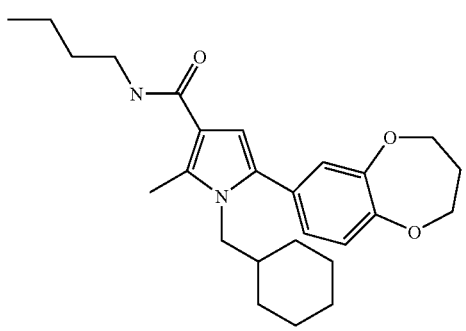

The title compound was obtained using butylamine as R¹R²NH, aminoethylcyclohexane as R³—(CH$_2$)$_m$—NH$_2$ and 2-bromo-1-(3,4-dihydro-2H-1,5-benzodioxepin-7-yl)ethan-1-one, MS (ISP) 425.3 (M+H)$^+$.

Example 19

Cyclohexylmethyl-2-methyl-5-(4-pyrrolidin-1-yl-phenyl)-1H-pyrrole-3-carboxylic acid butylamide

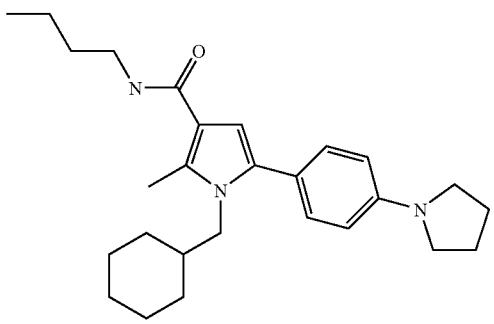

The title compound was obtained using butylamine as $R^1R^2NH$, aminoethylcyclohexane as $R^3$—$(CH_2)_m$—$NH_2$ and alpha-bromo-4-(1-pyrrolodino)acetophenone, MS (ISP) 422.4 $(M+H)^+$.

Example 20

Cyclohexylmethyl-5-(4-methanesulfonyl-phenyl)-2-methyl-1H-pyrrole-3-carboxylic acid butylamide

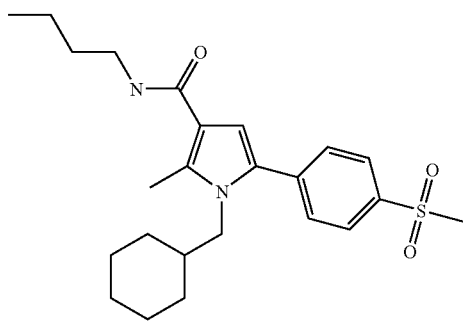

The title compound was obtained using butylamine as $R^1R^2NH$, aminoethylcyclohexane as $R^3$—$(CH_2)_m$—$NH_2$ and 2-bromo-4'-methylsulfonylacetophenone, MS (ISP) 431.4 $(M+H)^+$.

Example 21

Cyclohexylmethyl-5-(2,5-dimethoxy-phenyl)-2-methyl-1H-pyrrole-3-carboxylic acid butylamide

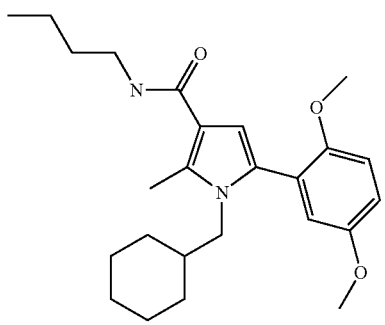

The title compound was obtained using butylamine as $R^1R^2NH$, aminoethylcyclohexane as $R^3$—$(CH_2)_m$—$NH_2$ and 2-bromo-2',5'-dimethoxyacetophenone, MS (ISP)-413.4 $(M+H)^+$

Example 22

Cyclohexylmethyl-5-(3,4-difluoro-phenyl)-2-methyl-1H-pyrrole-3-carboxylic acid butylamide

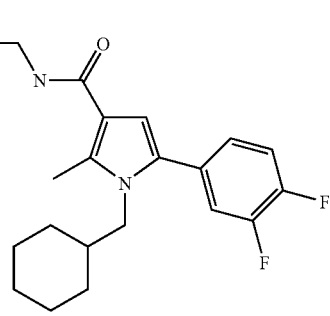

The title compound was obtained using butylamine as $R^1R^2NH$, aminoethylcyclohexane as $R^3$—$(CH_2)_m$—$NH_2$ and 2-bromo-3',4'-difluoroacetophenone, MS (ISP) 389.3 $(M+H)^+$.

Example 23

5-(3-Chloro-phenyl)-1-cyclohexylmethyl-2-methyl-1H-pyrrole-3-carboxylic acid butylamide

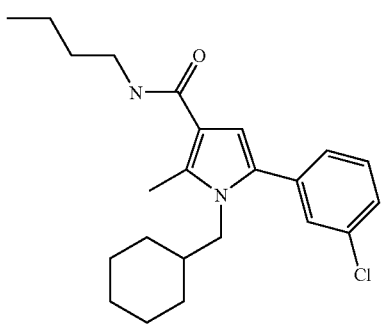

The title compound was obtained using butylamine as $R^1R^2NH$, aminoethylcyclohexane as $R^3$—$(CH_2)_m$—$NH_2$ and 2-bromo-3'chloroacetophenone, MS (ISP) 387.3 $(M+H)^+$.

Example 24

Cyclohexylmethyl-5-(4-diethylamino-phenyl)-2-methyl-1H-pyrrole-3-carboxylic acid butylamide

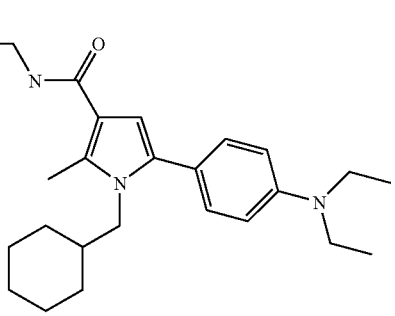

The title compound was obtained using butylamine as R¹R²NH, aminoethylcyclohexane as R³—(CH$_2$)$_m$—NH$_2$ and 2-bromo-4'-(diethylamino)acetophenone, MS (ISP) 424.4 (M+H)$^+$.

Example 25

Cyclohexylmethyl-2-methyl-5-(4-trifluoromethoxy-phenyl)-1H-pyrrole-3-carboxylic acid butylamide

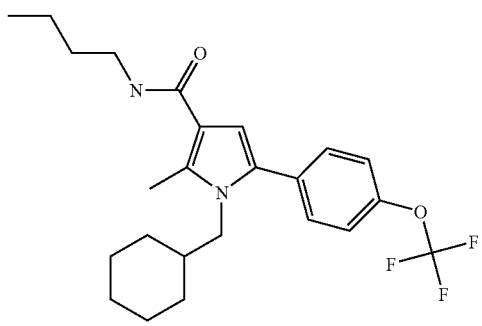

The title compound was obtained using butylamine as R¹R²NH, aminoethylcyclohexane as R³—(CH$_2$)$_m$—NH$_2$ and 2-bromo-4'-(trifluoromethoxy)acetophenone, MS (ISP) 437.3 (M+H)$^+$.

Example 26

Cyclohexylmethyl-5-(2,3-dihydro-benzo[1,4]dioxin-6-yl)-2-methyl-1H-pyrrole-3-carboxylic acid butylamide

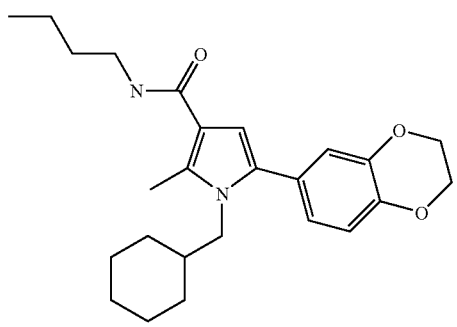

The title compound was obtained using butylamine as R¹R²NH, aminoethylcyclohexane as R³—(CH$_2$)$_m$—NH$_2$ and 2-bromo-1-(2,3-dihydro-1,4-benzodioxin-6-yl)ethan-1-one, MS (ISP) 411.3 (M+H)$^+$.

Example 27

Cyclohexylmethyl-5-(3,4-dimethoxy-phenyl)-2-methyl-1H-pyrrole-3-carboxylic acid butylamide

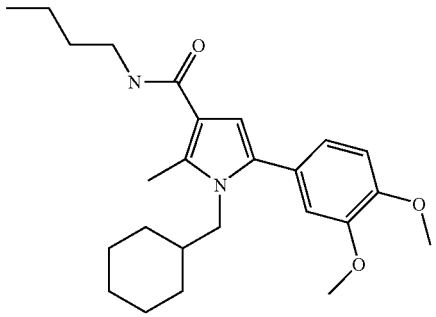

The title compound was obtained using butylamine as R¹R²NH, aminoethylcyclohexane as R³—(CH$_2$)$_m$—NH$_2$ and 2-bromo-3',4'-dimethoxyacetophenone, MS (ISP) 413.4 (M+H)$^+$.

Example 28

5-(2-Chloro-phenyl)-1-cyclohexylmethyl-2-methyl-1H-pyrrole-3-carboxylic acid butylamide

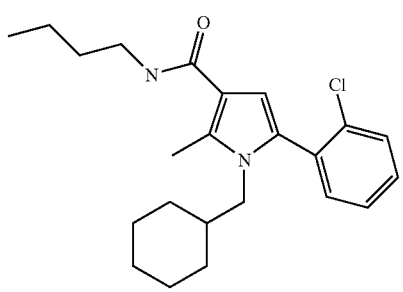

The title compound was obtained using butylamine as R¹R²NH, aminoethylcyclohexane as R³—(CH$_2$)$_m$—NH$_2$ and 2-bromo-2'-chloroacetophenone, MS (ISP) 387.3 (M+H)$^+$.

Example 29

Cyclohexylmethyl-2-methyl-5-(4-nitro-phenyl)-1H-pyrrole-3-carboxylic acid butylamide

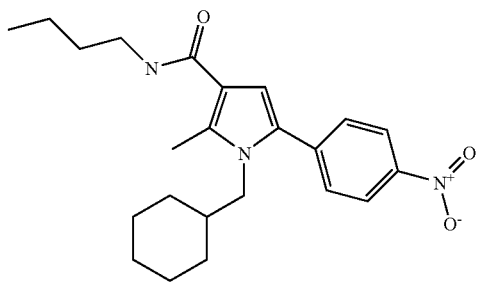

The title compound was obtained using butylamine as R¹R²NH, aminoethylcyclohexane as R³—(CH$_2$)$_m$—NH$_2$ and 2-bromo-4'-nitroacetophenone, MS (ISP) 398.3 (M+H)$^+$.

Example 30

Cyclohexylmethyl-2-methyl-5-(2-oxo-1,2,3,4-tetrahydro-quinolin-6-yl)-1H-pyrrole-3-carboxylic acid butylamide

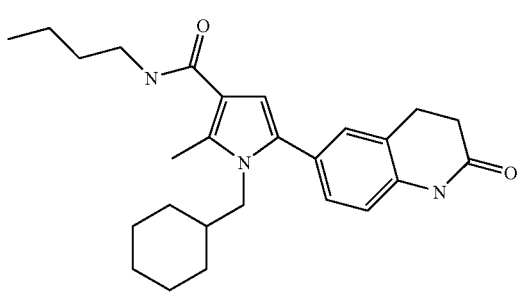

The title compound was obtained using butylamine as $R^1R^2NH$, aminoethylcyclohexane as $R^3$—$(CH_2)_m$—$NH_2$ and 6-(2-bromo-acetyl)-3,4-dihydro-1H-quinolin-2-one, MS (ISP) 422.3 (M+H)$^+$.

Example 31

Cyclohexylmethyl-2-methyl-5-naphthalen-2-yl-1H-pyrrole-3-carboxylic acid butylamide

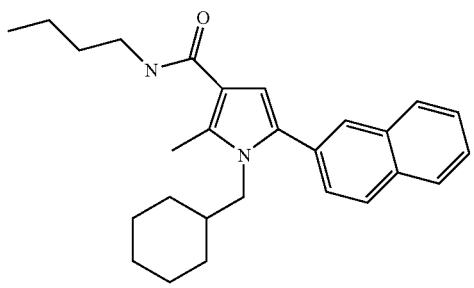

The title compound was obtained using butylamine as $R^1R^2NH$, aminoethylcyclohexane as $R^3$—$(CH_2)_m$—$NH_2$ and bromomethyl-2-naphthylketone, MS (ISP) 403.4 (M+H)$^+$.

Example 32

Cyclohexylmethyl-5-(2,5-dimethoxy-phenyl)-2-methyl-1H-pyrrole-3-carboxylic acid cyclohexylamide

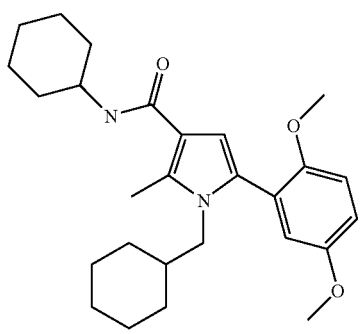

The title compound was obtained using cyclohexylamine as $R^1R^2NH$, aminoethylcyclohexane as $R^3$—$(CH_2)_m$—$NH_2$ and 2-bromo-2',5'-dimethoxyacetophenone, MS (ISP) 439.4 (M+H)$^+$.

Example 33

Cyclohexylmethyl-5-(2,5-dimethoxy-phenyl)-2-methyl-1H-pyrrole-3-carboxylic acid cyclopentylamide

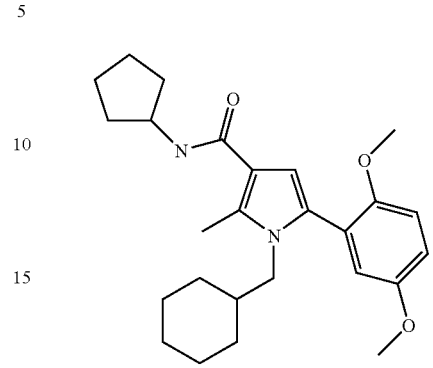

The title compound was obtained using cyclopentylamine as $R^1R^2NH$, aminoethylcyclohexane as $R^3$—$(CH_2)_m$—$NH_2$ and 2-bromo-2',5'-dimethoxyacetophenone, MS (ISP) 425.3 (M+H)$^+$.

Example 34

Cyclohexylmethyl-5-(2,5-dimethoxy-phenyl)-2-methyl-1H-pyrrole-3-carboxylic acid cyclobutylamide

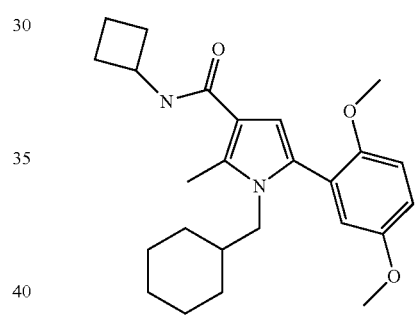

The title compound was obtained using cyclobutylamine as $R^1R^2NH$, aminoethylcyclohexane as $R^3$—$(CH_2)_m$—$NH_2$ and 2-bromo-2',5'-dimethoxyacetophenone, MS (ISP) 411.3 (M+H)$^+$.

Example 35

Cyclohexylmethyl-5-(2,5-dimethoxy-phenyl)-2-methyl-1H-pyrrole-3-carboxylic acid cyclopropylamide

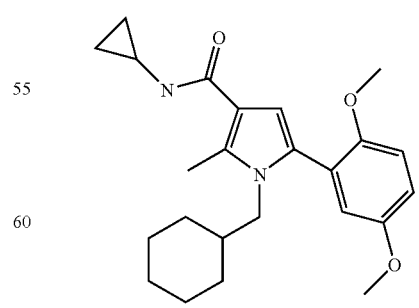

The title compound was obtained using cycloprolyamine as $R^1R^2NH$, aminoethylcyclohexane as $R^3$—$(CH_2)_m$—$NH_2$ and 2-bromo-2',5'-dimethoxyacetophenone, MS (ISP) 397.3 (M+H)$^+$.

Example 36

Cyclohexylmethyl-5-(2,5-difluoro-phenyl)-2-methyl-1H-pyrrole-3-carboxylic acid butylamide

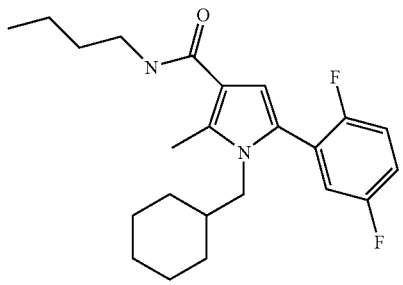

The title compound was obtained using butylamine as $R^1R^2NH$, aminoethylcyclohexane as $R^3$—$(CH_2)_m$—$NH_2$ and 2-bromo-2',5'-difluoroacetophenone, MS (ISP) 389.3 $(M+H)^+$.

Example 37

Cyclohexylmethyl-5-(4-hydroxy-3-methoxy-phenyl)-2-methyl-1H-pyrrole-3-carboxylic acid butylamide

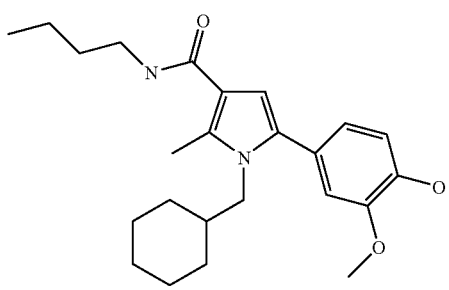

The title compound was obtained using butylamine as $R^1R^2NH$, aminoethylcyclohexane as $R^3$—$(CH_2)_m$—$NH_2$ and 2-bromo-3'methoxy-4'-hydroxyacetophenone MS (ISP) 399.4 (M+H).

Example 38

Cyclohexylmethyl-5-(3-fluoro-phenyl)-2-methyl-1H-pyrrole-3-carboxylic acid butylamide

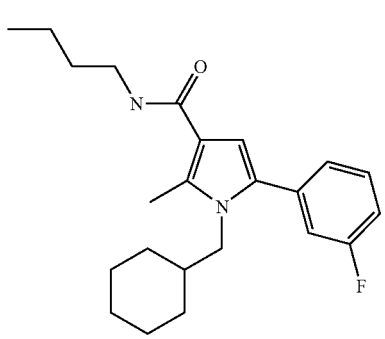

The title compound was obtained using butylamine as $R^1R^2NH$, aminoethylcyclohexane as $R^3$—$(CH_2)_m$—$NH_2$ and 2-bromo-3'-fluoroacetophenone, MS (ISP) 371.3 $(M+H)^+$.

Example 39

5-Benzo[1,3]dioxol-5-yl-1-cyclohexylmethyl-2-methyl-1H-pyrrole-3-carboxylic acid butylamide

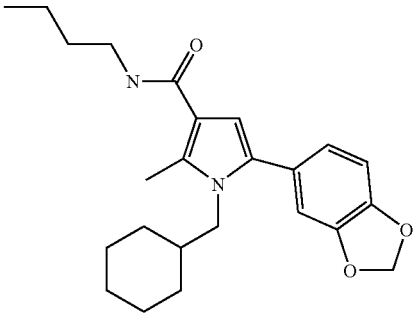

The title compound was obtained using butylamine as $R^1R^2NH$, aminoethylcyclohexane as $R^3$—$(CH_2)_m$—$NH_2$ and 1-(1,3-bentodioxol-5-yl)-2-bromoethan-1-one, MS (ISP) 397.3 $(M+H)^+$.

Example 40

Cyclohexylmethyl-5-(2,5-dichloro-phenyl)-2-methyl-1H-pyrrole-3-carboxylic acid butylamide

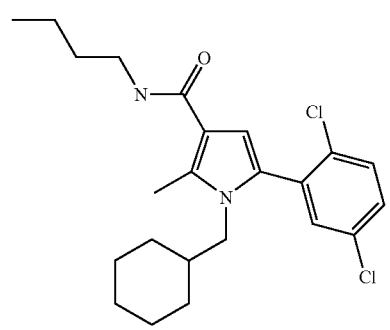

The title compound was obtained using butylamine as $R^1R^2NH$, aminoethylcyclohexane as $R^3$—$(CH_2)_m$—$NH_2$ and 2-bromo-2',5'-dichloroacetophenone MS (ISP) 421.2 $(M+H)^+$.

Example 41

5-(3,5-Bis-trifluoromethyl-phenyl)-1-cyclohexylmethyl-2-methyl-1H-pyrrole-3-carboxylic acid butylamide

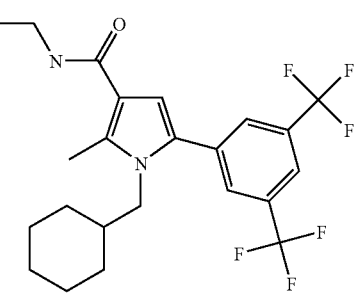

The title compound was obtained using butylamine as R¹R²NH, aminoethylcyclohexane as R³—(CH₂)ₘ—NH₂ and 2-bromo-3',5'-di(trifluoromethyl)acetophenone MS (ISP) 489.3 (M+H)⁺.

Example 42
5-(3,5-Bis-trifluoromethyl-phenyl)-1-cyclohexylmethyl-2-methyl-1H-pyrrole-3-carboxylic acid cyclohexylamide

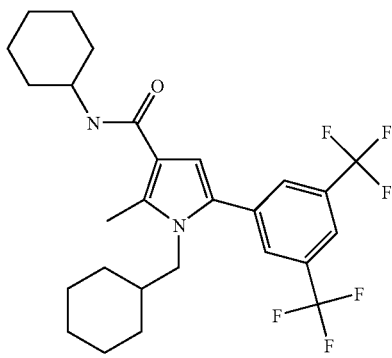

The title compound was obtained using cyclohexylamine as R¹R²NH, aminoethylcyclohexane as R³—(CH₂)ₘ—NH₂ and 2-bromo-3',5'-di(trifluoromethyl)acetophenone, MS (ISP) 515.3 (M+H)⁺.

Example 43
Cyclohexylmethyl-2-methyl-5-(4-pyrrolidin-1-yl-phenyl)-1H-pyrrole-3-carboxylic acid cyclohexylamide

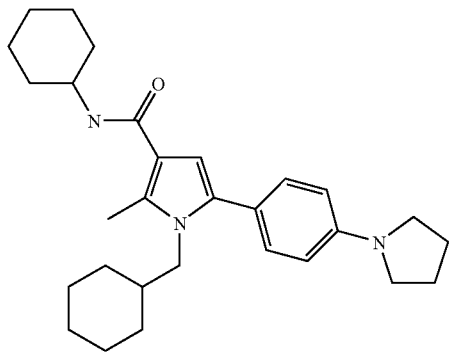

The title compound was obtained using cyclohexylamine as R¹R²NH, aminoethylcyclohexane as R³—(CH₂)ₘ—NH₂ and, MS (ISP) 448.4 (M+H)⁺.

Example 44
Cyclohexylmethyl-5-(2,5-dimethoxy-phenyl)-2-methyl-1H-pyrrole-3-carboxylic acid butyl-methyl-amide

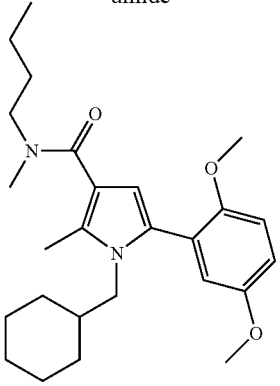

The title compound was obtained using N-methylbutylamine as R¹R²NH, aminoethylcyclohexane as R³—(CH₂)ₘ—NH₂ and 2-bromo-2',5'-dimethoxyacetophenone, MS (ISP) 427.3 (M+H)⁺.

Example 45
(R)-1-Cyclohexylmethyl-5-(2,5-dimethoxy-phenyl)-2-methyl-1H-pyrrole-3-carboxylic acid sec-butylamide

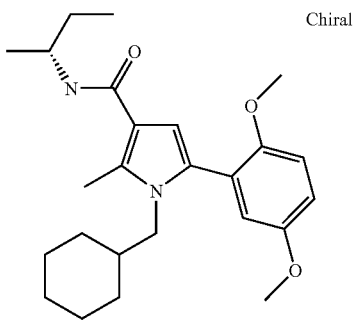

The title compound was obtained using (R)-(−)-2-Aminobutane as R¹R²NH, aminoethylcyclohexane as R³—(CH₂)ₘ—NH₂ and 2-bromo-2',5'-dimethoxyacetophenone, MS (ISP) 413.3 (M+H)⁺.

Example 46
5-(3,5-Bis-trifluoromethyl-phenyl)-1-(4-methoxybenzyl)-2-methyl-1H-pyrrole-3-carboxylic acid cyclohexylamide

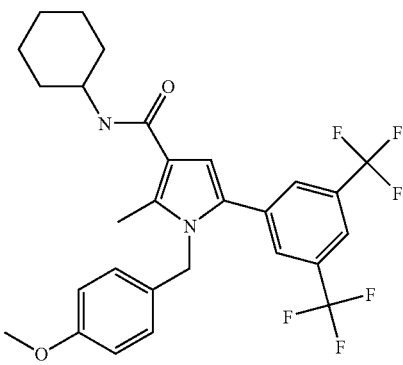

The title compound was obtained using cyclohexylamine as R¹R²NH, 4-methoxybenzylamine as R³—(CH₂)ₘ—NH₂ and 2-bromo-3',5'-di(trifluoromethyl)-acetophenone, MS (ISP) 539.5 (M+H)⁺.

Example 47

Cyclohexylmethyl-5-(2,5-dimethoxy-phenyl)-2-methyl-1H-pyrrole-3-carboxylic acid piperidin-1-ylamide

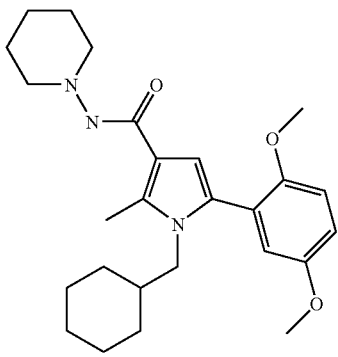

The title compound was obtained using 1-aminopiperidine as $R^1R^2NH$, aminomethylcyclohexane as $R^3$—$(CH_2)_m$—$NH_2$ and 2-bromo-2',5'-dimethoxyacetophenone, MS (ISP) 440.5 (M+H)$^+$.

Example 48

Cyclohexylmethyl-2-methyl-5-pyridin-2-yl-1H-pyrrole-3-carboxylic acid butylamide

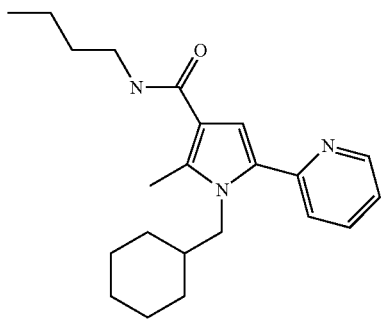

The title compound was obtained using butylamine as $R^1R^2NH$, aminomethylcyclohexane as $R^3$—$(CH_2)_m$—$NH_2$ and 2-(bromoacetyl)pyridine, MS (ISP) 354.3 (M+H)$^+$.

Example 49

Cyclohexylmethyl-2-(2-chloro-phenyl)-5-methyl-1H-imidazole-4-carboxylic acid butylamide Preparation of 2-(2-Chloro-phenyl)-5-methyl-1H-imidazole-4-carboxylic acid ethyl ester To a solution of 8.5 g of ethyl 2-oximinoacetoacetate in acetonitrile (100 ml) was added 7.5 ml of 2-chlorobenzylamine. The reaction mixture was then refluxed for 4 hours under argon atmosphere. After such time the reaction mixture was then concentrated in vacuo and the residue was triturated with warm ethylacetate for 10 minutes. After allowing to cool down to room temperature the solid was filtered and dried in vacuo to yield 11.3 g of a white powder, MS (ISP) 265.1 (M+H)$^+$.

Preparation of 2-(2-Chloro-phenyl)-5-methyl-1H-imidazole-4-carboxylic acid

To 11.2 g of 2-(2-chloro-phenyl)-5-methyl-1H-imidazole-4-carboxylic acid ethyl ester in 150 ml of ethanol was added 80 ml of a 2N—NaOH solution and the reaction mixture was stirred at 95° C. for 17 hours. After such time ethanol was removed in vacuo and the remaining aqueous solution was treated with a 2N HCl solution until obtaining pH=3. The precipitate was filtered and dried under high vacuum to yield 9.0 g of a pale yellow powder.

Preparation of 2-(2-Chloro-phenyl)-5-methyl-1H-imidazole-4-carboxylic acid piperidin-1-ylamide To 1 g of 2-(2-chloro-phenyl)-5-methyl-1H-imidazole-4-carboxylic acid in 10 ml of DMF was added 1.36 g of TBTU and 3.6 ml of Hünigs' base and the reaction mixture was stirred for 1 minute. Then 0.46 ml of 1-aminopiperidin was added and the reaction mixture was stirred for 1.5 hour at room temperature. After such time the reaction mixture was poured onto 200 ml of water and extracted with ethyl acetate (2×200 ml). The combined organic extracts were then washed with water (2×100 ml) and brine (50 ml), dried (MgSO$_4$) and concentrated in vacuo to yield an oil which crystallized on standing. The residue was then triturated with heptane, the solid was filtered and dried to yield 1.12 g of the title compound, MS (ISP) 319.0 (M+H)$^+$.

Preparation of 1-Cyclohexylmethyl-2-(2-chloro-phenyl)-5-methyl-1H-imidazole-4-carboxylic acid butylamide To a suspension of 90 mg of 2-(2-chloro-phenyl)-5-methyl-1H-imidazole-4-carboxylic acid piperidin-1-ylamide in 4 ml of acetonitrile was added 35 mg of potassium tert-butylate and the reaction mixture was stirred at room temperature for 2 minutes. After such time, 0.04 ml of (bromomethyl)cyclohexane was added and the reaction mixture was stirred at 80° C. for 28 hours under argon atmosphere. The reaction mixture was then concentrated in vacuo and purified by column chromatography (SiO$_2$, Heptane/EtOAC:1/1) to give 64 mg of the title compound as a pale yellow solid, MS (ISP) 415.3 (M+H)$^+$.

Examples 50-66 were synthesized in analogy to example 49, using the indicated educts.

Example 50

1-(4-Chloro-benzyl)-2-(4-methoxy-phenyl)-5-methyl-1H-imidazole-4-carboxylic acid butylamide

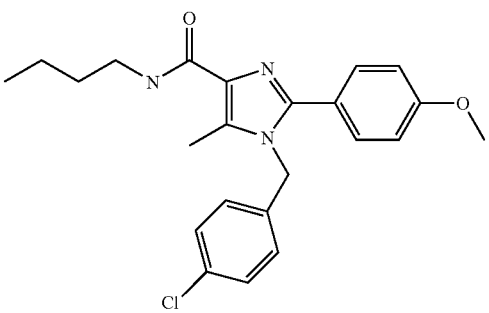

The title compound was obtained using 4-Methoxy benzylamine as $R^4$—$CH_2$—$NH_2$, Butylamine as $R^1R^2NH$ and 4-Chlorobenzyl chloride as $R^3$—$(CH_2)_m$—Br, MS (ISP) 412.3 (M+H)$^+$.

Example 51

Cyclohexylmethyl-2-(4-methoxy-phenyl)-5-methyl-1H-imidazole-4-carboxylic acid butylamide

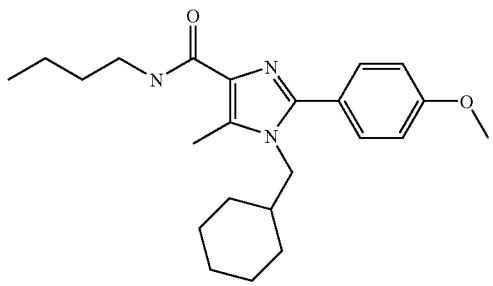

The title compound was obtained using 4-Methoxy benzylamine as $R^4$—$CH_2$—$NH_2$, Butylamine as $R^1R^2NH$ and (Bromomethyl)cyclohexane as $R^3$—$(CH_2)_m$—Br, MS (ISP) 384.3 (M+H)$^+$.

Example 52

Cyclohexylmethyl-2-(2-methoxy-phenyl)-5-methyl-1H-imidazole-4-carboxylic acid butylamide

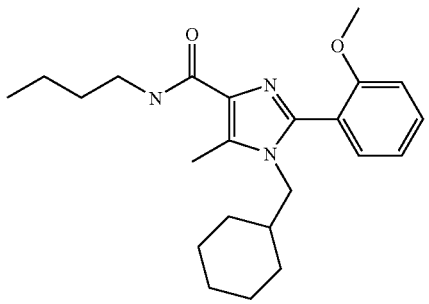

The title compound was obtained using 2-Methoxy benzylamine as $R^4$—$CH_2$—$NH_2$, Butylamine as $R^1R^2NH$ and (Bromomethyl)cyclohexane as $R^3$—$(CH_2)_m$—Br, MS (ISP) 384.3 (M+H)$^+$.

Example 53

1-(4-Chloro-benzyl)-2-(2-methoxy-phenyl)-5-methyl-1H-imidazole-4-carboxylic acid butylamide

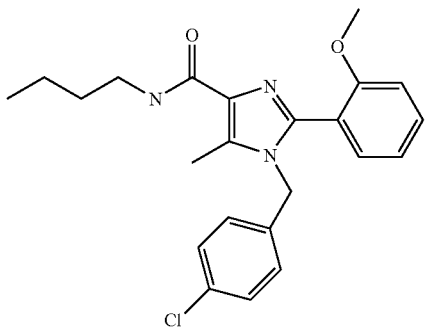

The title compound was obtained using 2-Methoxy benzylamine as $R^4$—$CH_2$—$NH_2$, Butylamine as $R^1R^2NH$ and 4-Chlorobenzyl chloride as $R^3$—$(CH_2)_m$—Br, MS (ISP) 412.3 (M+H)$^+$.

Example 54

Cyclohexylmethyl-2-(2-methoxy-phenyl)-5-methyl-1H-imidazole-4-carboxylic acid piperidin-1-ylamide

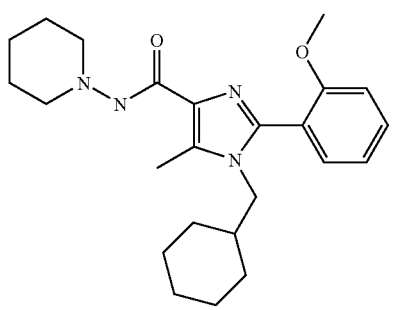

The title compound was obtained using 2-Methoxy benzylamine as $R^4$—$CH_2$—$NH_2$, 1-Aminopiperidine as $R^1R^2NH$ and (Bromomethyl)cyclohexane as $R^3$—$(CH_2)_m$—Br, MS (ISP) 411.4 (M+H)$^+$.

Example 55

Cyclopropylmethyl-2-(2-methoxy-phenyl)-5-methyl-1H-imidazole-4-carboxylic acid butylamide

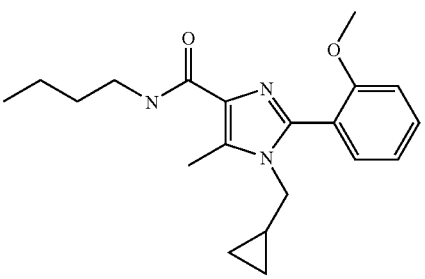

The title compound was obtained using 2-Methoxy benzylamine as $R^4$—$CH_2$—$NH_2$, Butylamine as $R^1R^2NH$ and Bromomethyl cyclopropane as $R^3$—$(CH_2)_m$—Br, MS (ISP) 342.2 (M+H)$^+$.

Example 56

1-(3-Chloro-benzyl)-2-(2-methoxy-phenyl)-5-methyl-1H-imidazole-4-carboxylic acid piperidin-1-ylamide

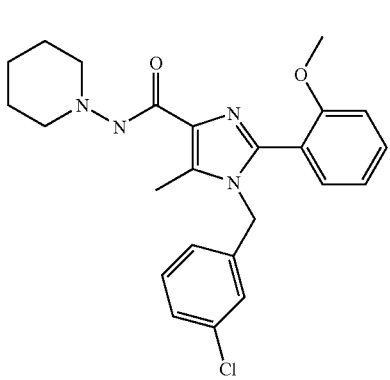

The title compound was obtained using 2-Methoxy benzylamine as $R^4$—$CH_2$—$NH_2$, 1-Aminopiperidine as $R^1R^2NH$ and 3-Chlorobenzylchloride as $R^3$—$(CH_2)_m$—Br, MS (ISP) 439.2 (M+H)$^+$.

Example 57

1-(2-Cyclohexyl-ethyl)-2-(2-methoxy-phenyl)-5-methyl-1H-imidazole-4-carboxylic acid piperidin-1-ylamide

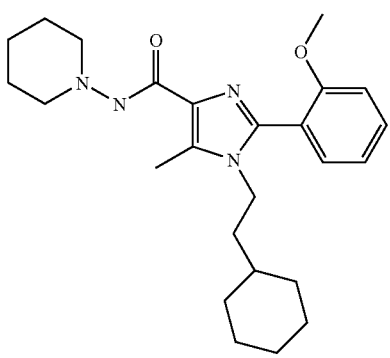

The title compound was obtained using 2-Methoxy benzylamine as $R^4$—$CH_2$—$NH_2$, 1-Aminopiperidine as $R^1R^2NH$ and (Bromoethyl)cyclohexane as $R^3$—$(CH_2)_m$—Br, MS (ISP) 425.3 (M+H)$^+$.

Example 58

1-(2-Cyclohexyl-ethyl)-2-(2-methoxy-phenyl)-5-methyl-1H-imidazole-4-carboxylic acid butylamide

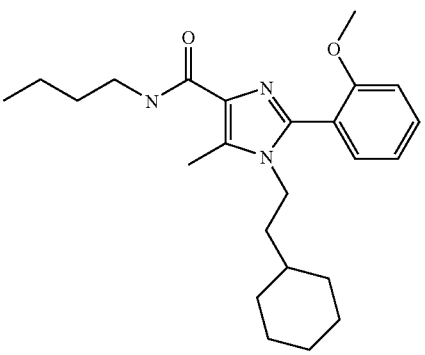

The title compound was obtained using 2-Methoxy benzylamine as $R^4$—$CH_2$—$NH_2$, Butylamine as $R^1R^2NH$ and (Bromoethyl)cyclohexane as $R^3$—$(CH_2)_m$—Br, MS (ISP) 398.3 (M+H)$^+$.

Example 59

2-(2-Chloro-phenyl)-1-cyclohexylmethyl-5-methyl-1H-imidazole-4-carboxylic acid butylamide

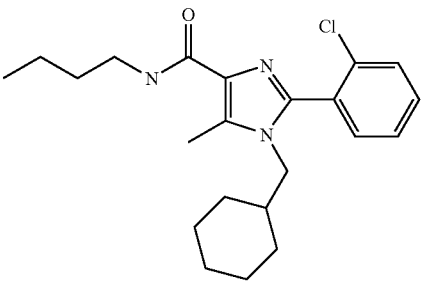

The title compound was obtained using 2-Chloro benzylamine as $R^4$—$CH_2$—$NH_2$, Butylamine as $R^1R^2NH$ and (Bromomethyl)cyclohexane as $R^3$—$(CH_2)_m$—Br, MS (ISP) 388.2 (M+H)$^+$.

Example 60

2-(2-Chloro-phenyl)-1-cyclopropylmethyl-5-methyl-1H-imidazole-4-carboxylic acid butylamide

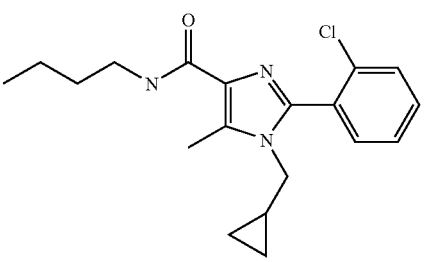

The title compound was obtained using 2-Chloro benzylamine as $R^4$—$CH_2$—$NH_2$, Butylamine as $R^1R^2NH$ and Bromomethyl cyclopropane as $R^3$—$(CH_2)_m$—Br, MS (ISP) 346.1 $(M+H)^+$.

Example 61

2-(2-Chloro-phenyl)-1-cyclopropylmethyl-5-methyl-1H-imidazole-4-carboxylic acid piperidin-1-ylamide

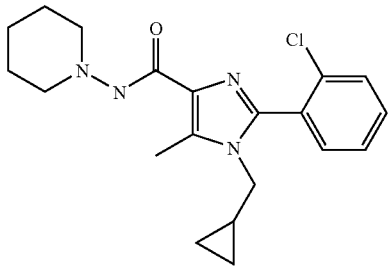

The title compound was obtained using 2-Chloro benzylamine as $R^4$—$CH_2$—$NH_2$, 1-Aminopiperidine as $R^1R^2NH$ and Bromomethyl cyclopropane as $R^3$—$(CH_2)_m$—Br, MS (ISP) 373.2 $(M+H)^+$.

Example 62

2-(2-Chloro-phenyl)-1-cyclohexylmethyl-5-methyl-1H-imidazole-4-carboxylic acid piperidin-1-ylamide

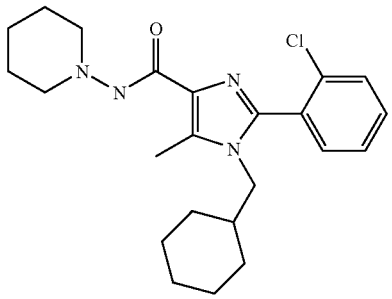

The title compound was obtained using 2-Chloro benzylamine as $R^4$—$CH_2$—$NH_2$, 1-Aminopiperidine as $R^1R^2NH$ and (Bromomethyl)cyclohexane as $R^3$—$(CH_2)_m$—Br, MS (ISP) 415.3 $(M+H)^+$.

Example 63

2-(2-Chloro-phenyl)-1-(2-cyclohexyl-ethyl)-5-methyl-1H-imidazole-4-carboxylic acid piperidin-1-ylamide

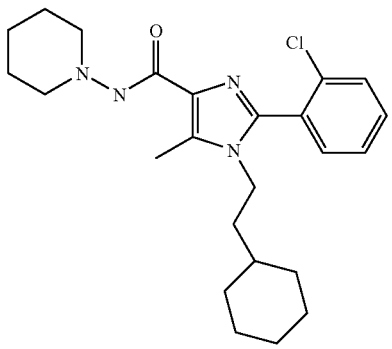

The title compound was obtained using 2-Chloro benzylamine as $R^4$—$CH_2$—$NH_2$, 1-Aminopiperidine as $R^1R^2NH$ and (Bromoethyl)cyclohexane as $R^3$—$(CH_2)_m$—Br, MS (ISP) 429.4 $(M+H)^+$.

Example 64

1-(2-Chloro-benzyl)-2-(2-chloro-phenyl)-5-methyl-1H-imidazole-4-carboxylic acid piperidin-1-ylamide

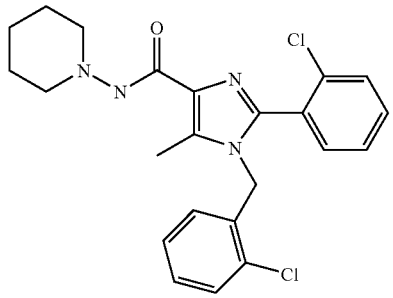

The title compound was obtained using 2-Chloro benzylamine as $R^4$—$CH_2$—$NH_2$, 1-Aminopiperidine as $R^1R^2NH$ and 2-Chlorobenzylbromide as $R^3$—$(CH_2)_m$—Br, MS (ISP) 443.3 $(M+H)^+$.

Example 65

2-(2-Chloro-phenyl)-1-(2,4-dichloro-benzyl)-5-methyl-1H-imidazole-4-carboxylic acid piperidin-1-ylamide

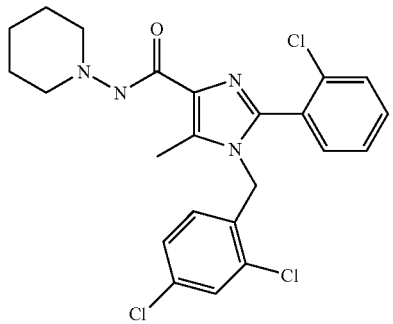

The title compound was obtained using 2-Chloro benzylamine as $R^4$—$CH_2$—$NH_2$, 1-Aminopiperidine as $R^1R^2NH$ and 2,4-Dichlorobenzylchlorid as $R^3$—$(CH_2)_m$—Br, MS (ISP) 477.2 $(M+H)^+$.

Example 66

2-(2-Chloro-phenyl)-1-(2-cyclohexyl-ethyl)-5-methyl-1H-imidazole-4-carboxylic acid butylamide

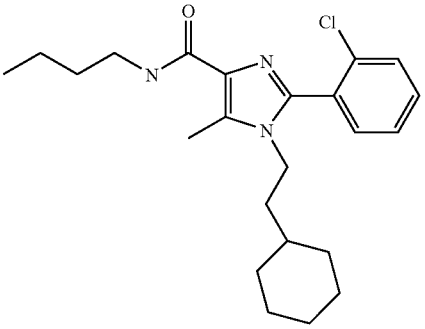

The title compound was obtained using 2-Chloro benzylamine as $R^4$—$CH_2$—$NH_2$, Butylamine as $R^1R^2NH$ and (Bromoethyl)cyclohexane as $R^3$—$(CH_2)_m$—Br, MS (ISP) 402.4 $(M+H)^+$.

Example 67

Benzyl-5-(3,5-bis-trifluoromethyl-phenyl)-2-methyl-1H-pyrrole-3-carboxylic acid cyclohexylamide

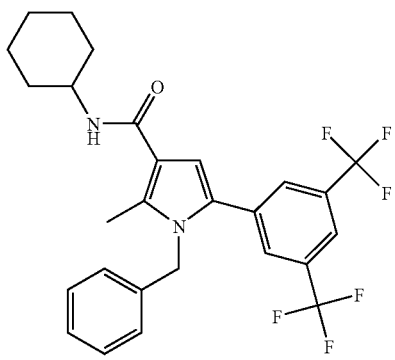

The title compound was synthesized in analogy to Example 1, using cyclohexylamine as $R^1R^2NH$, benzylamine as $R^3$—$(CH_2)_m$—$NH_2$ and 1-(3,5-bis-trifluoromethyl-phenyl)-2-bromo-ethanone, MS (ISP) 509.4 $(M+H)^+$.

Example 68

Cyclohexylmethyl-5-(2,5-dimethoxy-phenyl)-2-methyl-1H-pyrrole-3-carboxylic acid (3-hydroxy-propyl)-amide

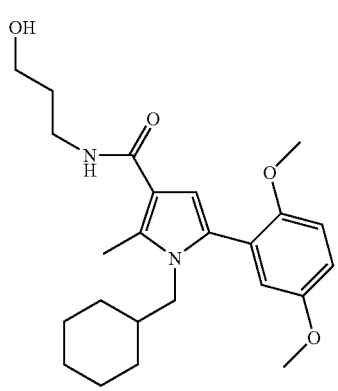

Preparation of 2-[2-(2,5-Dimethoxy-phenyl)-2-oxo-ethyl]-3-oxo-butyric acid methyl ester To a solution of 3 g of 3-oxo-butyric acid methyl ester in THF (60 ml) and 5.2 ml of a solution of sodium methoxide (5.4 M in methanol) was added over 15 minutes a solution of 7 g of 2-bromo-1-(2,5-dimethoxy-phenyl)-ethanone in 30 ml of THF. The reaction mixture was allowed to stir at room temperature for 16 hours, during which time a precipitation occurred. The reaction mixture was then diluted in diethyl ether and washed several times with water. The organic phase was then dried with sodium sulfate and concentrated in vacuo. The residue was then triturated with isopropyl ether and filtered to give 6.3 g of the title compound. MS (ISP) 295.1 $(M+H)^+$.

Preparation of 1-cyclohexylmethyl-5-(2,5-dimethoxy-phenyl)-2-methyl-1H-pyrrole-3-carboxylic acid methyl ester To a solution of 2 g of -[2-(2,5-Dimethoxy-phenyl)-2-oxo-ethyl]-3-oxo-butyric acid methyl ester in methanol was added 0.88 ml of cyclohexanemethylamine and 40 mg of p-toluene sulfonic acid. The reaction mixture was then heated at reflux for 2 days. After such time the reaction mixture was allowed to cool to room temperature before being concentrated in vacuo and purified by column chromatography to give 2.3 g of the title compound; MS (ISP) 372.2 $(M+H)^+$.

Preparation of 1-cyclohexylmethyl-5-(2,5-dimethoxy-phenyl)-2-methyl-1H-pyrrole-3-carboxylic acid To a solution of 2.3 g of 1-cyclohexylmethyl-5-(2,5-dimethoxy-phenyl)-2-methyl-1H-pyrrole-3-carboxylic acid methyl ester in dioxane (50 ml) and water (50 ml) was added 18.8 ml of a 1N solution of sodium hydroxide. The reaction mixture was heated at reflux for 16 hours. After such time the reaction mixture was allowed to cool down to room temperature before being neutralized with 18.8 ml of a 1N solution of hydrochloride acid. Dioxane was distilled off and the precipitate was then filtered and washed with water to give 2.1 g of the title compound; MS (ISP) 356.3 (M–H).

Preparation of 1-Cyclohexylmethyl-5-(2,5-dimethoxy-phenyl)-2-methyl-1H-pyrrole-3-carboxylic acid (3-hydroxy-propyl)-amide The coupling reaction between 1-cyclohexylmethyl-5-(2,5-dimethoxy-phenyl)-2-methyl-1H-pyrrole-3-carboxylic acid and 3-amino-propan-1-ol was similar to the reaction exemplified in the synthesis of Example 49 to give 1-cyclohexylmethyl-5-(2,5-dimethoxy-phenyl)-2-methyl-1H-pyrrole-3-carboxylic acid (3-hydroxy-propyl)-amide; MS (ISP) 415.3 $(M+H)^+$.

Example 69

Cyclohexylmethyl-5-(2,5-dimethoxy-phenyl)-2-methyl-1H-pyrrole-3-carboxylic acid cyclopropylmethyl-amide

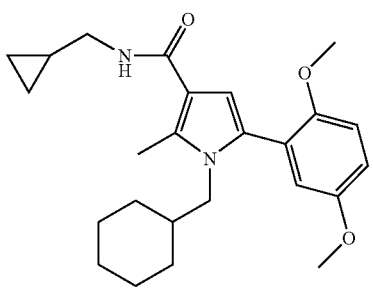

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as R3-(CH2)m-NH2 and c-cyclopropyl-methylamine as R¹R²NH, MS (ISP) 411.4 (M+H)⁺.

Example 70

Cyclohexylmethyl-5-(2,5-dimethoxy-phenyl)-2-methyl-1H-pyrrole-3-carboxylic acid morpholin-4-ylamide

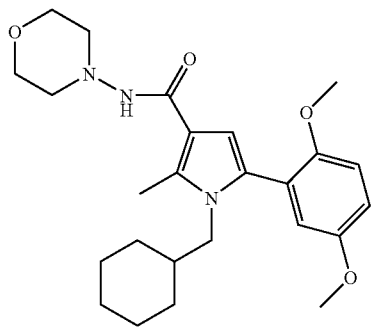

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and morpholin-4-ylamine as R¹R²NH, MS (ISP) 442.4 (M+H)⁺.

Example 71

Cyclohexylmethyl-5-(2,5-dimethoxy-phenyl)-2-methyl-1H-pyrrole-3-carboxylic acid (furan-2-ylmethyl)-amide

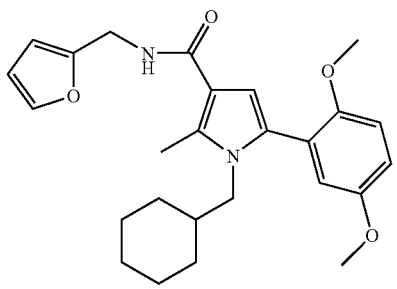

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and furan-2-yl-methylamine as R¹R²NH, MS (ISP) 437.4 (M+H)⁺.

Example 72

Cyclohexylmethyl-5-(2,5-dimethoxy-phenyl)-2-methyl-1H-pyrrole-3-carboxylic acid (3-methyl-thiophen-2-ylmethyl)-amide

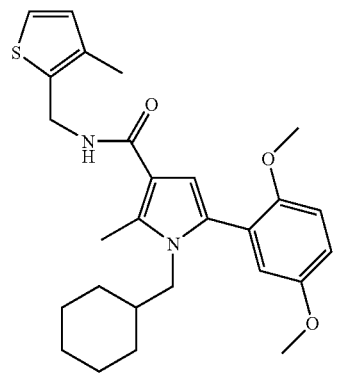

The title compound was synthesized in analogy to Example 68, using 3-oxo-butyric acid methyl ester as compound of formula R, 2-Bromo-1-(2,5-dimethoxy-phenyl)-ethanone a s compound of formula S, c-cyclohexyl-methylamine as $R^3$—$(CH_2)_m$—$NH_2$ and C-(3-Methyl-thiophen-2-yl)-methylamine as R¹R²NH, MS (ISP) 467.3 (M+H)⁺.

Example 73

Cyclohexylmethyl-5-(2,5-dimethoxy-phenyl)-2-methyl-1H-pyrrole-3-carboxylic acid (1-ethyl-pyrrolidin-2-ylmethyl)-amide

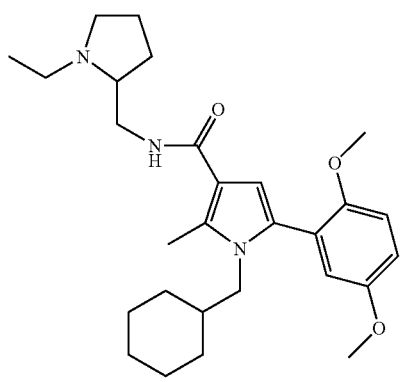

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and C-(1-ethyl-pyrrolidin-2-yl)-methylamine as R¹R²NH, MS (ISP) 468.2 (M+H)⁺.

Example 74

Cyclohexylmethyl-5-(2,5-dimethoxy-phenyl)-2-methyl-1H-pyrrole-3-carboxylic acid (3,3,3-trifluoropropyl)-amide

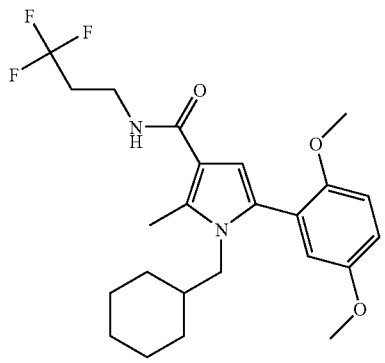

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 3,3,3-trifluoropropylamine as $R^1R^2NH$, MS (ISP) 453.1 $(M+H)^+$.

Example 75
(S)-1-Cyclohexylmethyl-5-(2,5-dimethoxy-phenyl)-2-methyl-1H-pyrrole-3-carboxylic acid sec-butylamide

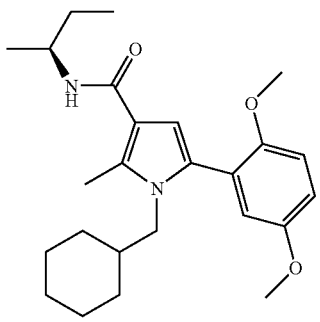

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and (S)-sec-butylamine as $R^1R^2NH$, MS (ISP) 413.3 $(M+H)^+$.

Example 76
2-(5-Chloro-2-methoxy-phenyl)-1-cyclohexylmethyl-5-methyl-1H-imidazole-4-carboxylic acid butylamide

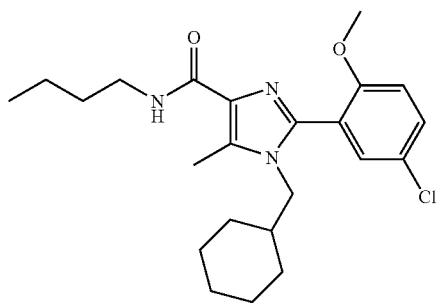

The title compound was synthesized in analogy to Example 49, using 2-methoxy-5-chloro benzylamine as $R^4$—$CH_2$—$NH_2$, butylamine as $R^1R^2NH$ and (bromomethyl)cyclohexane as $R^3$—$(CH_2)_m$—Br, MS (ISP) 418.2 $(M+H)^+$.

Example 77

2-(5-Chloro-2-methoxy-phenyl)-1-(2-cyclohexylethyl)-5-methyl-1H-imidazole-4-carboxylic acid butylamide

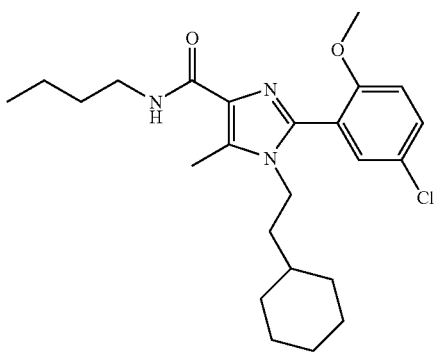

The title compound was synthesized in analogy to Example 49, using 2-methoxy-5-chloro benzylamine as $R^4$—$CH_2$—$NH_2$, butylamine as $R^1R^2NH$ and (bromoethyl)cyclohexane as $R^3$—$(CH_2)_m$—Br, MS (ISP) 432.3 $(M+H)^+$.

Example 78

2-(5-Chloro-2-methoxy-phenyl)-1-(2-cyclohexylethyl)-5-methyl-1H-imidazole-4-carboxylic acid cyclohexylamide

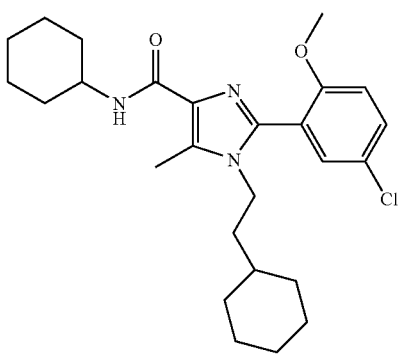

The title compound was synthesized in analogy to Example 49, using 2-methoxy-5-chloro benzylamine as $R^4$—$CH_2$—$NH_2$, cyclohexylamine as $R^1R^2NH$ and (bromoethyl)cyclohexane as $R^3$—$(CH_2)_m$—Br, MS (ISP) 472.3 $(M+H)^+$.

Example 79

Cyclohexylmethyl-2-(2-methoxy-phenyl)-5-methyl-1H-imidazole-4-carboxylic acid cyclohexylamide

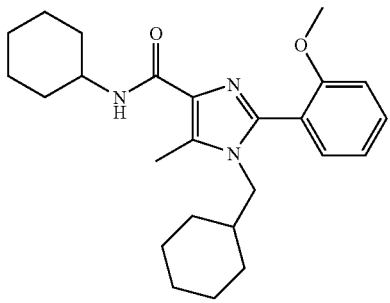

The title compound was synthesized in analogy to Example 49, using 2-methoxy-5-chloro benzylamine as $R^4$—$CH_2$—$NH_2$, cyclohexylamine as $R^1R^2NH$ and (bromomethyl) cyclohexane as $R^3$—$(CH_2)_m$—Br, MS (ISP) 410.5 $(M+H)^+$.

Example 80

1-(2-Cyclohexyl-ethyl)-2-(2-methoxy-phenyl)-5-methyl-1H-imidazole-4-carboxylic acid cyclohexylamide

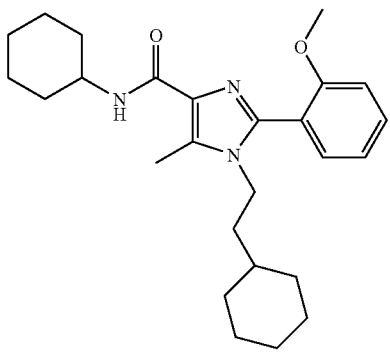

The title compound was synthesized in analogy to Example 49, using 2-methoxy benzylamine as $R^4$—$CH_2$—$NH_2$, cyclohexylamine as $R^1R^2NH$ and (bromoethyl)cyclohexane as $R^3$—$(CH_2)_m$—Br, MS (ISP) 424.5 $(M+H)^+$.

Example 81

1-(4-Methoxy-benzyl)-2-(2-methoxy-phenyl)-5-methyl-1H-imidazole-4-carboxylic acid cyclohexylamide

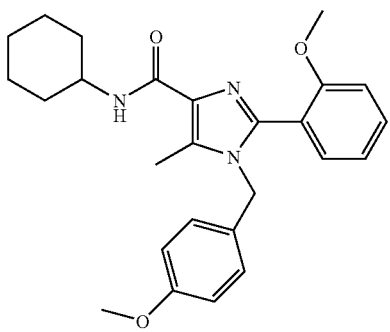

The title compound was synthesized in analogy to Example 49, using 2-methoxy benzylamine as $R^4$—$CH_2$—$NH_2$, cyclohexylamine as $R^1R^2NH$ and 4-methoxy-benzyl-chloride as $R^3$—$(CH_2)_m$—Br, MS (ISP) 434.5 $(M+H)^+$.

Example 82

Cyclohexylmethyl-5-methyl-2-(4-trifluoromethoxy-phenyl)-1H-imidazole-4-carboxylic acid piperidin-1-ylamide

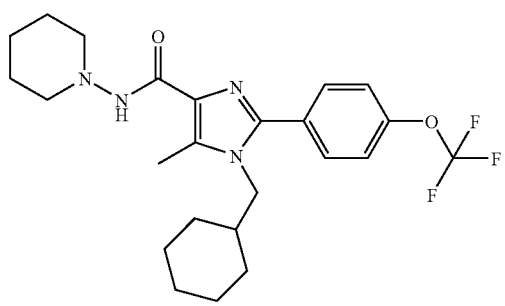

The title compound was synthesized in analogy to Example 49, using 4-trifluoromethoxy-benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 465.4 $(M+H)^+$.

Example 83

1-(2-Cyclohexyl-ethyl)-5-methyl-2-(4-trifluoromethoxy-phenyl)-1H-imidazole-4-carboxylic acid piperidin-1-ylamide

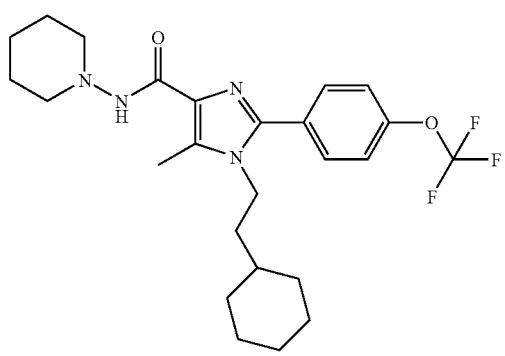

The title compound was synthesized in analogy to Example 49, using 4-trifluoromethoxy-benzylamine as $R^4$—$CH_2$—$NH_2$, 1-piperidinamine as $R^1R^2NH$ and (bromoethyl)cyclohexane as $R^3$—$(CH_2)_m$—Br, MS (ISP) 479.5 $(M+H)^+$.

Example 84

1-(2-Methoxy-benzyl)-2-(2-methoxy-phenyl)-5-methyl-1H-imidazole-4-carboxylic acid cyclohexylamide

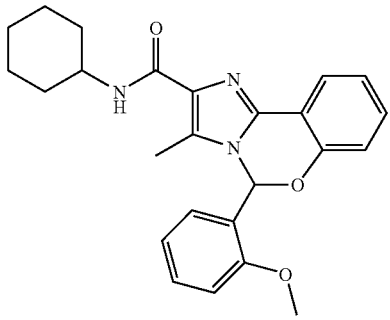

The title compound was synthesized in analogy to Example 49, using 2-methoxy-benzylamine as $R^4$—$CH_2$—$NH_2$, cyclohexylamine as $R^1R^2NH$ and 2-methoxy-benzyl-chloride as $R^3$—$(CH_2)_m$—Br, MS (ISP) 434.5 (M+H)$^+$.

Example 85

1-(3-Methoxy-benzyl)-2-(2-methoxy-phenyl)-5-methyl-1H-imidazole-4-carboxylic acid cyclohexylamide

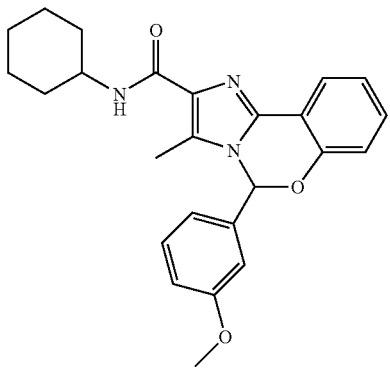

The title compound was synthesized in analogy to Example 49, using 2-methoxybenzylamine as $R^4$—$CH_2$—$NH_2$, cyclohexylamine as $R^1R^2NH$ and 3-methoxy-benzyl-chloride as $R^3$—$(CH_2)_m$—Br, MS (ISP) 434.4 (M+H)$^+$.

Example 86

Cyclohexylmethyl-5-(4-imidazol-1-yl-phenyl)-2-methyl-1H-pyrrole-3-carboxylic acid cyclohexylamide

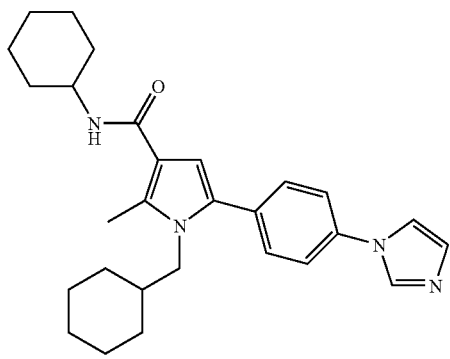

The title compound was synthesized in analogy to Example 1, using cyclohexylamine as $R^1R^2NH$, c-cyclohexyl-methylamine as $R^3$—$(CH_2)_m$—$NH_2$ and 2-Bromo-1-(4-imidazol-1-yl-phenyl)-ethanone [110668-69-4], MS (ISP) 445.3 (M+H)$^+$.

Example 87

5-(4-Chloro-2-fluoro-5-methyl-phenyl)-1-cyclohexylmethyl-2-methyl-1H-pyrrole-3-carboxylic acid cyclohexylamide

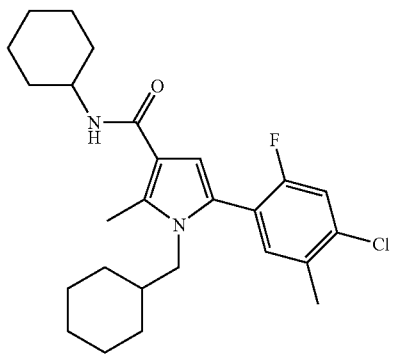

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(5-chloro-2-fluoro-4-methyl-phenyl)-ethanone [338982-26-6], MS (ISP) 445.3 (M+H)$^+$.

Example 88

Cyclohexylmethyl-5-(2-ethyl-phenyl)-2-methyl-1H-pyrrole-3-carboxylic acid cyclohexylamide

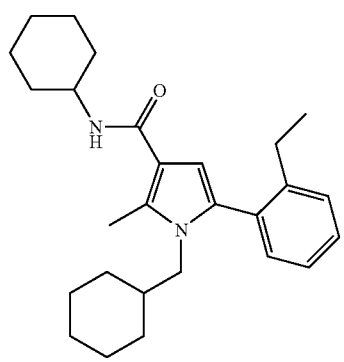

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(2-ethyl-phenyl)-ethanone (available from 1-(2-ethyl-phenyl)-ethanone [2142-64-5] following the procedure described by D. W. Robertson et. Al, *J. Med. Chem.*, 29, 1986, 1577-1586); MS (ISP) 407.4 (M+H)$^+$.

Example 89

5-(5-Chloro-2-methoxy-phenyl)-1-cyclohexylmethyl-2-methyl-1H-pyrrole-3-carboxylic acid cyclohexylamide

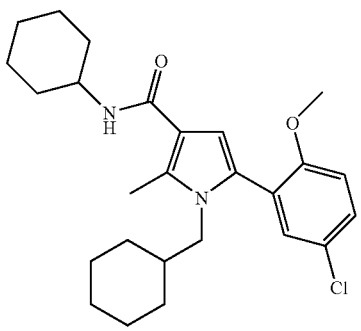

The title compound was synthesized in analogy to Example 1, using cyclohexylamine as R¹R²NH, c-cyclohexyl-methylamine as R³—(CH₂)ₘ—NH₂ and 2-Bromo-1-(5-chloro-2-methoxy-phenyl)-ethanone, MS (ISP) 443.2 (M+H)⁺.

Example 90

Cyclohexylmethyl-5-(5-fluoro-2-methoxy-phenyl)-2-methyl-1H-pyrrole-3-carboxylic acid cyclohexylamide

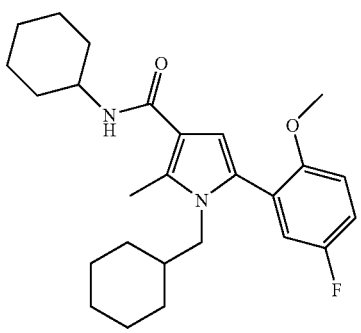

The title compound was synthesized in analogy to Example 1, using cyclohexylamine as R¹R²NH, c-cyclohexyl-methylamine as R³—(CH₂)ₘ—NH₂ and 2-Bromo-1-(5-fluoro-2-methoxy-phenyl)-ethanone, MS (ISP) 427.2 (M+H)⁺.

Example 91

5-(5-Chloro-2-methoxy-4-methyl-phenyl)-1-cyclohexylmethyl-2-methyl-1H-pyrrole-3-carboxylic acid cyclohexylamide

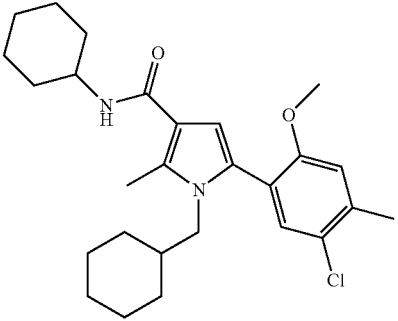

The title compound was synthesized in analogy to Example 1, using cyclohexylamine as R¹R²NH, c-cyclohexyl-methylamine as R³—(CH₂)ₘ—NH₂ and 2-bromo-1-(5-chloro-2-methoxy-4-methyl-phenyl)-ethanone (available from 1-(5-chloro-2-methoxy-4-methyl-phenyl)-ethanone [28478-40-2] following the procedure described by D. W. Robertson et. Al, *J. Med. Chem.*, 29, 1986, 1577-1586); MS (ISP) 457.3 (M+H)⁺.

Example 92

5-(3-Bromo-4-dimethylamino-phenyl)-1-cyclohexylmethyl-2-methyl-1H-pyrrole-3-carboxylic acid cyclohexylamide

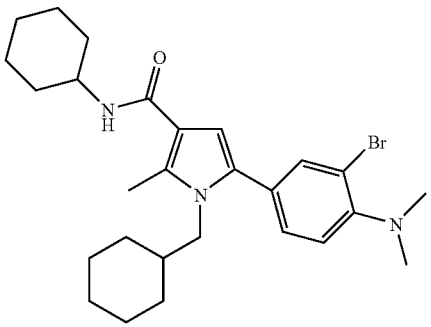

The title compound was synthesized in analogy to Example 1, using cyclohexylamine as R¹R²NH, c-cyclohexyl-methylamine as R³—(CH₂)ₘ—NH₂ and 2-bromo-1-(3-bromo-4-dimethylamino-phenyl)-ethanone (available from 1-(3-bromo-4-dimethylamino-phenyl)-ethanone [142500-11-6] following the procedure described by D. W. Robertson et. Al, *J. Med. Chem.*, 29, 1986, 1577-1586); MS (ISP) 500.3 (M+H)⁺.

Example 93

Cyclohexylmethyl-5-(4-hydroxy-2-methyl-phenyl)-2-methyl-1H-pyrrole-3-carboxylic acid cyclohexylamide

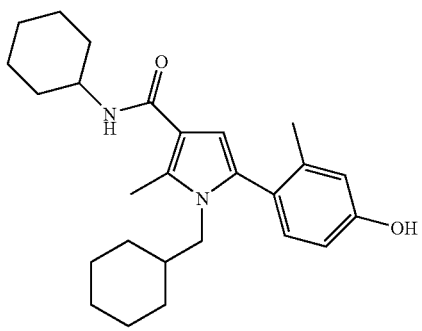

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(4-hydroxy-2-methyl-phenyl)-ethanone [41877-16-1], MS (ISP) 409.5 (M+H)$^+$.

Example 94

Cyclohexylmethyl-5-(2-fluoro-4-methoxy-phenyl)-2-methyl-1H-pyrrole-3-carboxylic acid cyclohexylamide

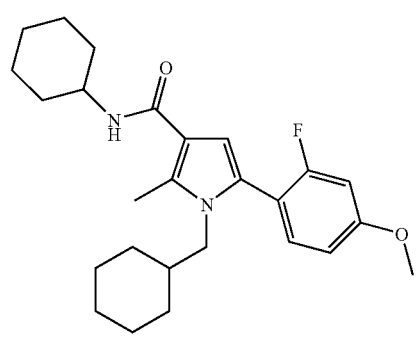

The title compound was synthesized in analogy to Example 1, using cyclohexylamine as $R^1R^2NH$, c-cyclohexyl-methylamine as $R^3$—$(CH_2)_m$—$NH_2$ and 2-Bromo-1-(2-fluoro-4-methoxy-phenyl)-ethanone [157014-35-2], MS (ISP) 427.5 (M+H)$^+$.

Example 95

5-(3-Bromo-phenyl)-1-cyclohexylmethyl-2-methyl-1H-pyrrole-3-carboxylic acid cyclohexylamide

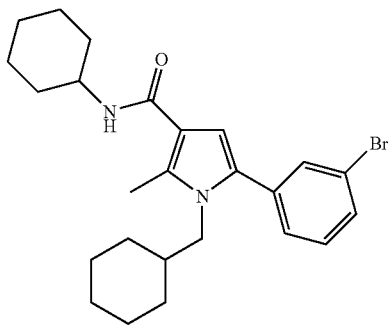

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(3-bromo-phenyl)-ethanone, MS (ISP) 457.4 (M+H)$^+$.

Example 96

Cyclohexylmethyl-5-(2,5-dimethoxy-phenyl)-2-propyl-1H-pyrrole-3-carboxylic acid piperidin-1-ylamide

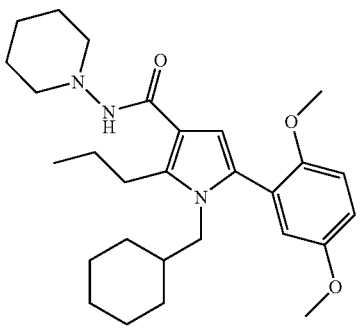

The title compound was synthesized in analogy to Example 68, using 3-oxo-hexanoic acid ethyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 1-piperidinamine as $R^1R^2NH$, MS (ISP) 468.4 (M+H)$^+$.

Example 97

Cyclohexylmethyl-5-(2,5-dimethoxy-phenyl)-2-ethyl-1H-pyrrole-3-carboxylic acid piperidin-1-ylamide

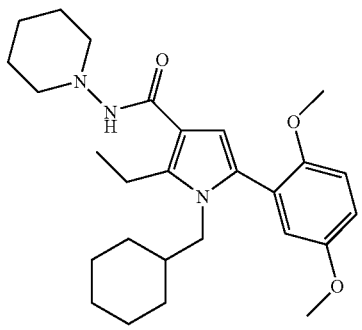

The title compound was synthesized in analogy to Example 68, using 3-oxo-pentanoic acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 1-piperidinamine as $R^1R^2NH$, MS (ISP) 454.6 $(M+H)^+$.

Example 98

1-(2-Cyclohexyl-ethyl)-5-methyl-2-(4-trifluoromethoxy-phenyl)-1H-imidazole-4-carboxylic acid cyclopropylamide

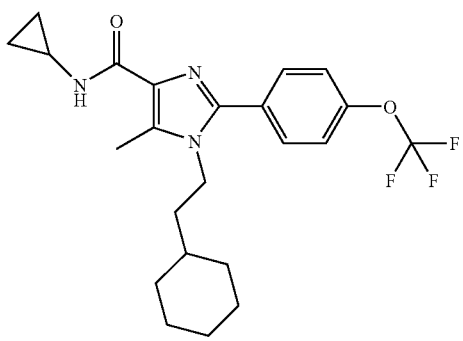

The title compound was synthesized in analogy to Example 49, using 4-trifluoromethoxy-benzylamine as $R^4$—$CH_2$—$NH_2$, cyclopropylamine as $R^1R^2NH$ and (bromoethyl)cyclohexane as $R^3$—$(CH_2)_m$—Br, MS (ISP) 436.3 $(M+H)^+$.

Example 99

Cyclohexylmethyl-5-methyl-2-(4-trifluoromethoxy-phenyl)-1H-imidazole-4-carboxylic acid cyclohexylamide

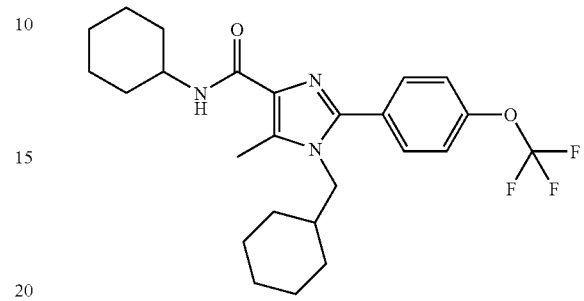

The title compound was synthesized in analogy to Example 49, using 4-trifluoromethoxy-benzylamine as $R^4$—$CH_2$—$NH_2$, cyclohexylamine as $R^1R^2NH$ and (bromomethyl)cyclohexane as $R^3$—$(CH_2)_m$—Br, MS (ISP) 464.2 $(M+H)^+$.

Example 100

Cyclohexylmethyl-5-(2,5-dimethoxy-phenyl)-2-methyl-1H-pyrrole-3-carboxylic acid (piperidin-4-ylmethyl)-amide, trifluoro-acetic acid salt

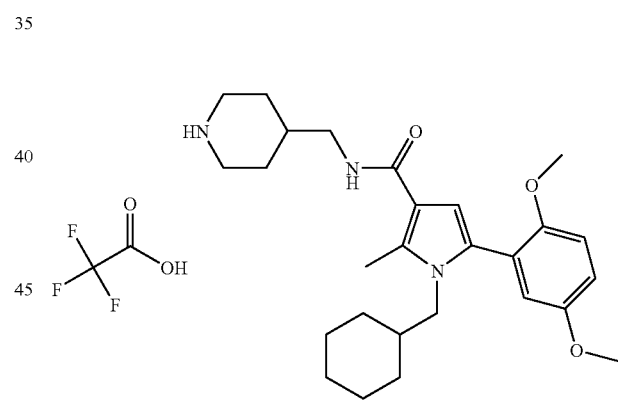

Preparation of 4-({[1-Cyclohexylmethyl-5-(2,5-dimethoxy-phenyl)-2-methyl-1H-pyrrole-3-carbonyl]-amino}-methyl)-piperidine-1-carboxylic acid tert-butyl ester.

4-({[1-Cyclohexylmethyl-5-(2,5-dimethoxy-phenyl)-2-methyl-1H-pyrrole-3-carbonyl]-amino}-methyl)-piperidine-1-carboxylic acid tert-butyl ester was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 4-Aminomethyl-piperidine-1-carboxylic acid tert-butyl ester as $R^1R^2NH$, MS (ISP) 554.5 $(M+H)^+$.

Preparation of 1-Cyclohexylmethyl-5-(2,5-dimethoxy-phenyl)-2-methyl-1H-pyrrole-3-carboxylic acid (piperidin-4-ylmethyl)-amide, trifluoro-acetic acid salt To 147 mg of 4-({[1-Cyclohexylmethyl-5-(2,5-dimethoxy-phenyl)-2-methyl-1H-pyrrole-3-carbonyl]-amino}-methyl)-piperidine-1-carboxylic acid tert-butyl ester in dichloromethane (2 ml) was added trifluoroacetic acid (2 ml) and the reaction mixture was stirred for 45 minutes at room temperature. After such time, the reaction mixture was concentrated in vacuo to yield the title compound; MS (ISP) 454.3 (M+H)$^+$.

Example 101

Cyclohexylmethyl-5-(2,5-dimethoxy-phenyl)-2-methyl-1H-pyrrole-3-carboxylic acid (2-methoxy-ethyl)-amide

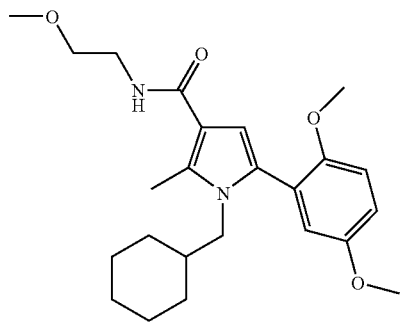

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 2-methoxy-ethylamine as $R^1R^2NH$, MS (ISP) 415.2 (M+H)$^+$.

Example 102

2-(5-Chloro-2-methoxy-phenyl)-1-cyclohexylmethyl-5-methyl-1H-imidazole-4-carboxylic acid cyclohexylamide

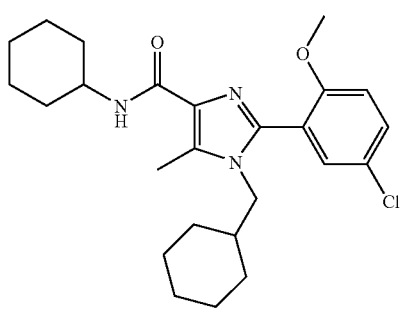

The title compound was synthesized in analogy to Example 49, using 5-chloro-2-methoxy-benzylamine as $R^4$—$CH_2$—$NH_2$, cyclohexylamine as $R^1R^2NH$ and (bromomethyl)cyclohexane as $R^3$—$(CH_2)_m$—$Br$, MS (ISP) 445.5 (M+H)$^+$.

Example 103

2-(5-Chloro-2-methoxy-phenyl)-1-cyclohexylmethyl-5-methyl-1H-imidazole-4-carboxylic acid piperidin-1-ylamide

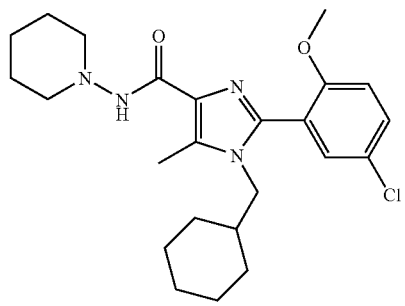

The title compound was synthesized in analogy to Example 49, using 5-chloro-2-methoxy-benzylamine as $R^4$—$CH_2$—$NH_2$, 2-aminopiperidine as $R^1R^2NH$ and (bromomethyl)cyclohexane as $R^3$—$(CH_2)_m$—$Br$, MS (ISP) 445.3 (M+H)$^+$.

Example 104

Cyclohexylmethyl-5-methyl-2-(4-trifluoromethoxy-phenyl)-1H-imidazole-4-carboxylic acid cyclopropylamide

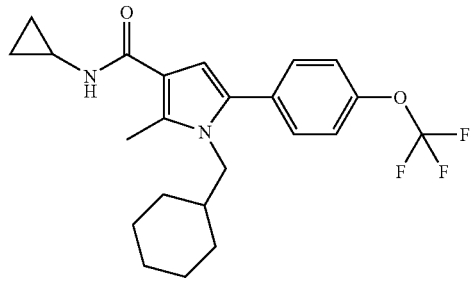

The title compound was synthesized in analogy to Example 49, using 4-trifluoromethoxy-benzylamine as $R^4$—$CH_2$—$NH_2$, cyclopropylamine as $R^1R^2NH$ and (bromomethyl)cyclohexane as $R^3$—$(CH_2)_m$—$Br$, MS (ISP) 422.2 (M+H)$^+$.

Example 105

Cyclohexylmethyl-5-methyl-2-(4-trifluoromethoxy-phenyl)-1H-imidazole-4-carboxylic acid cyclopentylamide

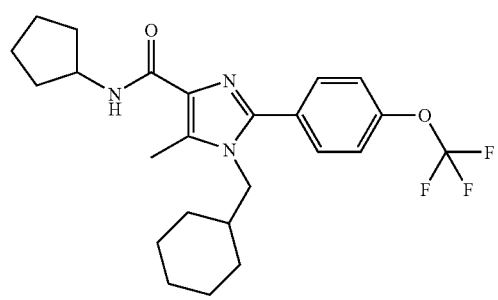

The title compound was synthesized in analogy to Example 49, using 4-trifluoromethoxy-benzylamine as $R^4$—$CH_2$—$NH_2$, cyclopentylamine as $R^1R^2NH$ and (bromomethyl)cyclohexane as $R^3$—$(CH_2)_m$—Br, MS (ISP) 450.2 $(M+H)^+$.

Example 106

2-(5-Chloro-2-methoxy-phenyl)-1-(2-cyclohexyl-ethyl)-5-methyl-1H-imidazole-4-carboxylic acid piperidin-1-ylamide

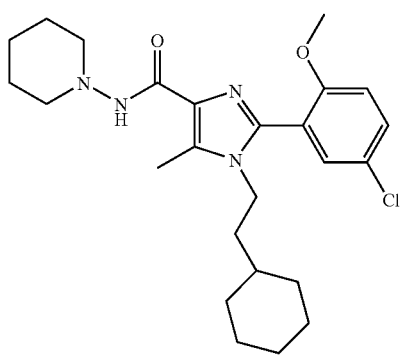

The title compound was synthesized in analogy to Example 49, using 5-chloro-2-methoxy-benzylamine as $R^4$—$CH_2$—$NH_2$, 1-piperidinamine as $R^1R^2NH$ and (bromoethyl)cyclohexane as $R^3$—$(CH_2)_m$—Br, MS (ISP) 459.3 $(M+H)^+$.

Example 107

2-(5-Chloro-2-methoxy-phenyl)-1-cyclohexylmethyl-5-methyl-1H-imidazole-4-carboxylic acid cyclopentylamide

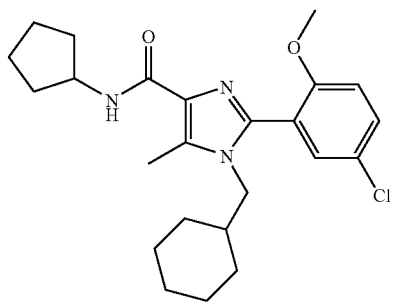

The title compound was synthesized in analogy to Example 49, using 5-chloro-2-methoxy-benzylamine as $R^4$—$CH_2$—$NH_2$, cyclopentylamine as $R^1R^2NH$ and (bromomethyl)cyclohexane as $R^3$—$(CH_2)_m$—Br, MS (ISP) 430.2 $(M+H)^+$.

Example 108

2-(5-Chloro-2-methoxy-phenyl)-1-(2-cyclohexyl-ethyl)-5-methyl-1H-imidazole-4-carboxylic acid cyclopentylamide

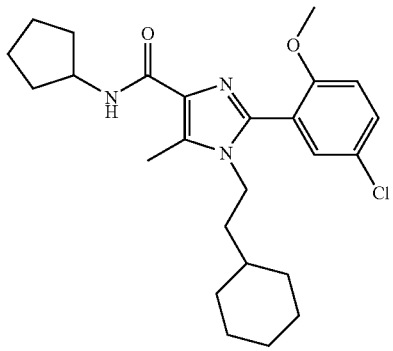

The title compound was synthesized in analogy to Example 49, using 5-chloro-2-methoxy-benzylamine as $R^4$—$CH_2$—$NH_2$, cyclopentylamine as $R^1R^2NH$ and (bromoethyl)cyclohexane as $R^3$—$(CH_2)_m$—Br, MS (ISP) 444.2 $(M+H)^+$.

Example 109

Cyclohexylmethyl-5-(2,5-dimethoxy-phenyl)-2-methyl-1H-pyrrole-3-carboxylic acid pyrimidin-2-ylamide

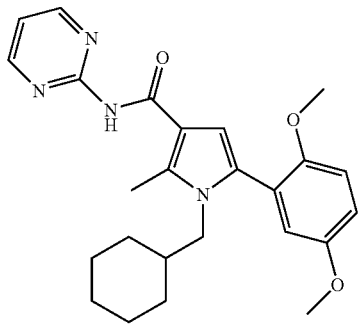

The title compound was synthesized in analogy to Example 1, using pyrimidin-2-ylamine as $R^1R^2NH$, c-cyclohexyl-methylamine as $R^3$—$(CH_2)_m$—$NH_2$ and pyrimidin-2-ylamine, MS (ISP) 435.3 $(M+H)^+$.

Example 110

Cyclohexylmethyl-5-(2,5-dimethoxy-phenyl)-2-methyl-1H-pyrrole-3-carboxylic acid (2-hydroxy-ethyl)-amide

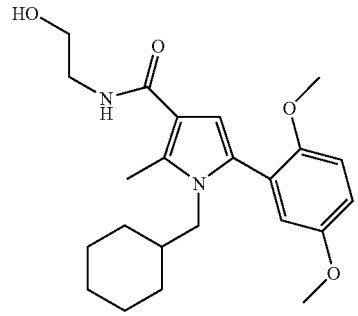

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 2-amino-ethanol as $R^1R^2NH$, MS (ISP) 401.3 (M+H)$^+$.

Example 111

Cyclohexylmethyl-5-(2,5-dimethoxy-phenyl)-2-methyl-1H-pyrrole-3-carboxylic acid (5-cyclopropyl-1H-pyrazol-3-ylmethyl)-amide

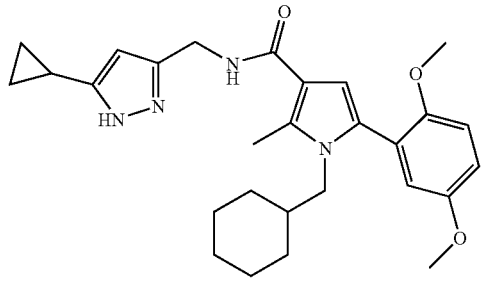

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and C-(5-Cyclopropyl-2H-pyrazol-3-yl)-methylamine as $R^1R^2NH$, MS (ISP) 477.5 (M+H)$^+$.

Example 112

Cyclohexylmethyl-5-(2,5-dimethoxy-phenyl)-2-methyl-1H-pyrrole-3-carboxylic acid (2-morpholin-4-yl-ethyl)-amide

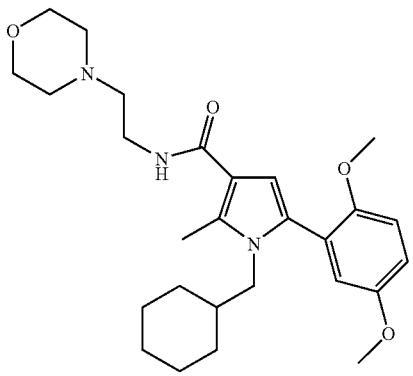

The title compound was synthesized in analogy to Example 68, using 3-oxo-butyric acid methyl ester as compound of formula R, 2-bromo-1-(2,5-dimethoxy-phenyl)-ethanone as compound of formula S, c-cyclohexyl-methylamine as $R^3$—$(CH_2)_m$—$NH_2$ and 2-morpholin-4-yl-ethylamine as $R^1R^2NH$, MS (ISP) 470.3 (M+H)$^+$.

Example 113

5-(3,5-Bis-trifluoromethyl-phenyl)-1-cyclohexylmethyl-2-methyl-1H-pyrrole-3-carboxylic acid piperidin-1-ylamide

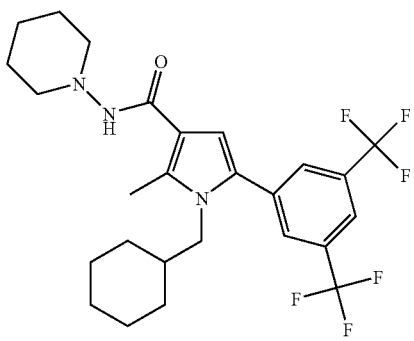

The title compound was synthesized in analogy to Example 68, using 3-oxo-butyric acid methyl ester as compound of formula R, 1-(3,5-Bis-trifluoromethyl-phenyl)-2-bromo-ethanone as compound of formula S, c-cyclohexyl-methylamine as $R^3$—$(CH_2)_m$—$NH_2$ and 1-piperidinamine as $R^1R^2NH$, MS (ISP) 516.3 (M+H)$^+$.

Example 114

Cyclohexylmethyl-5-methyl-2-(4-trifluoromethoxy-phenyl)-1H-imidazole-4-carboxylic acid butylamide

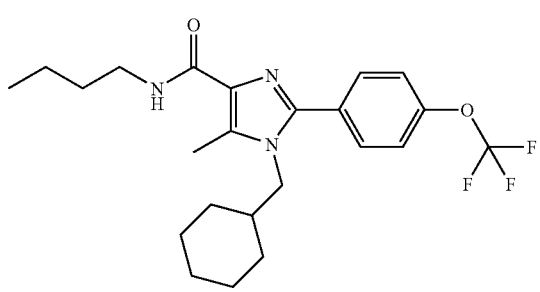

The title compound was synthesized in analogy to Example 49, using 4-trifluoromethoxy-benzylamine as $R^4$—$CH_2$—$NH_2$, n-butylamine as $R^1R^2NH$ and (bromomethyl)cyclohexane as $R^3$—$(CH_2)_m$—Br, MS (ISP) 438.3 (M+H)$^+$.

Example 115

1-(2-Cyclohexyl-ethyl)-5-methyl-2-(4-trifluoromethoxy-phenyl)-1H-imidazole-4-carboxylic acid butylamide

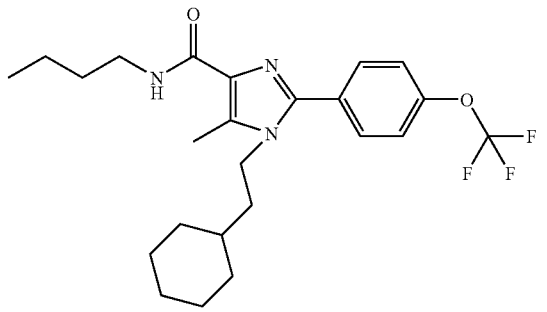

The title compound was synthesized in analogy to Example 49, using 4-trifluoromethoxy-benzylamine as $R^4$—$CH_2$—$NH_2$, n-butylamine as $R^1R^2NH$ and (bromoethyl)cyclohexane as $R^3$—$(CH_2)_m$—Br, MS (ISP) 452.2 (M+H)$^+$.

Example 116

1-(3-Methoxy-benzyl)-2-(2-methoxy-phenyl)-5-methyl-1H-imidazole-4-carboxylic acid piperidin-1-ylamide

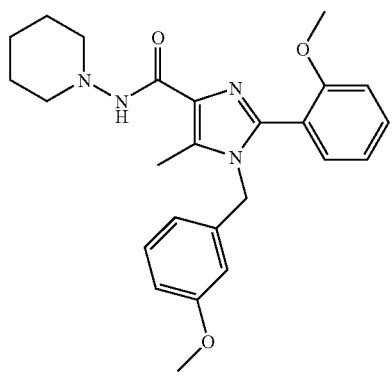

The title compound was synthesized in analogy to Example 49, using 2-methoxy-benzylamine as $R^4$—$CH_2$—$NH_2$, 1-piperidinamine as $R^1R^2NH$ and 3-methoxy-benzylbromide as $R^3$—$(CH_2)_m$—Br, MS (ISP) 435.3 (M+H)$^+$.

Example 117

2-(5-Chloro-2-methoxy-phenyl)-1-cyclohexylmethyl-5-methyl-1H-imidazole-4-carboxylic acid cyclopropylamide

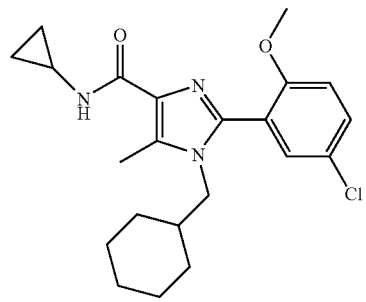

The title compound was synthesized in analogy to Example 49, using 5-chloro-2-methoxy-benzylamine as $R^4$—$CH_2$—$NH_2$, cyclopropylamine as $R^1R^2NH$ and (bromomethyl)cyclohexane as $R^3$—$(CH_2)_m$—Br, MS (ISP) 402.3 (M+H)$^+$.

Example 118

2-(5-Chloro-2-methoxy-phenyl)-1-(2-cyclohexyl-ethyl)-5-methyl-1H-imidazole-4-carboxylic acid cyclopropylamide

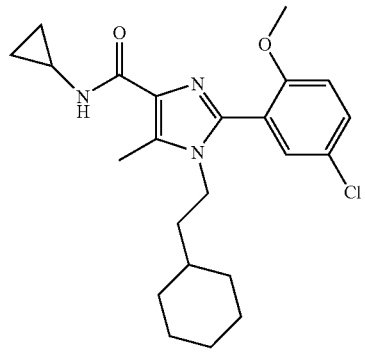

The title compound was synthesized in analogy to Example 49, using 5-chloro-2-methoxy-benzylamine as $R^4$—$CH_2$—$NH_2$, cyclopropylamine as $R^1R^2NH$ and (bromoethyl)cyclohexane as $R^3$—$(CH_2)_m$—Br, MS (ISP) 416.2 (M+H)$^+$.

Example 119

Cyclopropylmethyl-2-(2-methoxy-phenyl)-5-methyl-1H-imidazole-4-carboxylic acid cyclohexylamide

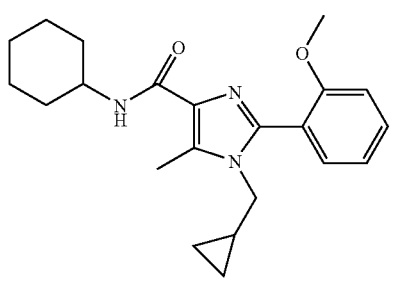

The title compound was synthesized in analogy to Example 49, using 2-methoxy-benzylamine as $R^4$—$CH_2$—$NH_2$, cyclohexylamine as $R^1R^2NH$ and (bromomethyl)cyclopropane as $R^3$—$(CH_2)_m$—Br, MS (ISP) 368.2 (M+H)$^+$.

Example 120

Cyclohexylmethyl-5-(3,5-dichloro-phenyl)-2-methyl-1H-pyrrole-3-carboxylic acid cyclohexylamide

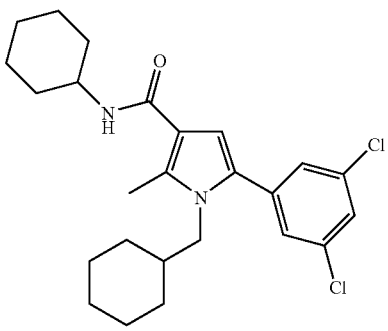

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(3,5-dichloro-phenyl)-ethanone, MS (ISP) 447.2 $(M+H)^+$.

Example 121

Cyclohexylmethyl-5-(3,5-difluoro-phenyl)-2-methyl-1H-pyrrole-3-carboxylic acid cyclohexylamide

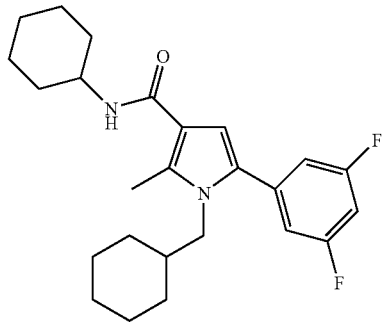

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(3,5-difluoro-phenyl)-ethanone, MS (ISP) 415.2 $(M+H)^+$.

Example 122

5-(5-Bromo-2-methoxy-phenyl)-1-cyclohexylmethyl-2-methyl-1H-pyrrole-3-carboxylic acid cyclohexylamide

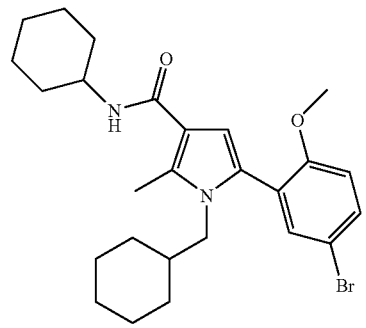

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(2-methoxy-5-bromo-phenyl)-ethanone, MS (ISP) 487.4 $(M+H)^+$.

Example 123

1-(2-Cyclopropyl-ethyl)-2-(2-methoxy-phenyl)-5-methyl-1H-imidazole-4-carboxylic acid piperidin-1-ylamide acid cyclohexylamide

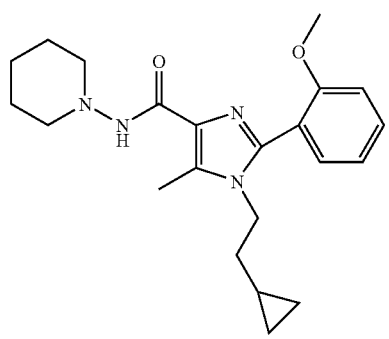

The title compound was synthesized in analogy to Example 49, using 2-methoxy-benzylamine as $R^4$—$CH_2$—$NH_2$, 1-piperidinamine as $R^1R^2NH$ and (bromoethyl)cyclopropane as $R^3$—$(CH_2)_m$—Br, MS (ISP) 383.3 $(M+H)^+$.

Example 124

Cyclohexylmethyl-5-methyl-2-(4-trifluoromethyl-phenyl)-1H-imidazole-4-carboxylic acid piperidin-1-ylamide

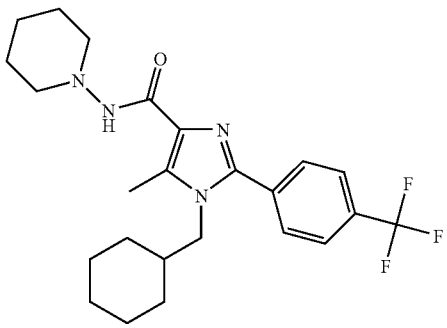

The title compound was synthesized in analogy to Example 49 using 4-trifluoromethyl benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 449.3 $(M+H)^+$.

Example 125

1-(2-Cyclopropyl-ethyl)-5-methyl-2-(4-trifluoromethoxy-phenyl)-1H-imidazole-4-carboxylic acid piperidin-1-ylamide

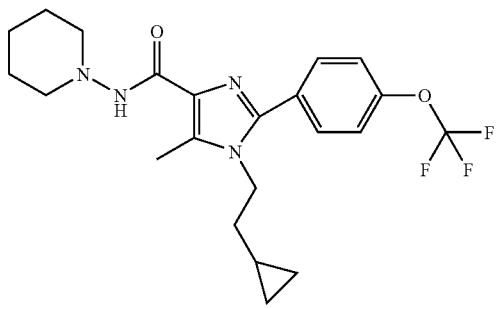

The title compound was synthesized in analogy to Example 49, using 4-trifluoromethoxy-benzylamine as $R^4$—$CH_2$—$NH_2$, 1-piperidinamine as $R^1R^2NH$ and (bromoethyl)cyclopropane as $R^3$—$(CH_2)_m$—Br, MS (ISP) 437.2 (M+H)$^+$.

Example 126

Cyclohexylmethyl-5-methyl-2-p-tolyl-1H-imidazole-4-carboxylic acid piperidin-1-ylamide

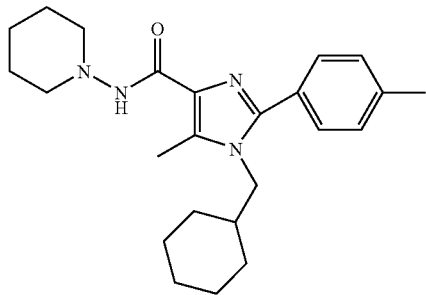

The title compound was synthesized in analogy to Example 49, using 4-methyl-benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 395.3 (M+H)$^+$.

Example 127

1-(2-Cyclohexyl-ethyl)-5-methyl-2-p-tolyl-1H-imidazole-4-carboxylic acid piperidin-1-ylamide

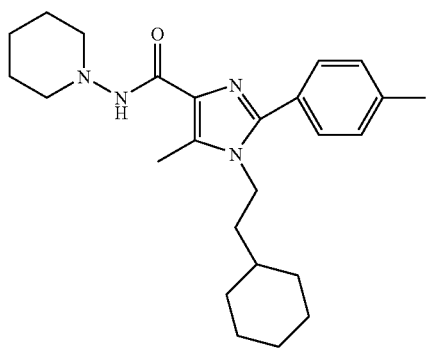

The title compound was synthesized in analogy to Example 49, using 4-methyl-benzylamine as $R^4$—$CH_2$—$NH_2$, 1-piperidinamine as $R^1R^2NH$ and (bromoethyl)cyclohexane as $R^3$—$(CH_2)_m$—Br, MS (ISP) 409.4 (M+H)$^+$.

Example 128

Cyclohexylmethyl-2-(5-fluoro-2-methyl-phenyl)-5-methyl-1H-imidazole-4-carboxylic acid cyclohexylamide

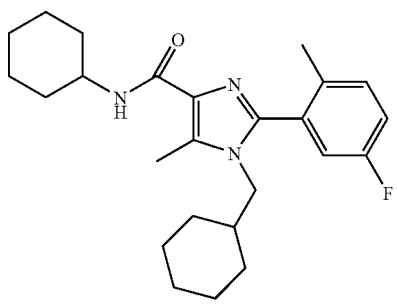

The title compound was synthesized in analogy to Example 49, using 5-fluoro-2-methyl-benzylamine as $R^4$—$CH_2$—$NH_2$, cyclohexylamine as $R^1R^2NH$ and (bromomethyl)cyclohexane as $R^3$—$(CH_2)_m$—Br, MS (ISP) 412.3 (M+H)$^+$.

Example 129

2-(3,5-Bis-trifluoromethyl-phenyl)-1-cyclohexylmethyl-5-methyl-1H-imidazole-4-carboxylic acid piperidin-1-ylamide

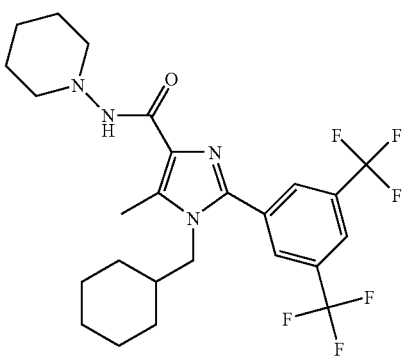

The title compound was synthesized in analogy to Example 49 using 3,5-bis-trifluoromethyl-benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 517.3 (M+H)$^+$.

Example 130

Cyclohexylmethyl-5-methyl-2-(3-trifluoromethyl-phenyl)-1H-imidazole-4-carboxylic acid piperidin-1-ylamide

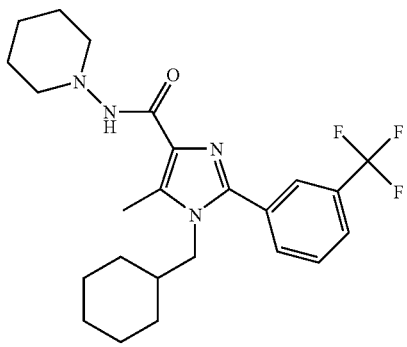

The title compound was synthesized in analogy to Example 49 using 3-trifluoromethyl benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 449.2 (M+H)$^+$.

Example 131

5-(3-Bromo-2-hydroxy-5-methoxy-phenyl)-1-cyclohexylmethyl-2-methyl-1H-pyrrole-3-carboxylic acid cyclohexylamide

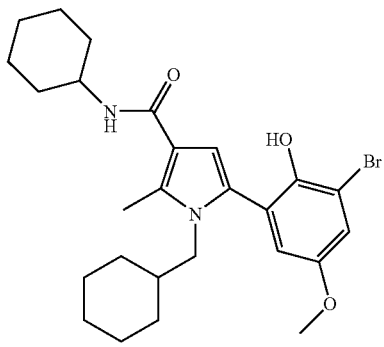

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(3-bromo-2-hydroxy-5-methoxy-phenyl)-ethanone, (available from 1-(3-bromo-2-hydroxy-5-methoxy-phenyl)-ethanone [37113-61-4] following the procedure described by D. W. Robertson et. al, *J. Med. Chem.,* 29, 1986, 1577-1586); MS (ISP) 505.2 (M+H)$^+$.

Example 132

Cyclohexylmethyl-5-methyl-2-p-tolyl-1H-imidazole-4-carboxylic acid cyclohexylamide

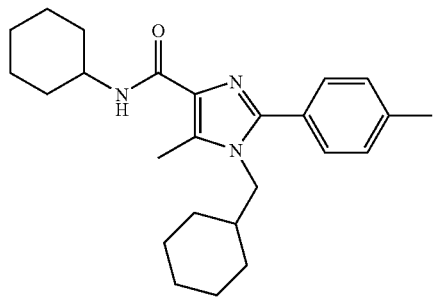

The title compound was synthesized in analogy to Example 49, using 4-methyl-benzylamine as $R^4$—$CH_2$—$NH_2$, cyclohexylamine as $R^1R^2NH$ and (bromomethyl)cyclohexane as $R^3$—$(CH_2)_m$—Br, MS (ISP) 394.2 (M+H)$^+$.

Example 133

Cyclohexylmethyl-5-methyl-2-p-tolyl-1H-imidazole-4-carboxylic acid butylamide

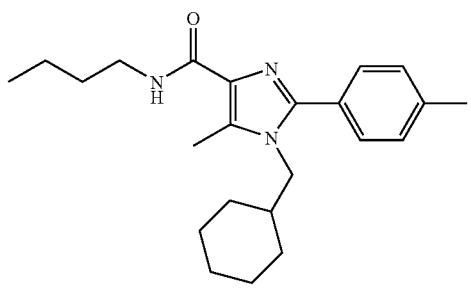

The title compound was synthesized in analogy to Example 49, using 4-methyl-benzylamine as $R^4$—$CH_2$—$NH_2$, butylamine as $R^1R^2NH$ and (bromomethyl)cyclohexane as $R^3$—$(CH_2)_m$—Br, MS (ISP) 368.2 (M+H)$^+$.

Example 134

1-(2-Cyclohexyl-ethyl)-5-methyl-2-p-tolyl-1H-imidazole-4-carboxylic acid butylamide

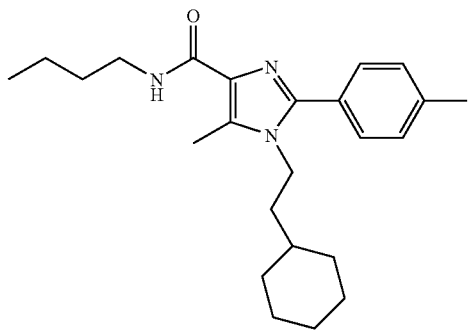

The title compound was synthesized in analogy to Example 49, using 4-methyl-benzylamine as $R^4$—$CH_2$—$NH_2$, butylamine as $R^1R^2NH$ and (bromoethyl)cyclohexane as $R^3$—$(CH_2)_m$—Br, MS (ISP) 382.3 (M+H)$^+$.

Example 135

5-(3,5-Difluoro-phenyl)-2-methyl-1-phenethyl-1H-pyrrole-3-carboxylic acid (3,3,3-trifluoro-propyl)-amide

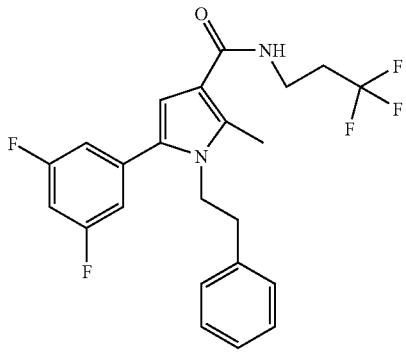

The title compound was synthesized in analogy to Example 68, using 3-oxo-butyric acid methyl ester as compound of formula R, 2-bromo-1-(3,5-difluoro-phenyl)-ethanone as compound of formula S, phenethylamine as $R^3$—$(CH_2)_m$—$NH_2$ and 3,3,3-trifluoro-N-propylamine as $R^1R^2NH$, MS (ISP) 437.2 $(M+H)^+$.

Example 136

Cyclohexylmethyl-2-(5-fluoro-2-methyl-phenyl)-5-methyl-1H-imidazole-4-carboxylic acid piperidin-1-ylamide

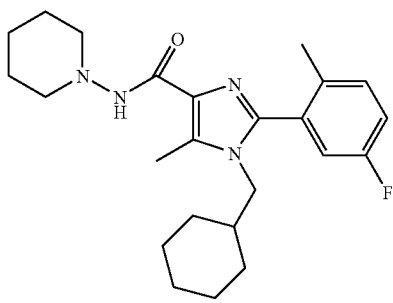

The title compound was synthesized in analogy to Example 49, using 5-fluoro-2-methyl-benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 413.4 $(M+H)^+$.

Example 137

1-(2-Cyclohexyl-ethyl)-2-(5-fluoro-2-methyl-phenyl)-5-methyl-1H-imidazole-4-carboxylic acid piperidin-1-ylamide

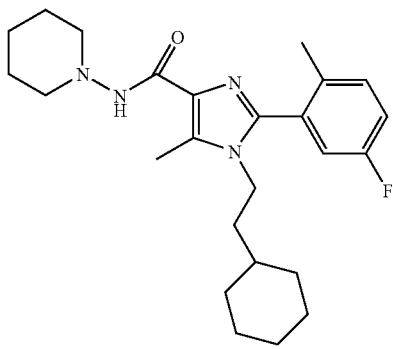

The title compound was synthesized in analogy to Example 49, using 5-fluoro-2-methyl-benzylamine as $R^4$—$CH_2$—$NH_2$, 1-piperidinamine as $R^1R^2NH$ and (bromoethyl)cyclohexane as $R^3$—$(CH_2)_m$—Br, MS (ISP) 427.3 $(M+H)^+$.

Example 138

(RAC) 2-(5-Chloro-2-methoxy-phenyl)-1-(3-methoxy-cyclohexylmethyl)-5-methyl-1H-imidazole-4-carboxylic acid piperidin-1-ylamide

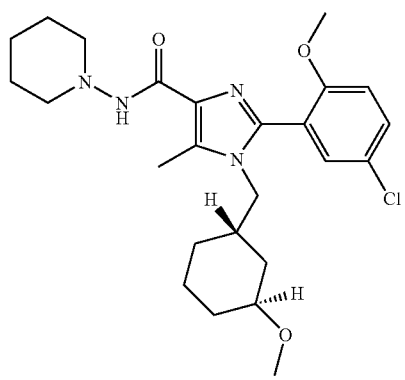

The title compound was synthesized in analogy to Example 49, using 5-chloro-2-methoxy-benzylamine as $R^4$—$CH_2$—$NH_2$, 1-piperidinamine as $R^1R^2NH$ and 1-bromomethyl-3-methoxy-cyclohexane as $R^3$—$(CH_2)_m$—Br, MS (ISP) 475.2 $(M+H)^+$.

Example 139

(RAC) 1-(3-Methoxy-cyclohexylmethyl)-2-(2-methoxy-phenyl)-5-methyl-1H-imidazole-4-carboxylic acid piperidin-1-ylamide

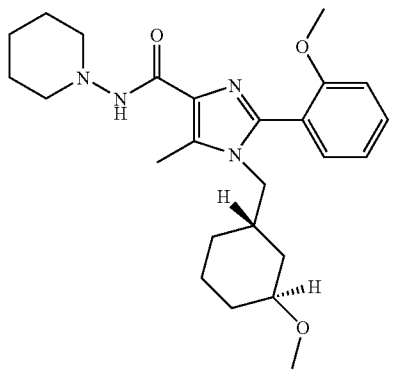

The title compound was synthesized in analogy to Example 49, using 2-methoxy-benzylamine as $R^4$—$CH_2$—$NH_2$, 1-piperidinamine as $R^1R^2NH$ and 1-bromomethyl-3-methoxy-cyclohexane as $R^3$—$(CH_2)_m$—Br, MS (ISP) 441.3 $(M+H)^+$.

Example 140
5-(3,5-Bis-trifluoromethyl-phenyl)-1-(3-fluoro-benzyl)-2-methyl-1H-pyrrole-3-carboxylic acid cyclohexylamide

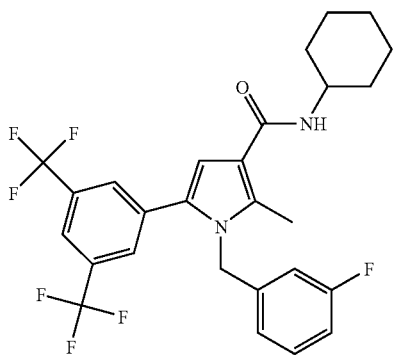

The title compound was synthesized in analogy to Example 68, using 3-oxo-butyric acid methyl ester as compound of formula R, 1-(3,5-bis-trifluoromethyl-phenyl)-2-bromo-ethanone as compound of formula S, 3-fluorobenzylamine as R3-(CH2)m-NH2 and cyclohexylamine as $R^1R^2NH$, MS (ISP) 527.2 $(M+H)^+$.

Example 141
5-(3,5-Bis-trifluoromethyl-phenyl)-1-(3-fluoro-benzyl)-2-methyl-1H-pyrrole-3-carboxylic acid piperidin-1-ylamide

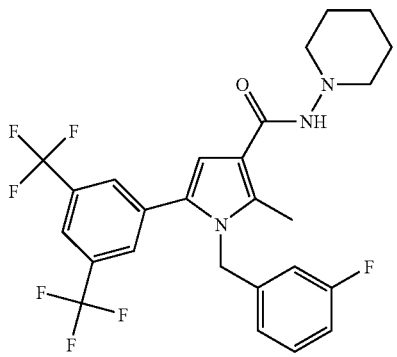

The title compound was synthesized in analogy to Example 68, using 3-oxo-butyric acid methyl ester as compound of formula R, 1-(3,5-bis-trifluoromethyl-phenyl)-2-bromo-ethanone as compound of formula S, 3-fluorobenzylamine as $R^3$—$(CH_2)_m$—$NH_2$ and 1-piperidinamine as $R^1R^2NH$, MS (ISP) 528.2 $(M+H)^+$.

Example 142
2-(5-Chloro-2-methoxy-phenyl)-1-(2-cyclopropyl-ethyl)-5-methyl-1H-imidazole-4-carboxylic acid piperidin-1-ylamide

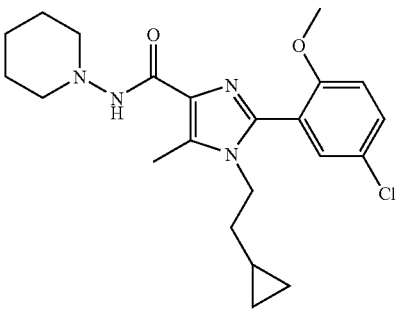

The title compound was synthesized in analogy to Example 49, using 5-chloro-2-methoxy-benzylamine as $R^4$—$CH_2$—$NH_2$, 1-piperidinamine as $R^1R^2NH$ and (2-bromo-ethyl)-cyclopropane as $R^3$—$(CH_2)_m$—Br, MS (ISP) 417.2 $(M+H)^+$.

Example 143
2-(2-Chloro-5-trifluoromethyl-phenyl)-1-cyclohexylmethyl-5-methyl-1H-imidazole-4-carboxylic acid piperidin-1-ylamide

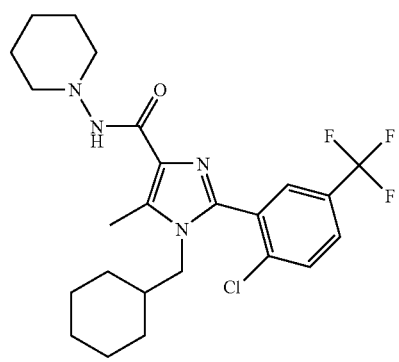

The title compound was synthesized in analogy to Example 49 using 2-chloro-5-trifluoromethyl-benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 483.2 $(M+H)^+$.

Example 144
Cyclohexylmethyl-2-(3,5-dimethoxy-phenyl)-5-methyl-1H-imidazole-4-carboxylic acid piperidin-1-ylamide

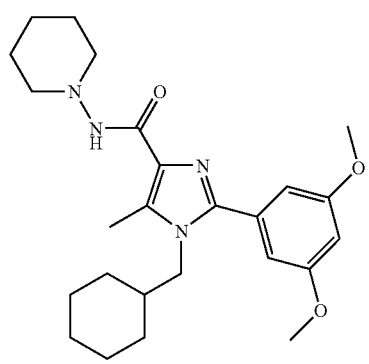

The title compound was synthesized in analogy to Example 49 using 3,5-dimethoxy-benzylamine as $R^4$—$CH_2$—$NH_2$, 1-piperidinamine as $R^1R^2NH$ and (bromomethyl)cyclohexane as $R^3$—$(CH_2)_m$—Br, MS (ISP) 441.3 $(M+H)^+$.

Example 145

Cyclohexylmethyl-2-(5-fluoro-2-methyl-phenyl)-5-methyl-1H-imidazole-4-carboxylic acid (3,3,3-trifluoro-propyl)-amide

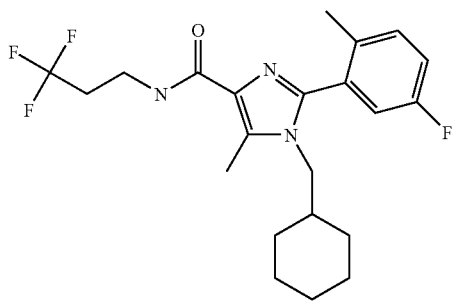

The title compound was synthesized in analogy to Example 49, using 5-fluoro-2-methyl-benzylamine as $R^4$—$CH_2$—$NH_2$, 3,3,3-trifluoro-propylamine as $R^1R^2NH$ and (bromomethyl)-cyclohexane as $R^3$—$(CH_2)_m$—Br, MS (ISP) 426 (M+H)$^+$.

Example 146

Cyclohexylmethyl-2-(5-fluoro-2-methyl-phenyl)-5-methyl-1H-imidazole-4-carboxylic acid cyclobutylamide

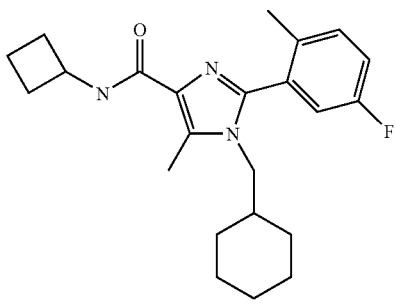

The title compound was synthesized in analogy to Example 49, using 5-fluoro-2-methyl-benzylamine as $R^4$—$CH_2$—$NH_2$, cyclobutylamine as $R^1R^2NH$ and (bromomethyl)-cyclohexane as $R^3$—$(CH_2)_m$—Br, MS (ISP) 384 (M+H)$^+$.

Example 147

2-(5-Chloro-2-methyl-phenyl)-1-cyclohexylmethyl-5-methyl-1H-imidazole-4-carboxylic acid butylamide

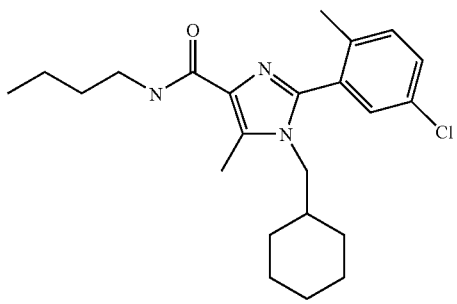

The title compound was synthesized in analogy to Example 49, using 5-chloro-2-methyl-benzylamine as $R^4$—$CH_2$—$NH_2$, n-butylamine as $R^1R^2NH$ and (bromomethyl)-cyclohexane as $R^3$—$(CH_2)_m$—Br, MS (ISP) 402 (M+H)$^+$.

Example 148

2-(4-Chloro-2-methyl-phenyl)-1-cyclohexylmethyl-5-methyl-1H-imidazole-4-carboxylic acid (3,3,3-trifluoro-propyl)-amide

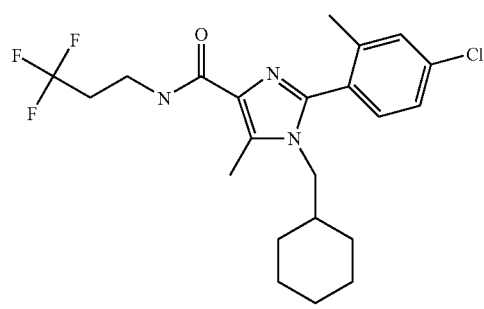

The title compound was synthesized in analogy to Example 49, using 4-chloro-2-methyl-benzylamine as $R^4$—$CH_2$—$NH_2$, 3,3,3-trifluoro-propylamine as $R^1R^2NH$ and (bromomethyl)-cyclohexane as $R^3$—$(CH_2)_m$—Br, MS (ISP) 442 (M+H)$^+$.

Example 149

1-(2-Cyclohexyl-ethyl)-2-(5-fluoro-2-methyl-phenyl)-5-methyl-1H-imidazole-4-carboxylic acid butylamide

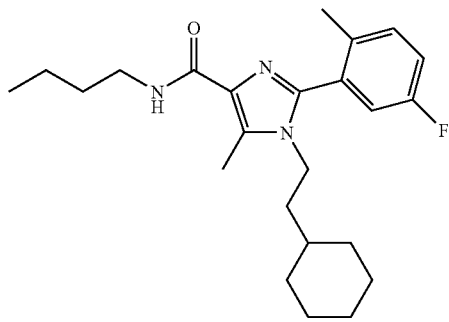

The title compound was synthesized in analogy to Example 49, using 5-fluoro-2-methyl-benzylamine as $R^4$—$CH_2$—$NH_2$, n-butylamine as $R^1R^2NH$ and (bromoethyl)-cyclohexane as $R^3$—$(CH_2)_m$—Br, MS (ISP) 400 (M+H)$^+$.

Example 150

2-(5-Chloro-2-methyl-phenyl)-1-(2-cyclohexyl-ethyl)-5-methyl-1H-imidazole-4-carboxylic acid (3,3,3-trifluoro-propyl)-amide

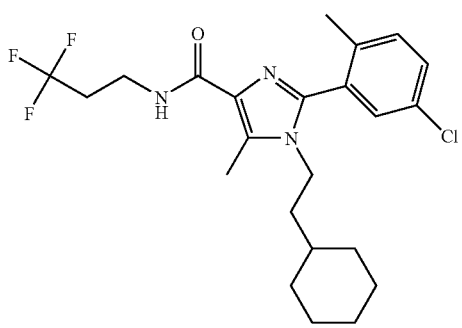

The title compound was synthesized in analogy to Example 49, using 5-chloro-2-methyl-benzylamine as $R^4$—$CH_2$—$NH_2$, 3,3,3-trifluoro-propylamine as $R^1R^2NH$ and (bromoethyl)-cyclohexane as $R^3$—$(CH_2)_m$—Br, MS (ISP) 456 (M+H)$^+$.

Example 151

2-(5-Chloro-2-methyl-phenyl)-1-cyclohexylmethyl-5-methyl-1H-imidazole-4-carboxylic acid (3,3,3-trifluoro-propyl)-amide

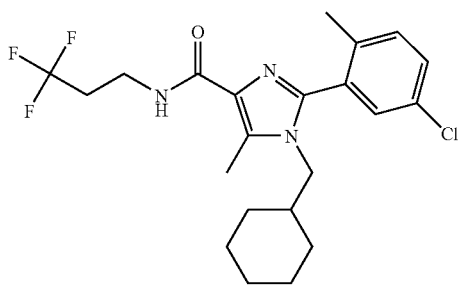

The title compound was synthesized in analogy to Example 49, using 5-chloro-2-methyl-benzylamine as $R^4$—$CH_2$—$NH_2$, 3,3,3-trifluoro-propylamine as $R^1R^2NH$ and (bromomethyl)-cyclohexane as $R^3$—$(CH_2)_m$—Br, MS (ISP) 442 (M+H)$^+$.

Example 152

2-(5-Chloro-2-methyl-phenyl)-1-cyclohexylmethyl-5-methyl-1H-imidazole-4-carboxylic acid piperidin-1-ylamide

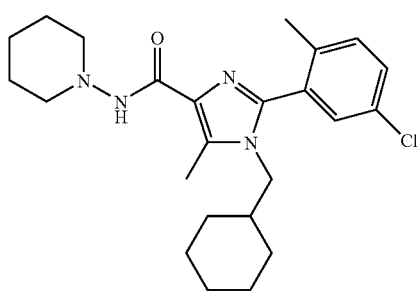

The title compound was synthesized in analogy to Example 49, using 5-chloro-2-methyl-benzylamine as $R^4$—$CH_2$—$NH_2$, 1-amino-piperidine as $R^1R^2NH$ and (bromomethyl)-cyclohexane as $R^3$—$(CH_2)_m$—Br, MS (ISP) 429 (M+H)$^+$.

Example 153

2-(4-Chloro-2-methyl-phenyl)-1-(2-cyclohexyl-ethyl)-5-methyl-1H-imidazole-4-carboxylic acid (3,3,3-trifluoro-propyl)-amide

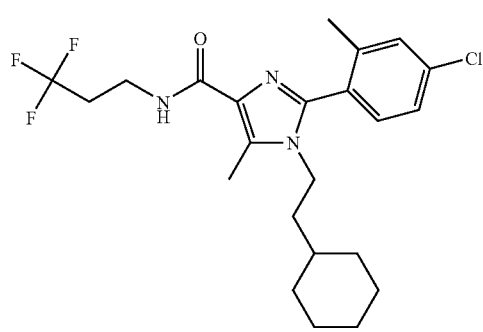

The title compound was synthesized in analogy to Example 49, using 4-chloro-2-methyl-benzylamine as $R^4$—$CH_2$—$NH_2$, 3,3,3-trifluoro-propylamine as $R^1R^2NH$ and (bromoethyl)-cyclohexane as $R^3$—$(CH_2)_m$—Br, MS (ISP) 456 (M+H)$^+$.

Example 154

2-(5-Chloro-2-methyl-phenyl)-1-(2-cyclohexyl-ethyl)-5-methyl-1H-imidazole-4-carboxylic acid cyclopentylamide

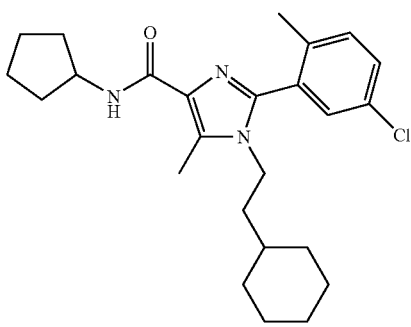

The title compound was synthesized in analogy to Example 49, using 4-chloro-2-methyl-benzylamine as $R^4$—$CH_2$—$NH_2$, cyclopentylamine as $R^1R^2NH$ and (bromoethyl)-cyclohexane as $R^3$—$(CH_2)_m$—Br, MS (ISP) 428 (M+H)$^+$.

Example 155

1-(2-Cyclohexyl-ethyl)-2-(3,4-dichloro-phenyl)-5-methyl-1H-imidazole-4-carboxylic acid piperidin-1-ylamide

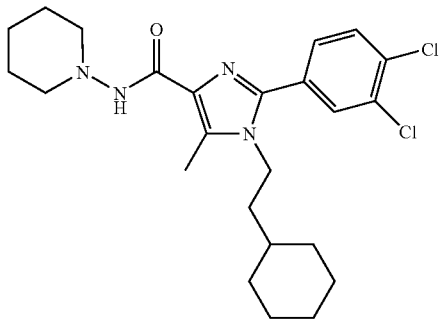

The title compound was synthesized in analogy to Example 49, using 3,4-dichloro-benzylamine as $R^4$—$CH_2$—$NH_2$, 1-amino-piperidine as $R^1R^2NH$ and (bromoethyl)-cyclohexane as $R^3$—$(CH_2)_m$—Br, MS (ISP) 463 (M+H)$^+$.

Example 156

2-(4-Chloro-2-methyl-phenyl)-1-cyclohexylmethyl-5-methyl-1H-imidazole-4-carboxylic acid butylamide

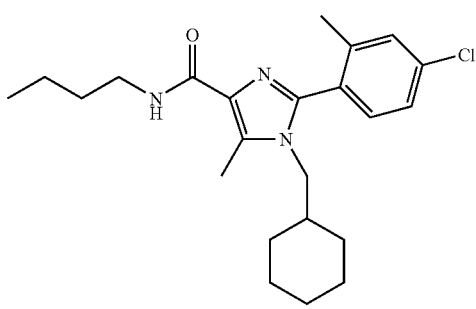

The title compound was synthesized in analogy to Example 49, using 4-chloro-2-methyl-benzylamine as $R^4$—$CH_2$—$NH_2$, n-butylamine as $R^1R^2NH$ and (bromomethyl)-cyclohexane as $R^3$—$(CH_2)_m$—Br, MS (ISP) 402 (M+H)$^+$.

Example 157

2-(5-Chloro-2-methyl-phenyl)-1-(2-cyclohexyl-ethyl)-5-methyl-1H-imidazole-4-carboxylic acid piperidin-1-ylamide

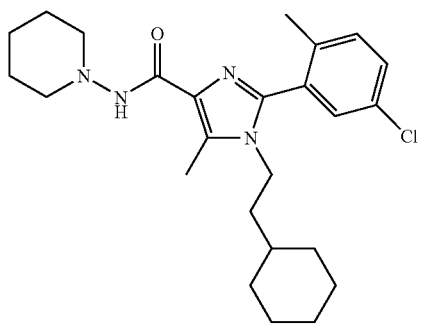

The title compound was synthesized in analogy to Example 49, using 5-chloro-2-methyl-benzylamine as $R^4$—$CH_2$—$NH_2$, 1-amino-piperidine as $R^1R^2NH$ and (bromoethyl)-cyclohexane as $R^3$—$(CH_2)_m$—Br, MS (ISP) 443 (M+H)$^+$.

Example 158

2-(4-Chloro-2-methyl-phenyl)-1-cyclohexylmethyl-5-methyl-1H-imidazole-4-carboxylic acid cyclohexylamide

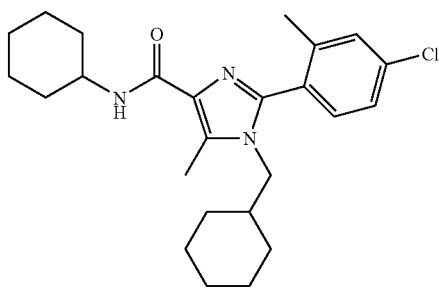

The title compound was synthesized in analogy to Example 49, using 4-chloro-2-methyl-benzylamine as $R^4$—$CH_2$—$NH_2$, cyclohexylamine as $R^1R^2NH$ and (bromomethyl)-cyclohexane as $R^3$—$(CH_2)_m$—Br, MS (ISP) 428 (M+H)$^+$.

Example 159

2-(4-Chloro-2-methyl-phenyl)-1-(2-cyclohexyl-ethyl)-5-methyl-1H-imidazole-4-carboxylic acid piperidin-1-ylamide

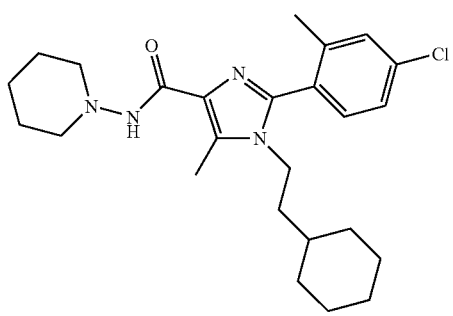

The title compound was synthesized in analogy to Example 49, using 4-chloro-2-methyl-benzylamine as $R^4$—$CH_2$—$NH_2$, 1-amino-piperidine as $R^1R^2NH$ and (bromoethyl)-cyclohexane as $R^3$—$(CH_2)_m$—Br, MS (ISP) 443 (M+H)$^+$.

Example 160

Cyclohexylmethyl-2-(3,4-dichloro-phenyl)-5-methyl-1H-imidazole-4-carboxylic acid piperidin-1-ylamide

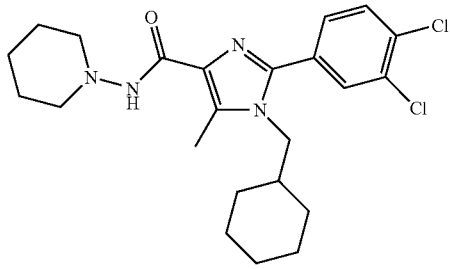

The title compound was synthesized in analogy to Example 49, using 3,4-dichloro-benzylamine as $R^4$—$CH_2$—$NH_2$, 1-amino-piperidine as $R^1R^2NH$ and (bromomethyl)-cyclohexane as $R^3$—$(CH_2)_m$—Br, MS (ISP) 449 (M+H)$^+$.

Example 161

2-(5-Chloro-2-methyl-phenyl)-1-(2-cyclohexyl-ethyl)-5-methyl-1H-imidazole-4-carboxylic acid cyclohexylamide

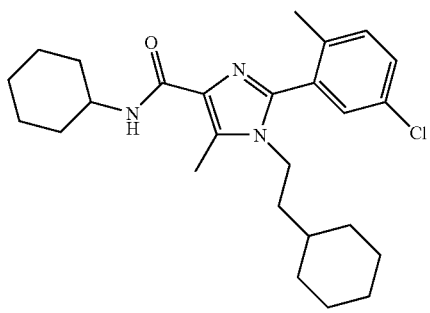

The title compound was synthesized in analogy to Example 49, using 5-chloro-2-methyl-benzylamine as $R^4$—$CH_2$—$NH_2$, cyclohexylamine as $R^1R^2NH$ and (bromoethyl)-cyclohexane as $R^3$—$(CH_2)_m$—Br, MS (ISP) 442 (M+H)$^+$.

Example 162

2-(4-Chloro-2-methyl-phenyl)-1-(2-cyclohexyl-ethyl)-5-methyl-1H-imidazole-4-carboxylic acid cyclohexylamide

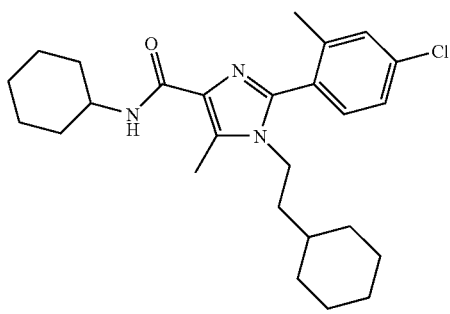

The title compound was synthesized in analogy to Example 49, using 4-chloro-2-methyl-benzylamine as $R^4$—$CH_2$—$NH_2$, cyclohexylamine as $R^1R^2NH$ and (bromoethyl)-cyclohexane as $R^3$—$(CH_2)_m$—Br, MS (ISP) 442 (M+H)$^+$.

Example 163

5-(2,5-Dimethoxy-phenyl)-2-methyl-1-phenethyl-1H-pyrrole-3-carboxylic acid cyclohexylamide

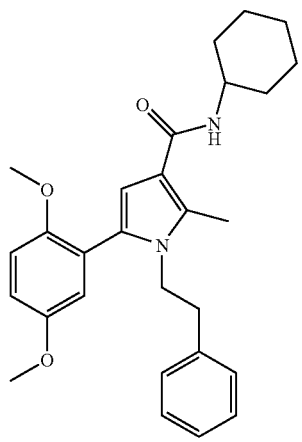

The title compound was synthesized in analogy to Example 68, using 3-oxo-butyric acid methyl ester as compound of formula R, 2-bromo-1-(2,5-dimethoxy-phenyl)-ethanone as compound of formula S, phenethylamine as $R^3$—$(CH_2)_m$—$NH_2$ and cyclohexylamine as $R^1R^2NH$, MS (ISP) 447.3 (M+H)$^+$.

Example 164

5-(2,5-Dimethoxy-phenyl)-2-methyl-1-phenethyl-1H-pyrrole-3-carboxylic acid piperidin-1-ylamide

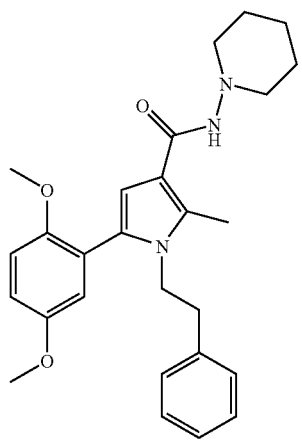

The title compound was synthesized in analogy to Example 68, using 3-oxo-butyric acid methyl ester as compound of formula R, 2-bromo-1-(2,5-dimethoxy-phenyl)-ethanone as compound of formula S, phenethylamine as R³—(CH₂)$_m$—NH₂ and 1-piperidinamine as R¹R²NH, MS (ISP) 448.3 (M+H)⁺.

Example 165

(R)-5-(3,5-Bis-trifluoromethyl-phenyl)-1-(3-fluoro-benzyl)-2-methyl-1H-pyrrole-3-carboxylic acid sec-butylamide

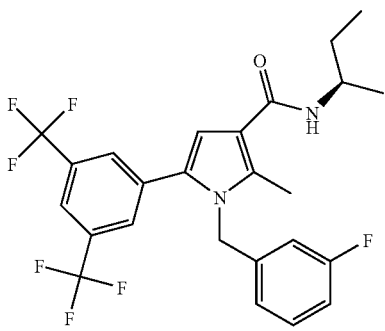

The title compound was synthesized in analogy to Example 68, using 3-oxo-butyric acid methyl ester as compound of formula R, 1-(3,5-bis-trifluoromethyl-phenyl)-2-bromo-ethanone as compound of formula S, 3-fluorobenzylamine as R³—(CH₂)$_m$—NH₂ and (R)-sec-butylamine as R¹R²NH, MS (ISP) 501.2 (M+H)⁺.

Example 166

Cyclohexylmethyl-5-(4-methoxy-2-methyl-phenyl)-2-methyl-1H-pyrrole-3-carboxylic acid cyclohexylamide

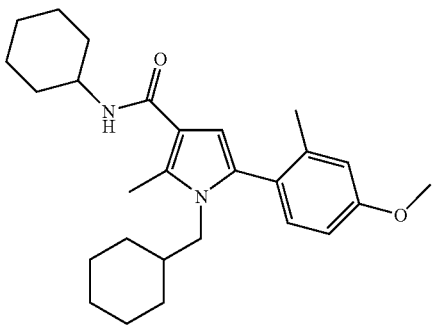

To 70 mg of 1-Cyclohexylmethyl-5-(4-hydroxy-2-methyl-phenyl)-2-methyl-1H-pyrrole-3-carboxylic acid cyclohexylamide (Example 111) in DMF was added 115 mg of potassium carbonate and 0.067 ml of methyl iodide. The reaction mixture was heated at 100° C. for 16 hours. The reaction mixture was then concentrated in vacuo and purified by column chromatography to give the title compound; MS (ISP) 423.3 (M+H)⁺.

Example 167

Cyclohexylmethyl-5-(5-fluoro-2-methoxy-phenyl)-2-methyl-1H-pyrrole-3-carboxylic acid piperidin-1-ylamide

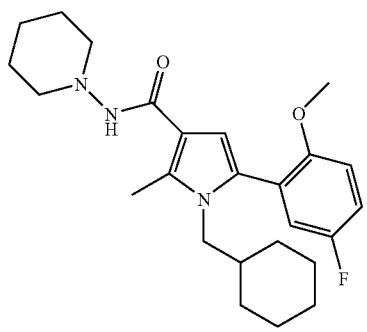

The title compound was synthesized in analogy to Example 68, using 3-oxo-butyric acid methyl ester as compound of formula R, 2-bromo-1-(5-fluoro-2-methoxy-phenyl)-ethanone as compound of formula S, c-cyclohexyl-methylamine as R³—(CH₂)$_m$—NH₂ and 1-piperidinamine as R¹R²NH, MS (ISP) 428.3 (M+H)⁺.

Example 168

-(5-Chloro-2-methoxy-phenyl)-1-cyclohexylmethyl-2-methyl-1H-pyrrole-3-carboxylic acid piperidin-1-ylamide

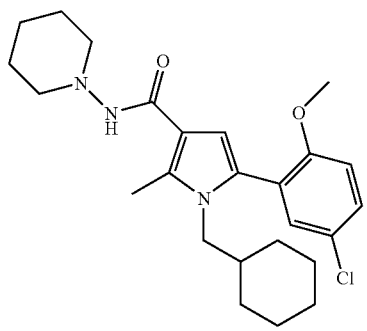

The title compound was synthesized in analogy to Example 68, using 3-oxo-butyric acid methyl ester as compound of formula R, 2-bromo-1-(5-chloro-2-methoxy-phenyl)-ethanone as compound of formula S, c-cyclohexyl-methylamine as R³—(CH₂)$_m$—NH₂ and 1-piperidinamine as R¹R²NH, MS (ISP) 444.3 (M+H)⁺.

Example 169

-(5-Chloro-2-methoxy-4-methyl-phenyl)-1-cyclohexylmethyl-2-methyl-1H-pyrrole-3-carboxylic acid piperidin-1-ylamide

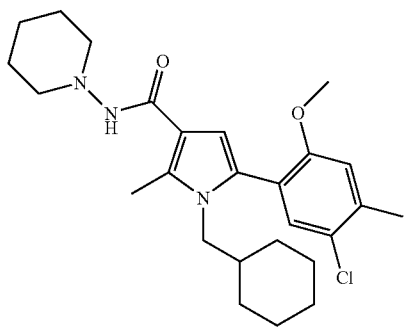

The title compound was synthesized in analogy to Example 68, using 3-oxo-butyric acid methyl ester as compound of formula R, 2-bromo-1-(5-chloro-2-methoxy-4-methyl-phenyl)-ethanone as compound of formula S, c-cyclohexyl-methylamine as $R^3$—$(CH_2)_m$—$NH_2$ and 1-piperidinamine as $R^1R^2NH$, MS (ISP) 458.3 (M+H)$^+$.

Example 170

5-(2,5-Dimethoxy-phenyl)-1-[2-(3-fluoro-phenyl)-ethyl]-2-methyl-1H-pyrrole-3-carboxylic acid cyclohexylamide

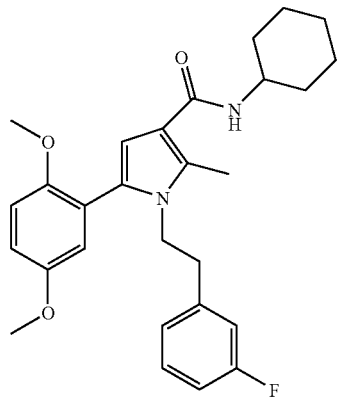

The title compound was synthesized in analogy to Example 68, using 3-oxo-butyric acid methyl ester as compound of formula R, 2-bromo-1-(2,5-dimethoxy-phenyl)-ethanone as compound of formula S, 3-fluoro-phenethylamine as $R^3$—$(CH_2)_m$—$NH_2$ and cyclohexylamine as $R^1R^2NH$, MS (ISP) 465.3 (M+H)$^+$.

Example 171

5-(2,5-Dimethoxy-phenyl)-1-[2-(3-fluoro-phenyl)-ethyl]-2-methyl-1H-pyrrole-3-carboxylic acid cyclohexylamide

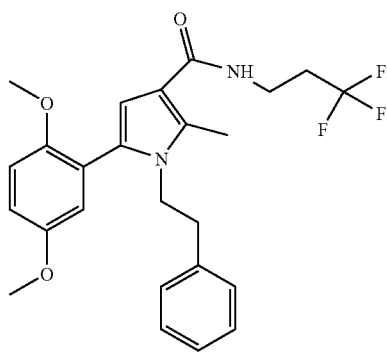

The title compound was synthesized in analogy to Example 68, using 3-oxo-butyric acid methyl ester as compound of formula R, 2-bromo-1-(2,5-dimethoxy-phenyl)-ethanone as compound of formula S, phenethylamine as $R^3$—$(CH_2)_m$—$NH_2$ and 3,3,3-trifluoro-N-propylamine as $R^1R^2NH$, MS (ISP) 461.2 (M+H)$^+$.

Example 172

5-(2,5-Dimethoxy-phenyl)-2-methyl-1-phenethyl-1H-pyrrole-3-carboxylic acid cyclopropylmethylamide

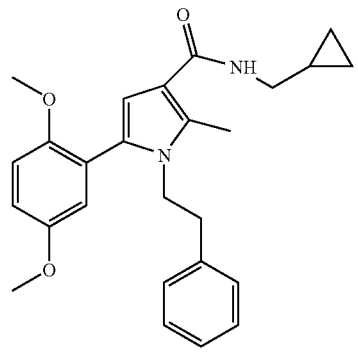

The title compound was synthesized in analogy to Example 68, using 3-oxo-butyric acid methyl ester as compound of formula R, 2-bromo-1-(2,5-dimethoxy-phenyl)-ethanone as compound of formula S, phenethylamine as $R^3$—$(CH_2)_m$—$NH_2$ and cyclopropanemethylamine as $R^1R^2NH$, MS (ISP) 419.2 (M+H)$^+$.

Example 173
Cyclohexylmethyl-5-(4-ethoxy-2-methyl-phenyl)-2-methyl-1H-pyrrole-3-carboxylic acid cyclohexylamide

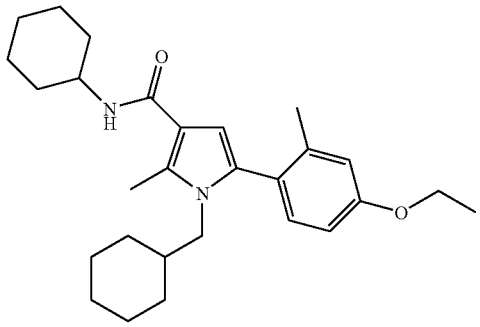

To 70 mg of 1-Cyclohexylmethyl-5-(4-hydroxy-2-methyl-phenyl)-2-methyl-1H-pyrrole-3-carboxylic acid cyclohexylamide (Example 111) in DMF was added 115 mg of potassium carbonate and 0.067 ml of ethyl iodide. The reaction mixture was heated at 100° C. for 16 hours. The reaction mixture was then concentrated in vacuo and purified by column chromatography to give the title compound; MS (ISP) 437.4 (M+H)$^+$.

Example 174
Cyclohexylmethyl-2-methyl-5-[2-methyl-4-(2,2,2-trifluoro-ethoxy)-phenyl]-1H-pyrrole-3-carboxylic acid cyclohexylamide

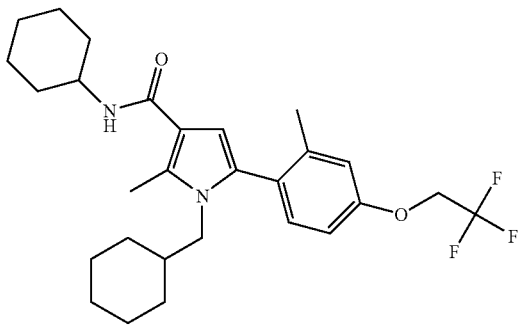

To 70 mg of 1-Cyclohexylmethyl-5-(4-hydroxy-2-methyl-phenyl)-2-methyl-1H-pyrrole-3-carboxylic acid cyclohexylamide (Example 111) in DMF was added 115 mg of potassium carbonate and 0.067 ml of 1,1,1-trifluoro-2-iodo-ethane. The reaction mixture was heated at 100° C. for 16 hours. The reaction mixture was then concentrated in vacuo and purified by column chromatography to give the title compound; MS (ISP) 491.3 (M+H)$^+$.

Example 175
5-(3,5-Bis-trifluoromethyl-phenyl)-1-cyclohexylmethyl-2,4-dimethyl-1H-pyrrole-3-carboxylic acid cyclohexylamide

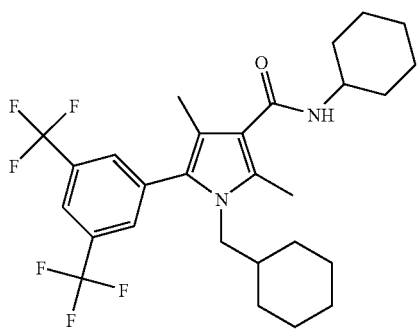

Preparation of 5-(3,5-Bis-trifluoromethyl-phenyl)-1-cyclohexylmethyl-2,4-dimethyl-1H-pyrrole-3-carboxylic acid methyl ester The title compound was prepared according to example 68, using 3-oxo-butyric acid methyl ester as compound of formula R, 1-(3,5-bis-trifluoromethyl-phenyl)-2-bromo-propan-1-one as compound of formula S and cyclohexanemethylamine, as R$^3$—(CH$_2$)$_m$—NH$_2$, MS (EI) 461.2 (M)$^+$.

Preparation of 5-(3,5-Bis-trifluoromethyl-phenyl)-1-cyclohexylmethyl-2,4-dimethyl-1H-pyrrole-3-carboxylic acid cyclohexylamide A solution of 59.5 µl (0.52 mmol) of cyclohexylamine in toluene (2 ml) was treated at RT dropwise with 0.26 µl of a 2 M solution of trimethylaluminum in toluene (0.52 mmol). The reaction solution was stirred 1 h at RT, 200 mg (0.43 mmol) of 5-(3,5-bis-trifluoromethyl-phenyl)-1-cyclohexylmethyl-2,4-dimethyl-1H-pyrrole-3-carboxylic acid methyl ester in toluene (2 ml) were added and reaction mixture was heated at 110° C. for 3 h. The mixture was then partitioned between water and ethyl acetate, the organic layer was isolated, dried over sodium sulfate and concentrated in vacuo and purified by column chromatography to give 114 mg of the title compound, MS (ISP) 529.3 (M+H)$^+$.

Example 176

1-(2-Cyclohexyl-ethyl)-5-methyl-2-(2-trifluoromethoxy-phenyl)-1H-imidazole-4-carboxylic acid piperidin-1-ylamide

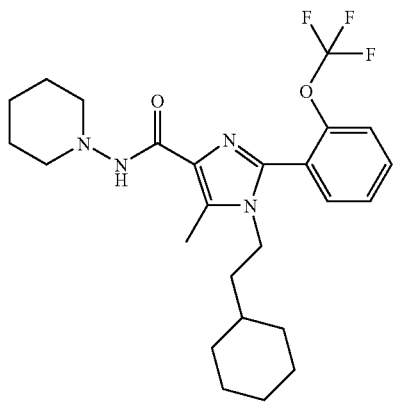

The title compound was synthesized in analogy to Example 49, using 2-trifluoromethoxy-benzylamine as R$^4$—CH$_2$—NH$_2$, 1-amino-piperidine as R$^1$R$^2$NH and (bromoethyl)-cyclohexane as R$^3$—(CH$_2$)$_m$—Br, MS (ISP) 479.2 (M+H)$^+$.

Example 177

5-(2,5-Dimethoxy-phenyl)-1-[2-(3-fluoro-phenyl)-ethyl]-2-methyl-1H-pyrrole-3-carboxylic acid (3,3,3-trifluoro-propyl)-amide

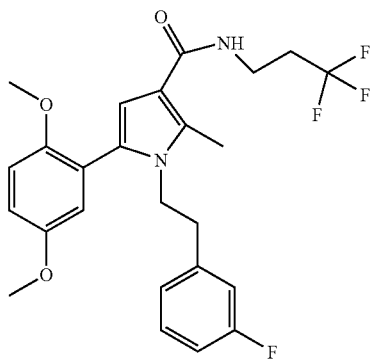

The title compound was synthesized in analogy to Example 68, using 3-oxo-butyric acid methyl ester as compound of formula R, 2-bromo-1-(2,5-dimethoxy-phenyl)-ethanone as compound of formula S, 3-fluoro-phenethylamine as $R^3$—$(CH_2)_m$—$NH_2$ and 3,3,3-trifluoro-N-propylamine as $R^1R^2NH$, MS (ISP) 479.2 $(M+H)^+$.

Example 178

5-(2,5-Dimethoxy-phenyl)-1-[2-(3-fluoro-phenyl)-ethyl]-2-methyl-1H-pyrrole-3-carboxylic acid cyclopropylmethyl-amide

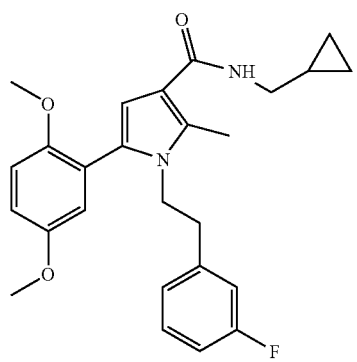

The title compound was synthesized in analogy to Example 68, using 3-oxo-butyric acid methyl ester as compound of formula R, 2-bromo-1-(2,5-dimethoxy-phenyl)-ethanone as compound of formula S, 3-fluoro-phenethylamine as $R^3$—$(CH_2)_m$—$NH_2$ and cyclopropanemethylamine as $R^1R^2NH$, MS (ISP) 437.2 $(M+H)^+$.

Example 179
Cyclohexylmethyl-5-methyl-2-(2-trifluoromethoxy-phenyl)-1H-imidazole-4-carboxylic acid piperidin-1-ylamide

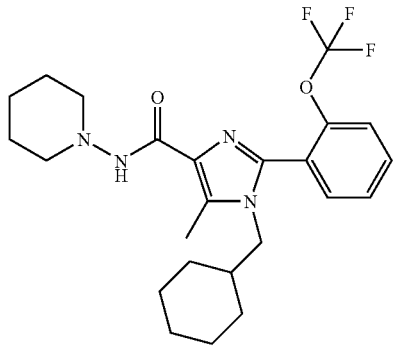

The title compound was synthesized in analogy to Example 49, using 2-trifluoromethoxy-benzylamine as $R^4$—$CH_2$—$NH_2$, 1-amino-piperidine as $R^1R^2NH$ and (bromomethyl)-cyclohexane as $R^3$—$(CH_2)_m$—$Br$, MS (ISP) 465.2 $(M+H)^+$.

Example 180
5-methyl-1-(tetrahydro-pyran-2-ylmethyl)-2-(2-trifluoromethoxy-phenyl)-1H-imidazole-4-carboxylic acid piperidin-1-ylamide

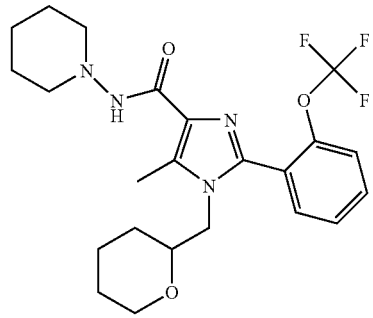

The title compound was synthesized in analogy to Example 49, using 2-trifluoromethoxy-benzylamine as $R^4$—$CH_2$—$NH_2$, 1-amino-piperidine as $R^1R^2NH$ and (bromomethyl)-tetrahydropyrane as $R^3$—$(CH_2)_m$—$Br$, MS (ISP) 467.2 $(M+H)^+$.

Example 181

Cyclohexylmethyl-2-(2-ethoxy-phenyl)-5-methyl-1H-imidazole-4-carboxylic acid piperidin-1-ylamide

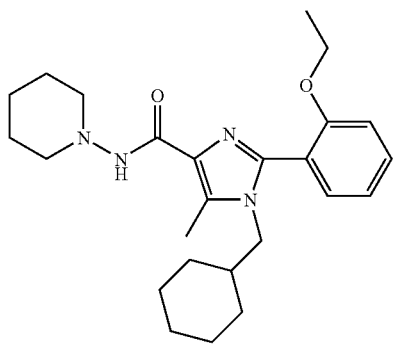

The title compound was synthesized in analogy to Example 49, using 2-ethoxy-benzylamine as $R^4$—$CH_2$—$NH_2$, 1-amino-piperidine as $R^1R^2NH$ and (bromomethyl)-cyclohexane as $R^3$—$(CH_2)_m$—Br, MS (ISP) 425.3 (M+H)$^+$.

Example 182

1-(2-Cyclohexyl-ethyl)-2-(2-ethoxy-phenyl)-5-methyl-1H-imidazole-4-carboxylic acid piperidin-1-ylamide

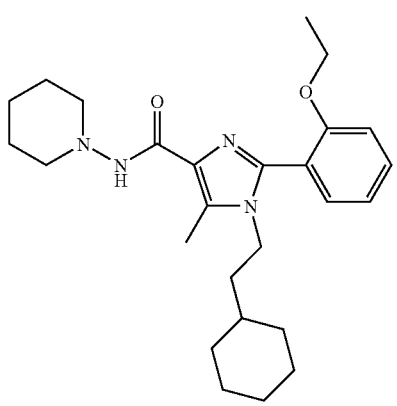

The title compound was synthesized in analogy to Example 49, using 2-ethoxy-benzylamine as $R^4$—$CH_2$—$NH_2$, 1-amino-piperidine as $R^1R^2NH$ and (bromoethyl)-cyclohexane as $R^3$—$(CH_2)_m$—Br, MS (ISP) 439.4 (M+H)$^+$.

Example 183

5-(2,5-Dimethoxy-phenyl)-1-[2-(3-fluoro-phenyl)-ethyl]-2-methyl-1H-pyrrole-3-carboxylic acid piperidin-1-ylamide

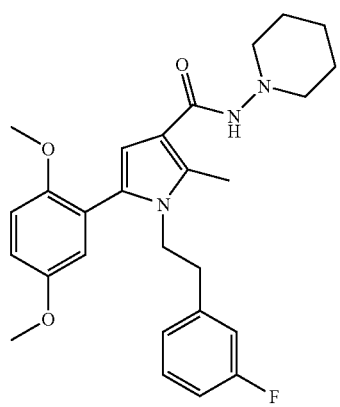

The title compound was synthesized in analogy to Example 68, using 3-oxo-butyric acid methyl ester as compound of formula R, 2-bromo-1-(2,5-dimethoxy-phenyl)-ethanone as compound of formula S, 3-fluoro-phenethylamine as $R^3$—$(CH_2)_m$—$NH_2$ and 1-piperidinamine as $R^1R^2NH$, MS (ISP) 466.3 (M+H)$^+$.

Example 184

1-[2-(2-Chloro-phenyl)-ethyl]-5-(2,5-dimethoxy-phenyl)-2-methyl-1H-pyrrole-3-carboxylic acid cyclohexylamide

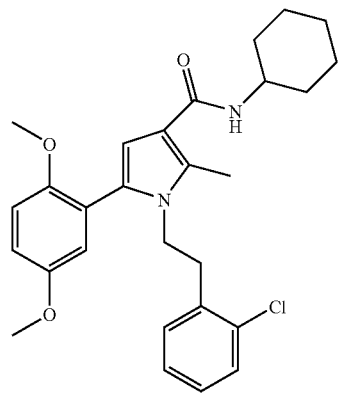

The title compound was synthesized in analogy to Example 68, using 3-oxo-butyric acid methyl ester as compound of formula R, 2-bromo-1-(2,5-dimethoxy-phenyl)-ethanone as compound of formula S, 2-chloro-phenethylamine as $R^3$—$(CH_2)_m$—$NH_2$ and cyclohexylamine as $R^1R^2NH$, MS (ISP) 481.3 (M+H)$^+$.

Example 185

1-[2-(2-Chloro-phenyl)-ethyl]-5-(2,5-dimethoxy-phenyl)-2-methyl-1H-pyrrole-3-carboxylic acid piperidin-1-ylamide

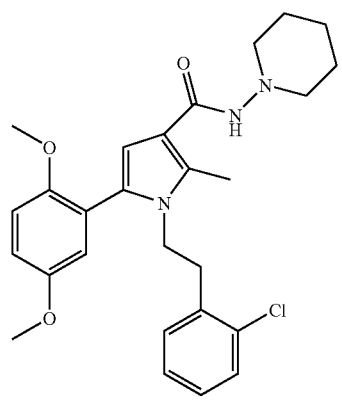

The title compound was synthesized in analogy to Example 68, using 3-oxo-butyric acid methyl ester as compound of formula R, 2-bromo-1-(2,5-dimethoxy-phenyl)-ethanone as compound of formula S, 2-chloro-phenethylamine as R³—(CH₂)ₘ—NH₂ and 1-piperidinamine as R¹R²NH, MS (ISP) 482.2 (M+H)⁺.

Example 186

5-(5-Fluoro-2-methoxy-phenyl)-2-methyl-1-phenethyl-1H-pyrrole-3-carboxylic acid cyclohexylamide

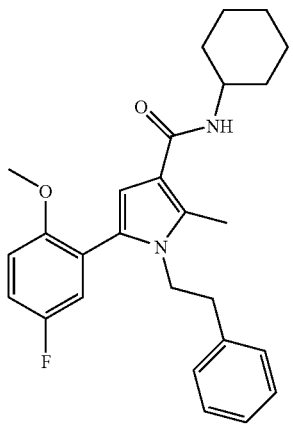

The title compound was synthesized in analogy to Example 68, using 3-oxo-butyric acid methyl ester as compound of formula R, 2-bromo-1-(5-fluoro-2-methoxy-phenyl)-ethanone as compound of formula S, phenethylamine as R³—(CH₂)ₘ—NH₂ and cyclohexylamine as R¹R²NH, MS (ISP) 435.5 (M+H)⁺.

Example 187

(S)-5-(3,5-Bis-trifluoromethyl-phenyl)-1-cyclohexylmethyl-2,4-dimethyl-1H-pyrrole-3-carboxylic acid sec-butylamide

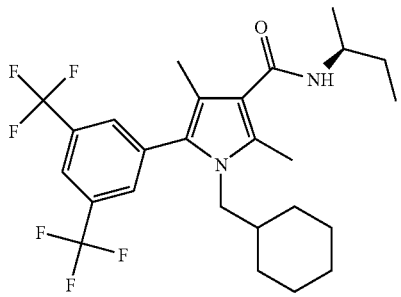

The title compound was synthesized in analogy to example 203, from 5-(3,5-bis-trifluoromethyl-phenyl)-1-cyclohexylmethyl-2,4-dimethyl-1H-pyrrole-3-carboxylic acid methyl ester and (S)-sec-butylamine as R¹R²NH, MS (ISP) 503.4 (M+H)⁺.

Example 188

5-(3,5-Bis-trifluoromethyl-phenyl)-1-cyclopropylmethyl-2-methyl-1H-pyrrole-3-carboxylic acid cyclohexylamide

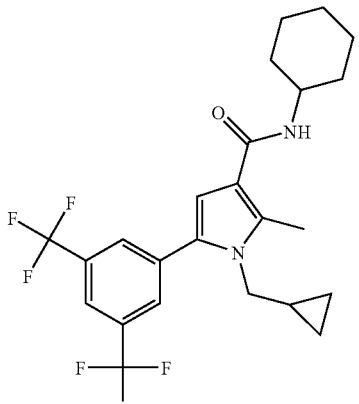

The title compound was synthesized in analogy to Example 68, using 3-oxo-butyric acid methyl ester as compound of formula R, 1-(3,5-Bis-trifluoromethyl-phenyl)-2-bromoethanone as compound of formula S, cyclopropanemethylamine as R³—(CH₂)ₘ—NH₂ and cyclohexylamine as R¹R²NH, MS (ISP) 473.2 (M+H)⁺.

Example 189

(S)-5-(3,5-Bis-trifluoromethyl-phenyl)-1-cyclopropylmethyl-2-methyl-1H-pyrrole-3-carboxylic acid sec-butylamide

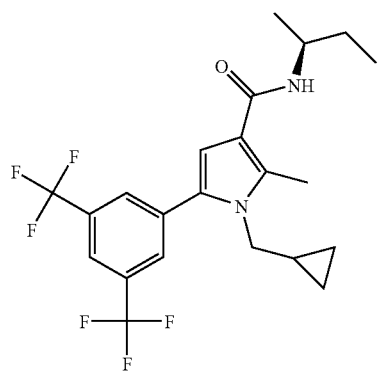

The title compound was synthesized in analogy to Example 68, using 3-oxo-butyric acid methyl ester as compound of formula R, 1-(3,5-Bis-trifluoromethyl-phenyl)-2-bromo-ethanone as compound of formula S, cyclopropanemethylamine as R³—(CH₂)ₘ—NH₂ and (S)-sec-butylamine as R¹R²NH, MS (ISP) 447.3 (M+H)⁺.

Example 190
5-(3,5-Bis-trifluoromethyl-phenyl)-1-cyclopropylmethyl-2-methyl-1H-pyrrole-3-carboxylic acid piperidin-1-ylamide

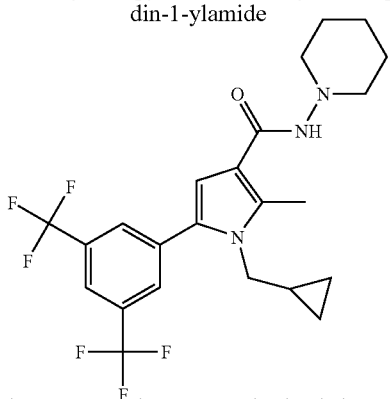

The title compound was synthesized in analogy to Example 68, using 3-oxo-butyric acid methyl ester as compound of formula R, 1-(3,5-Bis-trifluoromethyl-phenyl)-2-bromoethanone as compound of formula S, cyclopropanemethylamine as $R^3$—$(CH_2)_m$—$NH_2$ and 1-piperidinamine as $R^1R^2NH$, MS (ISP) 474.3 (M+H)$^+$.

Example 191
5-(5-Fluoro-2-methoxy-phenyl)-1-[2-(2-fluoro-phenyl)-ethyl]-2-methyl-1H-pyrrole-3-carboxylic acid piperidin-1-ylamide

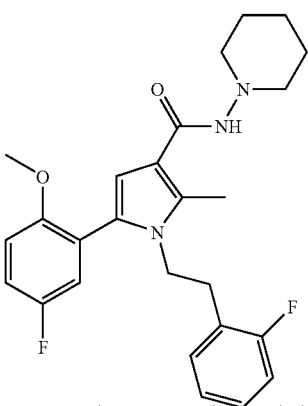

The title compound was synthesized in analogy to Example 68, using 3-oxo-butyric acid methyl ester as compound of formula R, 2-bromo-1-(5-fluoro-2-methoxy-phenyl)-ethanone as compound of formula S, 2-fluoro-phenethylamine as $R^3$—$(CH_2)_m$—$NH_2$ and 1-piperidinamine as $R^1R^2NH$, MS (ISP) 454.6 (M+H)$^+$.

Example 192
(S)-5-(5-Fluoro-2-methoxy-phenyl)-2-methyl-1-phenethyl-1H-pyrrole-3-carboxylic acid sec-butylamide

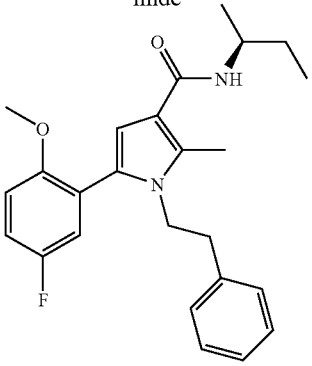

The title compound was synthesized in analogy to Example 68, using 3-oxo-butyric acid methyl ester as compound of formula R, 2-bromo-1-(5-fluoro-2-methoxy-phenyl)-ethanone as compound of formula S, phenethylamine as $R^3$—$(CH_2)_m$—$NH_2$ and (S)-sec-butylamine as $R^1R^2NH$, MS (ISP) 409.4 (M+H)$^+$.

Example 193
5-(3,5-Bis-trifluoromethyl-phenyl)-1-cyclohexylmethyl-2,4-dimethyl-1H-pyrrole-3-carboxylic acid piperidin-1-ylamide

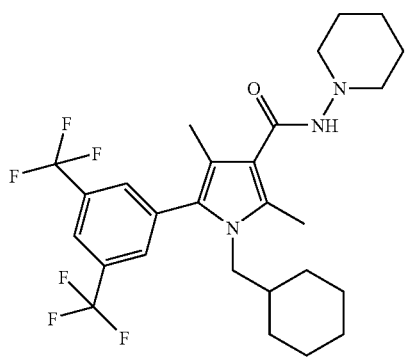

The title compound was synthesized in analogy to example 203, from 5-(3,5-bis-trifluoromethyl-phenyl)-1-cyclohexyl-methyl-2,4-dimethyl-1H-pyrrole-3-carboxylic acid methyl ester and 1-piperidinamine as $R^1R^2NH$, MS (ISP) 530.4 (M+H)$^+$.

Example 194
Cyclopropylmethyl-5-(5-fluoro-2-methoxy-phenyl)-2-methyl-1H-pyrrole-3-carboxylic acid cyclohexylamide

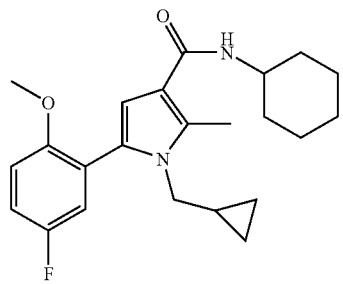

The title compound was synthesized in analogy to Example 68, using 3-oxo-butyric acid methyl ester as compound of formula R, 2-bromo-1-(5-fluoro-2-methoxy-phenyl)-ethanone as compound of formula S, cyclopropanemethylamine as $R^3$—$(CH_2)_m$—$NH_2$ and cyclohexylamine as $R^1R^2NH$, MS (ISP) 385.4 (M+H)$^+$.

Example 195

Cyclopropylmethyl-5-(5-fluoro-2-methoxy-phenyl)-2-methyl-1H-pyrrole-3-carboxylic acid piperidin-1-ylamide

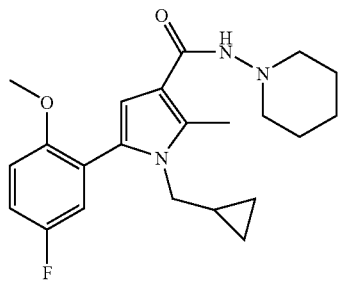

The title compound was synthesized in analogy to Example 68, using 3-oxo-butyric acid methyl ester as compound of formula R, 2-bromo-1-(5-fluoro-2-methoxy-phenyl)-ethanone as compound of formula S, cyclopropanemethylamine as $R^3$—$(CH_2)_m$—$NH_2$ and 1-piperidinamine as $R^1R^2NH$, MS (ISP) 386.4 (M+H)$^+$.

Example 196

(R)-1-Cyclopropylmethyl-5-(5-fluoro-2-methoxy-phenyl)-2-methyl-1H-pyrrole-3-carboxylic acid sec-butylamide

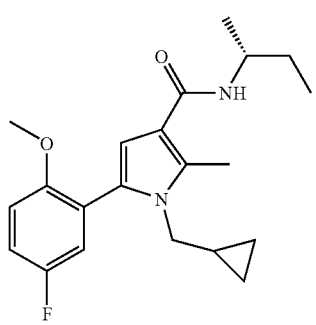

The title compound was synthesized in analogy to Example 68, using 3-oxo-butyric acid methyl ester as compound of formula R, 2-bromo-1-(5-fluoro-2-methoxy-phenyl)-ethanone as compound of formula S, cyclopropanemethylamine as $R^3$—$(CH_2)_m$—$NH_2$ and (R)-sec-butylamine as $R^1R^2NH$, MS (ISP) 359.3 (M+H)$^+$.

Example 197

Cyclopropylmethyl-5-(5-fluoro-2-methoxy-phenyl)-2-methyl-1H-pyrrole-3-carboxylic acid (trans-2-hydroxy-cyclohexyl)-amide

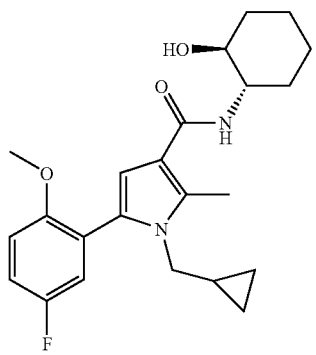

The title compound was synthesized in analogy to Example 68, using 3-oxo-butyric acid methyl ester as compound of formula R, 2-bromo-1-(5-fluoro-2-methoxy-phenyl)-ethanone as compound of formula S, cyclopropanemethylamine as $R^3$—$(CH_2)_m$—$NH_2$ and trans-2-hydroxy-cyclohexylamine as $R^1R^2NH$, MS (ISP) 401.6 (M+H)$^+$.

Example 198

Cyclopropylmethyl-5-(5-fluoro-2-methoxy-phenyl)-2-methyl-1H-pyrrole-3-carboxylic acid (3,3,3-trifluoro-propyl)-amide

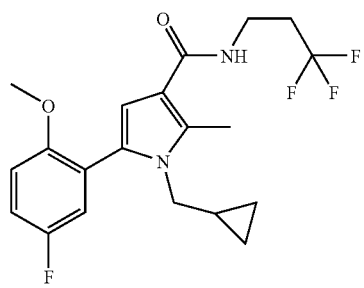

The title compound was synthesized in analogy to Example 68, using 3-oxo-butyric acid methyl ester as compound of formula R, 2-bromo-1-(5-fluoro-2-methoxy-phenyl)-ethanone as compound of formula S, cyclopropanemethylamine as $R^3$—$(CH_2)_m$—$NH_2$ and 3,3,3-trifluoro-N-propylamine as $R^1R^2NH$, MS (ISP) 399.4 (M+H)$^+$.

Example 199

Cyclohexylmethyl-5-(2,5-dichloro-pyridin-3-yl)-2-methyl-1H-pyrrole-3-carboxylic acid cyclohexylamide

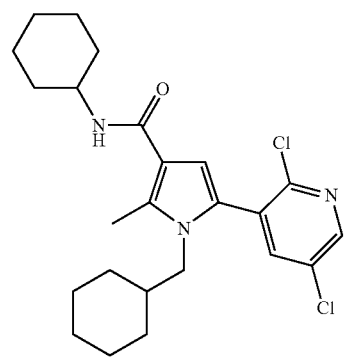

Preparation of 1-(2-Ethyl-phenyl)-ethanone

The title compound was synthesized from 2,5-dichloro-nicotinoyl chloride [78686-87-0] following the procedure described by Steven Nahm and Steven M. Weinreb, *Tetrahedron Lett.*, vol 22, 39, 1981, 3815-3818.

Preparation of
2-bromo-1-(2,5-dichloro-pyridin-3-yl)-ethanone

The title compound was synthesized from 1-(2-Ethyl-phenyl)-ethanone following the procedure described by D. W. Robertson et. Al, *J. Med. Chem.*, 29, 1986, 1577-1586).

Preparation of 1-Cyclohexylmethyl-5-(2,5-dichloro-pyridin-3-yl)-2-methyl-1H-pyrrole-3-carboxylic acid cyclohexylamide The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(2,5-dichloro-pyridin-3-yl)-ethanone, MS (ISP) 448.2 $(M+H)^+$.

Example 200

Cyclohexylmethyl-2-methyl-5-(3-methyl-pyridin-2-yl)-1H-pyrrole-3-carboxylic acid cyclohexylamide

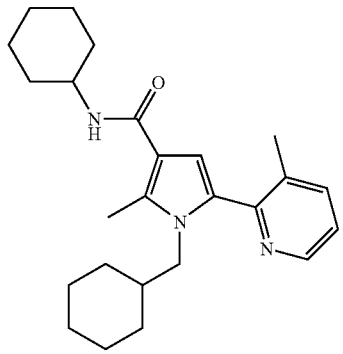

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(3-methyl-pyridin-2-yl)-ethanone [220270-42-8], MS (ISP) 394.3 $(M+H)^+$.

Example 201

Cyclohexylmethyl-2-methyl-5-(2-methyl-pyridin-3-yl)-1H-pyrrole-3-carboxylic acid cyclohexylamide

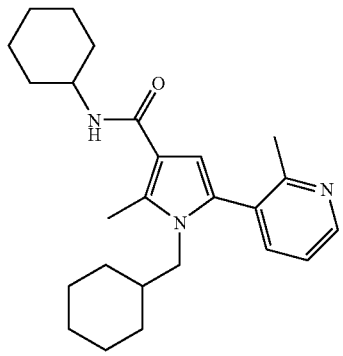

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(2-methyl-pyridin-3-yl)-ethanone [67279-27-0], MS (ISP) 394.3 $(M+H)^+$.

Example 202

Cyclohexylmethyl-2-methyl-5-(3-methyl-pyrazin-2-yl)-1H-pyrrole-3-carboxylic acid cyclohexylamide

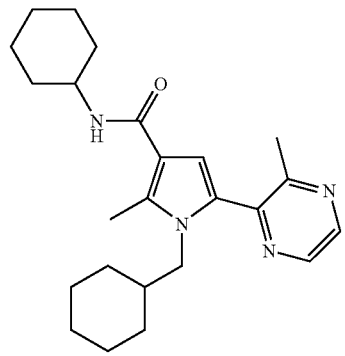

The title compound was synthesized in analogy to Example 1, using cyclohexylamine as $R^1R^2NH$, c-cyclohexyl-methylamine as $R^3$—$(CH_2)_m$—$NH_2$ and 2-bromo-1-(3-methyl-pyrazin-2-yl)-ethanone (available from 1-(3-methyl-pyrazin-2-yl)-ethanone [23787-80-6] following the procedure described by D. W. Robertson et. Al, *J. Med. Chem.*, 29, 1986, 1577-1586); MS (ISP) 395.4 $(M+H)^+$.

Example 203

5-(5-Chloro-2-fluoro-phenyl)-1-cyclohexylmethyl-2-methyl-1H-pyrrole-3-carboxylic acid cyclohexylamide

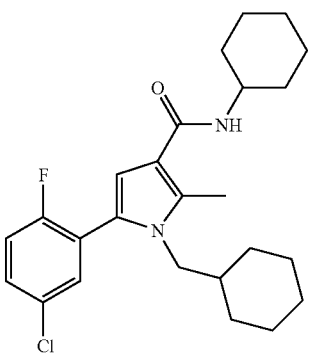

The title compound was synthesized in analogy to Example 68, using cyclohexylamine as $R^1R^2NH$, c-cyclohexyl-methylamine as $R^3$—$(CH_2)_m$—$NH_2$ and 2-bromo-1-(5-chloro-2-fluoro-phenyl)-ethanone, MS (ISP) 431.3 $(M+H)^+$.

Example 204

5-(2,5-Bis-trifluoromethyl-phenyl)-1-cyclohexylmethyl-2-methyl-1H-pyrrole-3-carboxylic acid cyclohexylamide

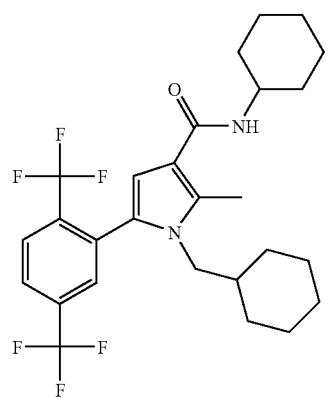

The title compound was synthesized in analogy to Example 68, using cyclohexylamine as $R^1R^2NH$, c-cyclohexyl-methylamine as $R^3$—$(CH_2)_m$—$NH_2$ and 1-(2,5-bis-trifluoromethyl-phenyl)-2-bromo-ethanone, MS (ISP) 515.2 $(M+H)^+$.

Example 205

5-(4-Chloro-2-fluoro-phenyl)-1-cyclohexylmethyl-2-methyl-1H-pyrrole-3-carboxylic acid cyclohexylamide

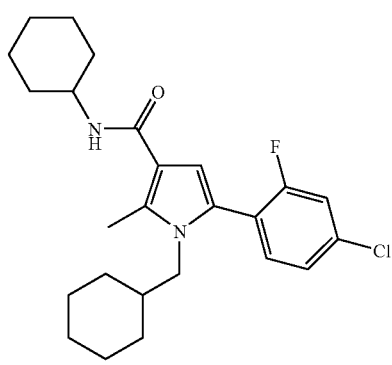

The title compound was synthesized in analogy to Example 68, using cyclohexylamine as $R^1R^2NH$, c-cyclohexyl-methylamine as $R^3$—$(CH_2)_m$—$NH_2$ and 2-bromo-1-(4-chloro-2-fluorophenyl)-ethanone, MS (ISP) 431.4 $(M+H)^+$.

Example 206

Cyclopropylmethyl-2-methyl-5-(4-trifluoromethoxy-phenyl)-1H-pyrrole-3-carboxylic acid piperidin-1-ylamide

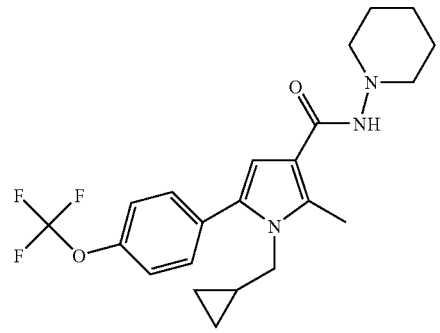

The title compound was synthesized in analogy to Example 68, using 3-oxo-butyric acid methyl ester as compound of formula R, 2-bromo-1-(4-trifluoromethoxy-phenyl)-ethanone as compound of formula S, cyclopropanemethylamine as R3-(CH2)m-NH2 and 1-piperidinamine as R1R2NH, MS (ISP) 422.3 $(M+H)^+$.

Example 207

Cyclohexylmethyl-5-(2,4-dichloro-phenyl)-2-methyl-1H-pyrrole-3-carboxylic acid cyclohexylamide

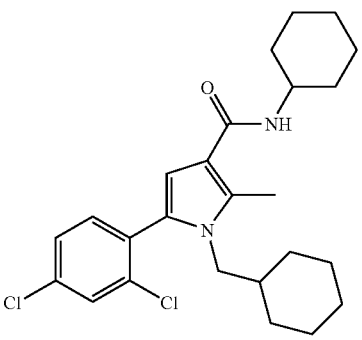

The title compound was synthesized in analogy to Example 68, using 3-oxo-butyric acid methyl ester as compound of formula R, 2-bromo-1-(2,4-dichlorophenyl)-ethanone as compound of formula S, c-cyclohexyl-methylamine as $R^3$—$(CH_2)_m$—$NH_2$ and cyclohexylamine as $R^1R^2NH$, MS (ISP) 447.4 $(M+H)^+$.

Example 208

Cyclohexylmethyl-5-(2,4-dichloro-phenyl)-2-methyl-1H-pyrrole-3-carboxylic acid ((1SR,2RS)-2-hydroxy-cyclohexyl)-amide

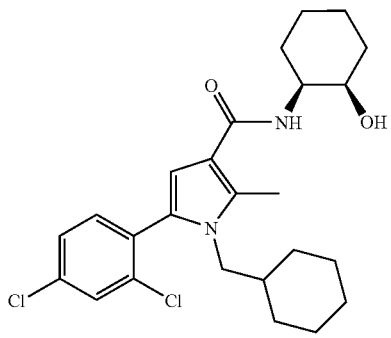

The title compound was synthesized in analogy to Example 68, using 3-oxo-butyric acid methyl ester as compound of formula R, 2-bromo-1-(2,4-dichlorophenyl)-ethanone as compound of formula S, c-cyclohexyl-methylamine as $R^3$—$(CH_2)_m$—$NH_2$ and cis-2-aminocyclohexanol as $R^1R^2NH$, MS (ISP) 463.4 (M+H)$^+$.

Example 209

Cyclohexylmethyl-5-(2,4-dichloro-phenyl)-2-methyl-1H-pyrrole-3-carboxylic acid ((1S,2S)-2-hydroxy-cyclohexyl)-amide

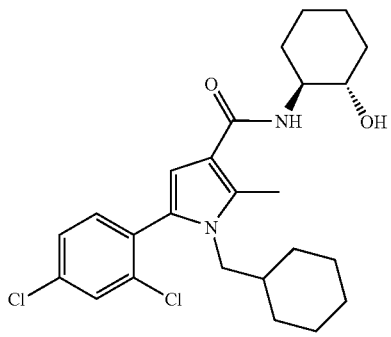

The title compound was synthesized in analogy to Example 68, using 3-oxo-butyric acid methyl ester as compound of formula R, 2-bromo-1-(2,4-dichlorophenyl)-ethanone as compound of formula S, c-cyclohexyl-methylamine as $R^3$—$(CH_2)_m$—$NH_2$ and (1S,2S)-2-aminocyclohexanol as $R^1R^2NH$, MS (ISP) 463.3 (M+H)$^+$.

Example 210

Cyclohexylmethyl-5-(2,4-dichloro-phenyl)-2-methyl-1H-pyrrole-3-carboxylic acid ((1R,2R)-2-hydroxy-cyclohexyl)-amide

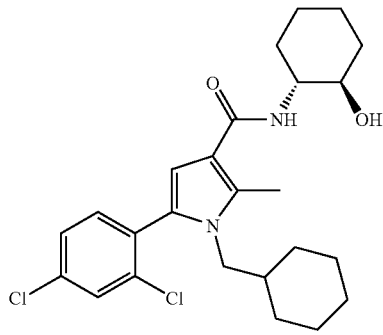

The title compound was synthesized in analogy to Example 68, using 3-oxo-butyric acid methyl ester as compound of formula R, 2-bromo-1-(2,4-dichlorophenyl)-ethanone as compound of formula S, c-cyclohexyl-methylamine as $R^3$—$(CH_2)_m$—$NH_2$ and (1R,2R)-2-aminocyclohexanol as $R^1R^2NH$, MS (ISP) 463.6 (M+H)$^+$.

Example 211

Cyclohexylmethyl-5-(2,5-dichloro-phenyl)-2-methyl-1H-pyrrole-3-carboxylic acid cyclohexylamide

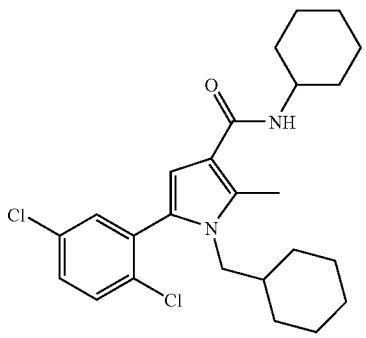

The title compound was synthesized in analogy to Example 68, using 3-oxo-butyric acid methyl ester as compound of formula R, 2-bromo-1-(2,5-dichlorophenyl)-ethanone as compound of formula S, c-cyclohexyl-methylamine as $R^3$—$(CH_2)_m$—$NH_2$ and cyclohexylamine as $R^1R^2NH$, MS (ISP) 447.5 (M+H)$^+$.

Example 212

Cyclohexylmethyl-5-(2,5-dichloro-phenyl)-2-methyl-1H-pyrrole-3-carboxylic acid ((1RS,2RS)-2-hydroxy-cyclohexyl)-amide

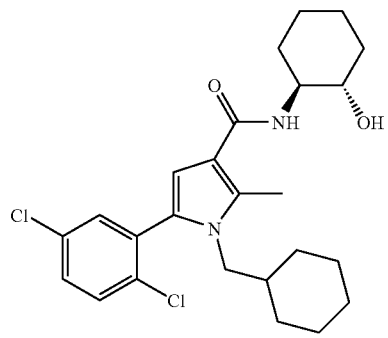

The title compound was synthesized in analogy to Example 68, using 3-oxo-butyric acid methyl ester as compound of formula R, 2-bromo-1-(2,5-dichlorophenyl)-ethanone as compound of formula S, c-cyclohexyl-methylamine as $R^3$—$(CH_2)_m$—$NH_2$ and trans-2-aminocyclohexanol as $R^1R^2NH$, MS (ISP) 463.4 (M+H)$^+$.

Example 213

Cyclohexylmethyl-5-(2,5-dichloro-phenyl)-2-methyl-1H-pyrrole-3-carboxylic acid [(R)-1-(tetrahydro-furan-2-yl)methyl]-amide

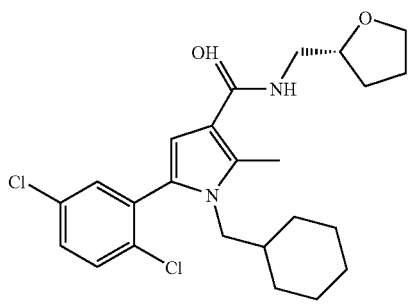

The title compound was synthesized in analogy to Example 68, using 3-oxo-butyric acid methyl ester as compound of formula R, 2-bromo-1-(2,5-dichlorophenyl)-ethanone as compound of formula S, c-cyclohexyl-methylamine as $R^3$—$(CH_2)_m$—$NH_2$ and (R)-tetrahydrofurfurylamine as $R^1R^2NH$, MS (ISP) 449.5 (M+H)$^+$.

Example 214

Cyclohexylmethyl-5-(2,5-dichloro-phenyl)-2-methyl-1H-pyrrole-3-carboxylic acid [(S)-1-(tetrahydro-furan-2-yl)methyl]-amide

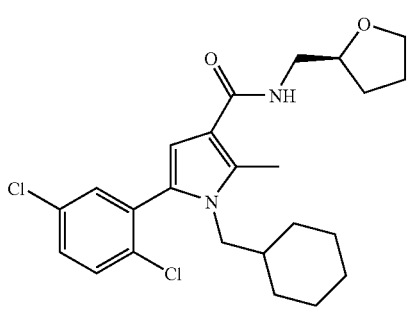

The title compound was synthesized in analogy to Example 68, using 3-oxo-butyric acid methyl ester as compound of formula R, 2-bromo-1-(2,5-dichlorophenyl)-ethanone as compound of formula S, c-cyclohexyl-methylamine as $R^3$—$(CH_2)_m$—$NH_2$ and (S)-tetrahydrofurfurylamine as $R^1R^2NH$, MS (ISP) 449.5 (M+H)$^+$.

Example 215

Cyclohexylmethyl-5-(2,5-difluoro-phenyl)-2-methyl-1H-pyrrole-3-carboxylic acid cyclohexylamide

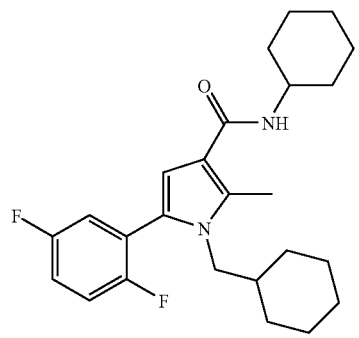

The title compound was synthesized in analogy to Example 68, using 3-oxo-butyric acid methyl ester as compound of formula R, 2-bromo-1-(2,5-difluorophenyl)-ethanone as compound of formula S, c-cyclohexyl-methylamine as $R^3$—$(CH_2)_m$—$NH_2$ and cyclohexylamine as $R^1R^2NH$, MS (ISP) 415.5 (M+H)$^+$.

Example 216

Cyclohexylmethyl-5-(2,5-difluoro-phenyl)-2-methyl-1H-pyrrole-3-carboxylic acid ((1RS,2RS)-2-hydroxy-cyclohexyl)-amide

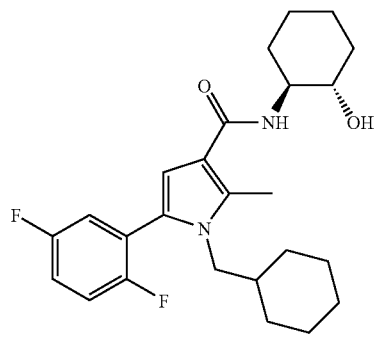

The title compound was synthesized in analogy to Example 68, using 3-oxo-butyric acid methyl ester as compound of formula R, 2-bromo-1-(2,5-difluorophenyl)-ethanone as compound of formula S, c-cyclohexyl-methylamine as $R^3$—$(CH_2)_m$—$NH_2$ and trans-2-aminocyclohexanol as $R^1R^2NH$, MS (ISP) 431.5 (M+H)$^+$.

Example 217

Cyclohexylmethyl-5-(2,5-difluoro-phenyl)-2-methyl-1H-pyrrole-3-carboxylic acid ((1RS,2SR)-2-hydroxy-cyclohexylmethyl)-amide

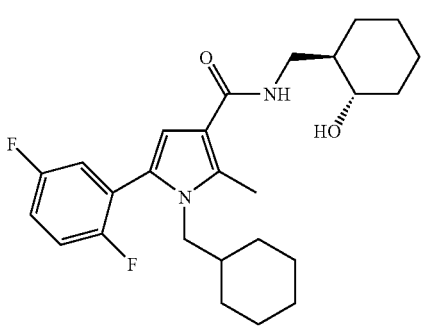

The title compound was synthesized in analogy to Example 68, using 3-oxo-butyric acid methyl ester as compound of formula R, 2-bromo-1-(2,5-difluorophenyl)-ethanone as compound of formula S, c-cyclohexyl-methylamine as $R^3$—$(CH_2)_m$—$NH_2$ and trans-2-aminomethyl-1-cyclohexanol as $R^1R^2NH$, MS (ISP) 445.5 (M+H)$^+$.

Example 218

Cyclohexylmethyl-5-(2,5-difluoro-phenyl)-2-methyl-1H-pyrrole-3-carboxylic acid ((1RS,2RS)-2-hydroxy-cyclohexylmethyl)-amide

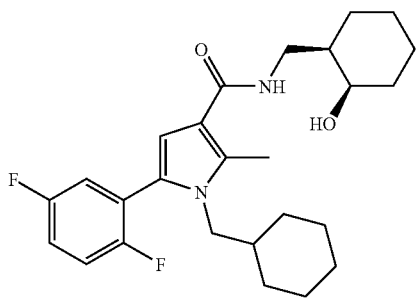

The title compound was synthesized in analogy to Example 68, using 3-oxo-butyric acid methyl ester as compound of formula R, 2-bromo-1-(2,5-difluorophenyl)-ethanone as compound of formula S, c-cyclohexyl-methylamine as $R^3$—$(CH_2)_m$—$NH_2$ and cis-2-aminomethyl-1-cyclohexanol as $R^1R^2NH$, MS (ISP) 445.4 (M+H)$^+$.

Example 219

Cyclohexylmethyl-5-(2,4-dichloro-5-fluoro-phenyl)-2-methyl-1H-pyrrole-3-carboxylic acid cyclohexylamide

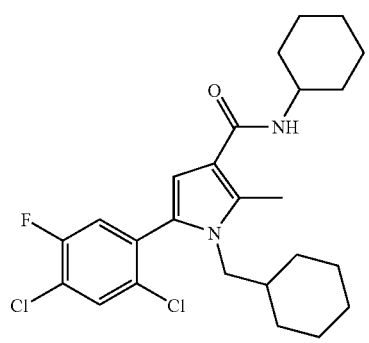

The title compound was synthesized in analogy to Example 68, using 3-oxo-butyric acid methyl ester as compound of formula R, 2-bromo-1-(2,4-dichloro-5-fluorophenyl)-ethanone as compound of formula S, c-cyclohexyl-methylamine as $R^3$—$(CH_2)_m$—$NH_2$ and cyclohexylamine as $R^1R^2NH$, MS (ISP) 465.4 (M+H)$^+$.

Example 220

Cyclohexylmethyl-5-(2,4-dichloro-5-fluoro-phenyl)-2-methyl-1H-pyrrole-3-carboxylic acid ((1RS,2RS)-2-hydroxy-cyclohexyl)-amide

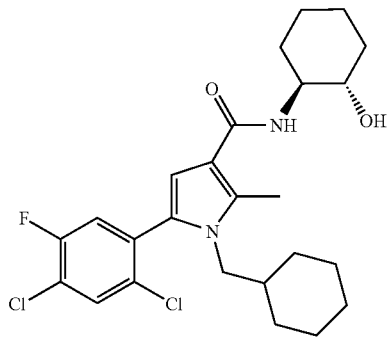

The title compound was synthesized in analogy to Example 68, using 3-oxo-butyric acid methyl ester as compound of formula R, 2-bromo-1-(2,4-dichloro-5-fluorophenyl)-ethanone as compound of formula S, c-cyclohexyl-methylamine as $R^3$—$(CH_2)_m$—$NH_2$ and trans-2-aminocyclohexanol as $R^1R^2NH$, MS (ISP) 481.4 $(M+H)^+$.

Example 221

Cyclohexylmethyl-5-(2,4-dichloro-5-fluoro-phenyl)-2-methyl-1H-pyrrole-3-carboxylic acid (1-hydroxy-cyclohexylmethyl)-amide

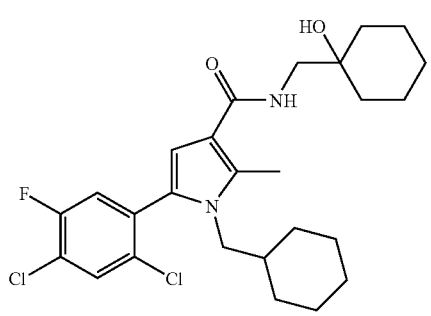

The title compound was synthesized in analogy to Example 68, using 3-oxo-butyric a c i d methyl ester as compound of formula R, 2-bromo-1-(2,4-dichloro-5-fluorophenyl)-ethanone as compound of formula S, c-cyclohexyl-methylamine as $R^3$—$(CH_2)_m$—$NH_2$ and 1-aminomethyl-1-cyclohexanol as $R^1R^2NH$, MS (ISP) 495.5 $(M+H)^+$.

Example 222

Cyclohexylmethyl-5-(2,4-dichloro-5-fluoro-phenyl)-2-methyl-1H-pyrrole-3-carboxylic acid cyclopropyl-methyl-amide

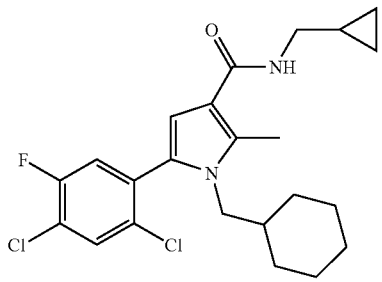

The title compound was synthesized in analogy to Example 68, using 3-oxo-butyric acid methyl ester as compound of formula R, 2-bromo-1-(2,4-dichloro-5-fluorophenyl)-ethanone as compound of formula S, c-cyclohexyl-methylamine as $R^3$—$(CH_2)_m$—$NH_2$ and 1-aminomethyl-cyclopropane as $R^1R^2NH$, MS (ISP) 437.5 $(M+H)^+$.

Example 223

Cyclohexylmethyl-2-methyl-5-(2-trifluoromethoxy-phenyl)-1H-pyrrole-3-carboxylic acid cyclohexylamide

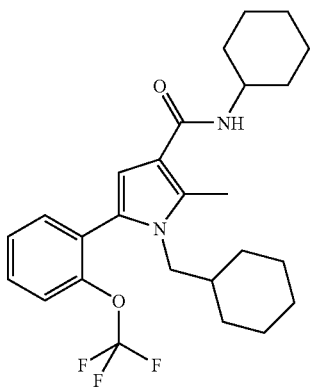

The title compound was synthesized in analogy to Example 68, using 3-oxo-butyric acid methyl ester as compound of formula R, 2-bromo-1-(2-(trifluoromethoxy)phenyl)-ethanone as compound of formula S, c-cyclohexyl-methylamine as $R^3$—$(CH_2)_m$—$NH_2$ and cyclohexylamine as $R^1R^2NH$, MS (ISP) 463.6 $(M+H)^+$.

Example 224

Cyclohexylmethyl-2-methyl-5-(2-trifluoromethoxy-phenyl)-1H-pyrrole-3-carboxylic acid ((1RS,2RS)-2-hydroxy-cyclohexyl)-amide

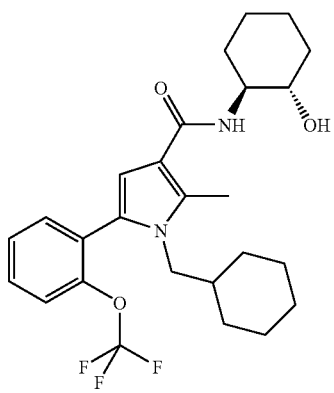

The title compound was synthesized in analogy to Example 68, using 3-oxo-butyric acid methyl ester as compound of formula R, 2-bromo-1-(2-(trifluoromethoxy)phenyl)-ethanone as compound of formula S, c-cyclohexyl-methylamine as $R^3$—$(CH_2)_m$—$NH_2$ and trans-2-aminocyclohexanol as $R^1R^2NH$, MS (ISP) 479.6 (M+H)$^+$.

Example 225

Cyclohexylmethyl-2-methyl-5-(2-trifluoromethoxy-phenyl)-1H-pyrrole-3-carboxylic acid cyclohexylmethyl-amide

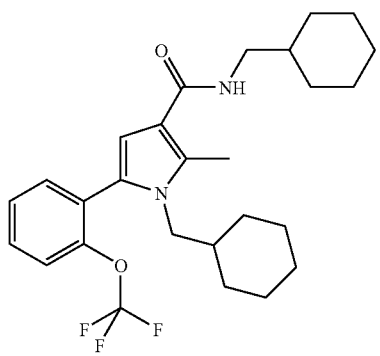

The title compound was synthesized in analogy to Example 68, using 3-oxo-butyric acid methyl ester as compound of formula R, 2-bromo-1-(2-(trifluoromethoxy)phenyl)-ethanone as compound of formula S, c-cyclohexyl-methylamine as $R^3$—$(CH_2)_m$—$NH_2$ and c-cyclohexyl-methylamine as $R^1R^2NH$, MS (ISP) 477.4 (M+H)$^+$.

Example 226

Cyclohexylmethyl-2-methyl-5-(2-trifluoromethoxy-phenyl)-1H-pyrrole-3-carboxylic acid cycloheptylmethyl-amide

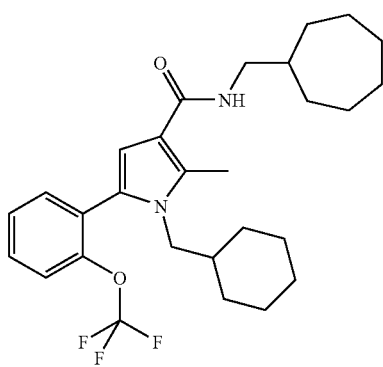

The title compound was synthesized in analogy to Example 68, using 3-oxo-butyric acid methyl ester as compound of formula R, 2-bromo-1-(2-(trifluoromethoxy)phenyl)-ethanone as compound of formula S, c-cyclohexyl-methylamine as $R^3$—$(CH_2)_m$—$NH_2$ and c-cycloheptyl-methylamine as $R^1R^2NH$, MS (ISP) 491.5 (M+H)$^+$.

Example 227

Cyclohexylmethyl-5-(2-fluoro-5-trifluoromethyl-phenyl)-2-methyl-1H-pyrrole-3-carboxylic acid cyclohexylamide

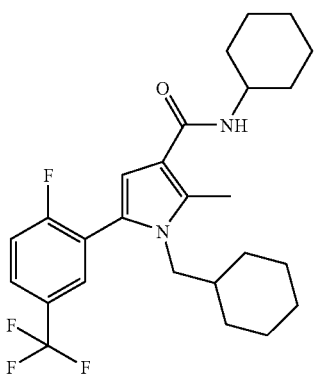

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, c-cyclohexyl-methylamine as $R^3$—$(CH_2)_m$—$NH_2$ and cyclohexylamine as $R^1R^2NH$, MS (ISP) 465.5 (M+H)$^+$.

Example 228

Cyclohexylmethyl-5-(2-fluoro-5-trifluoromethyl-phenyl)-2-methyl-1H-pyrrole-3-carboxylic acid ((1RS,2RS)-2-hydroxy-cyclohexyl)-amide

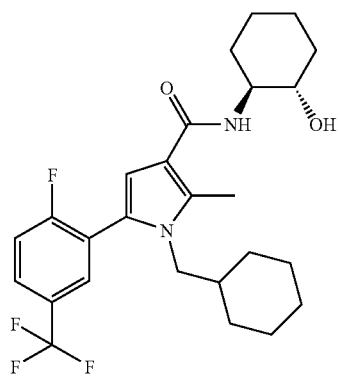

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, c-cyclohexyl-methylamine as $R^3$—$(CH_2)_m$—$NH_2$ and trans-2-aminocyclohexanol as $R^1R^2NH$, MS (ISP) 481.5 $(M+H)^+$.

Example 229

Cyclohexylmethyl-5-(2-fluoro-5-trifluoromethyl-phenyl)-2-methyl-1H-pyrrole-3-carboxylic acid piperidin-1-ylamide

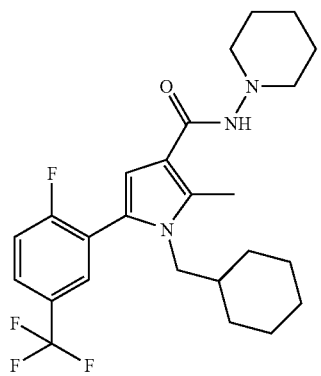

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, c-cyclohexyl-methylamine as $R^3$—$(CH_2)_m$—$NH_2$ and N-aminopiperidine as $R^1R^2NH$, MS (ISP) 466.5 $(M+H)^+$.

Example 230

Cyclohexylmethyl-5-(2-fluoro-5-trifluoromethyl-phenyl)-2-methyl-1H-pyrrole-3-carboxylic acid (tetrahydro-furan-2-ylmethyl)-amide

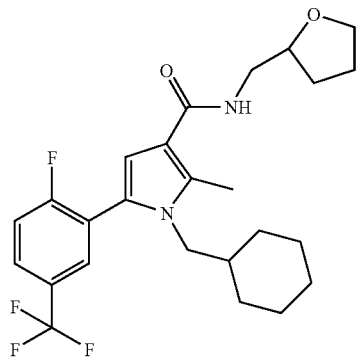

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, c-cyclohexyl-methylamine as $R^3$—$(CH_2)_m$—$NH_2$ and rac-tetrahydrofurfurylamine as $R^1R^2NH$, MS (ISP) 467.5 $(M+H)^+$.

Example 231

5-(5-Chloro-2-methoxy-4-methyl-phenyl)-1-cyclopropylmethyl-2-methyl-1H-pyrrole-3-carboxylic acid cyclohexylamide

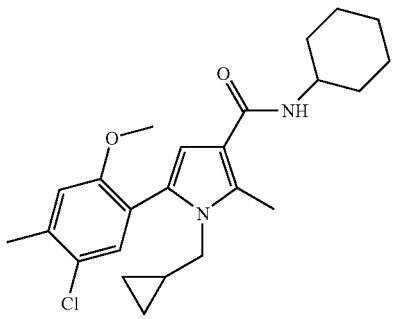

The title compound was synthesized in analogy to Example 68, using 3-oxo-butyric acid methyl ester as compound of formula R, 2-bromo-1-(5-chloro-2-methoxy-4-methyl-phenyl)-ethanone as compound of formula S, cyclopropanemethylamine as $R^3$—$(CH_2)_m$—$NH_2$ and cyclohexylamine as $R^1R^2NH$, MS (ISP) 415.5 $(M+H)^+$.

Example 232

5-(2-Chloro-5-trifluoromethyl-phenyl)-1-cyclohexyl-methyl-2-methyl-1H-pyrrole-3-carboxylic acid cyclohexylamide

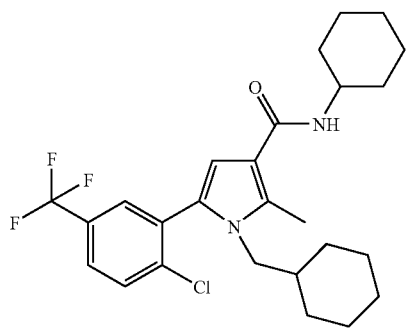

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, c-cyclohexyl-methylamine as $R^3$—$(CH_2)_m$—$NH_2$ and cyclohexylamine as $R^1R^2NH$, MS (ISP) 481.5 $(M+H)^+$.

Example 233

5-(2-Chloro-5-trifluoromethyl-phenyl)-1-cyclohexyl-methyl-2-methyl-1H-pyrrole-3-carboxylic acid ((1RS,2RS)-2-hydroxy-cyclohexyl)-amide

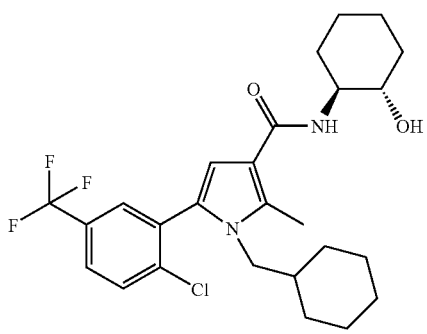

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, c-cyclohexyl-methylamine as $R^3$—$(CH_2)_m$—$NH_2$ and trans-2-amino-cyclohexanol as $R^1R^2NH$, MS (ISP) 497.5 $(M+H)^+$.

Example 234

5-(2-Chloro-5-trifluoromethyl-phenyl)-1-cyclohexyl-methyl-2-methyl-1H-pyrrole-3-carboxylic acid (2,2-dimethyl-[1,3]dioxolan-4-ylmethyl)-amide

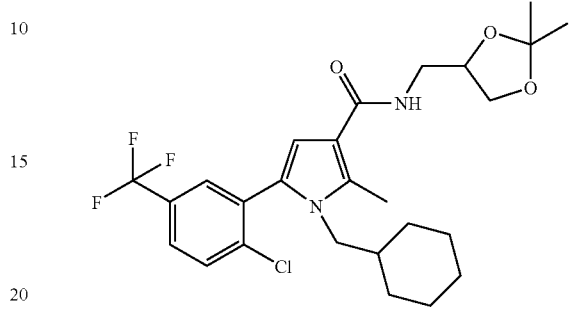

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, c-cyclohexyl-methylamine as $R^3$—$(CH_2)_m$—$NH_2$ and 2,2-dimethyl-1,3-dioxolane-4-methylamine as $R^1R^2NH$, MS (ISP) 513.5 $(M+H)^+$.

Example 235

Cyclohexylmethyl-2-methyl-5-(2,4,5-trifluoro-phenyl)-1H-pyrrole-3-carboxylic acid cyclohexylamide

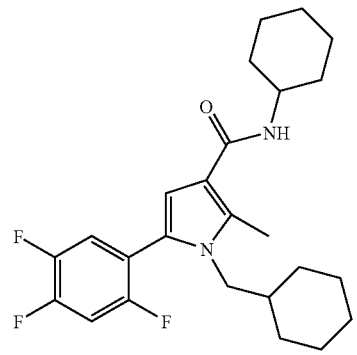

The title compound was synthesized in analogy to Example 68, using 3-oxo-butyric acid methyl ester as compound of formula R, 2-bromo-1-(2,4,5-trifluoro-phenyl)-ethanone as compound of formula S, c-cyclohexyl-methylamine as $R^3$—$(CH_2)_m$—$NH_2$ and cyclohexylamine as $R^1R^2NH$, MS (ISP) 433.5 $(M+H)^+$.

Example 236

Cyclohexylmethyl-2-methyl-5-(2,4,5-trifluoro-phenyl)-1H-pyrrole-3-carboxylic acid ((1RS,2RS)-2-hydroxy-cyclohexyl)-amide

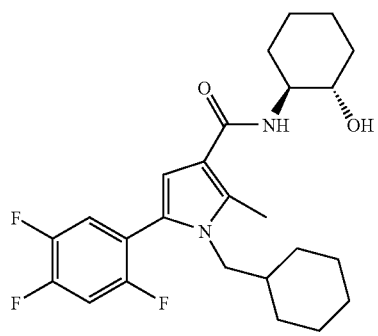

The title compound was synthesized in analogy to Example 68, using 3-oxo-butyric acid methyl ester as compound of formula R, 2-bromo-1-(2,4,5-trifluoro-phenyl)-ethanone as compound of formula S, c-cyclohexyl-methylamine as $R^3$—$(CH_2)_m$—$NH_2$ and trans-2-amino-cyclohexanol as $R^1R^2NH$, MS (ISP) 449.5 $(M+H)^+$.

Example 237

Cyclohexylmethyl-5-(2,4-difluoro-phenyl)-2-methyl-1H-pyrrole-3-carboxylic acid cyclohexylamide

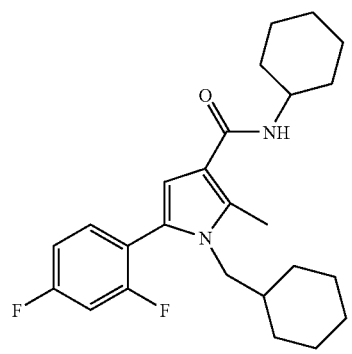

The title compound was synthesized in analogy to Example 68, using 3-oxo-butyric acid methyl ester as compound of formula R, 2-bromo-1-(2,4-difluoro-phenyl)-ethanone as compound of formula S, c-cyclohexyl-methylamine as $R^3$—$(CH_2)_m$—$NH_2$ and cyclohexylamine as $R^1R^2NH$, MS (ISP) 415.5 $(M+H)^+$.

Example 238

Cyclopropylmethyl-2-methyl-5-(4-trifluoromethoxy-phenyl)-1H-pyrrole-3-carboxylic acid piperidin-1-ylamide

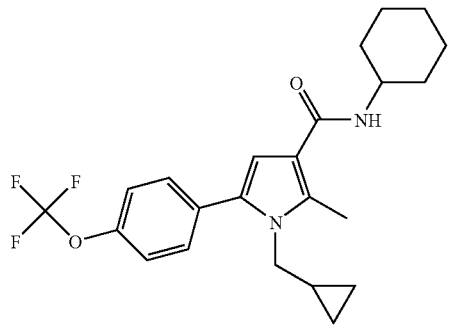

The title compound was synthesized in analogy to Example 68, using 3-oxo-butyric acid methyl ester as compound of formula R, 2-bromo-1-(4-trifluoromethoxy-phenyl)-ethanone as compound of formula S, cyclopropanemethylamine as $R^3$—$(CH_2)_m$—$NH_2$ and cyclohexylamine as $R^1R^2NH$, MS (ISP) 421.4 $(M+H)^+$.

Example 239

Cyclohexylmethyl-5-(2,4-difluoro-phenyl)-2-methyl-1H-pyrrole-3-carboxylic acid ((1RS,2RS)-2-hydroxy-cyclohexyl)-amide

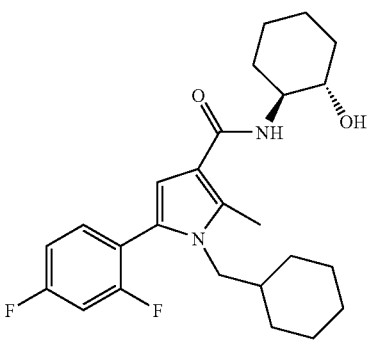

The title compound was synthesized in analogy to Example 68, using 3-oxo-butyric acid methyl ester as compound of formula R, 2-bromo-1-(2,4-difluoro-phenyl)-ethanone as compound of formula S, c-cyclohexyl-methylamine as $R^3$—$(CH_2)_m$—$NH_2$ and trans-2-amino-cyclohexanol as $R^1R^2NH$, MS (ISP) 431.5 $(M+H)^+$.

Example 240

5-(2-Chloro-4,5-difluoro-phenyl)-1-cyclohexylmethyl-2-methyl-1H-pyrrole-3-carboxylic acid cyclohexylmethyl-amide

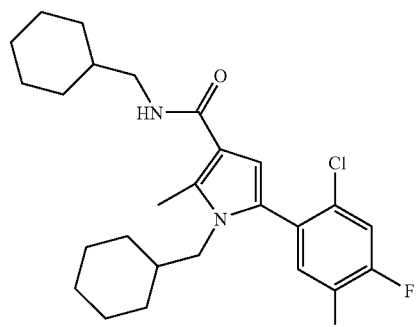

The title compound was synthesized in analogy to Example 68, using c-cyclohexyl-methylamine as $R^1R^2NH$, c-cyclohexyl-methylamine as $R^3—(CH_2)_m—NH_2$ and 2-bromo-1(2-chloro-4,5-difluoro-phenyl)-ethanone, MS (ISP) 463.4 $(M+H)^+$.

Example 241

5-(2-Chloro-4-fluoro-phenyl)-1-cyclohexylmethyl-2-methyl-1H-pyrrole-3-carboxylic acid cyclohexylamide

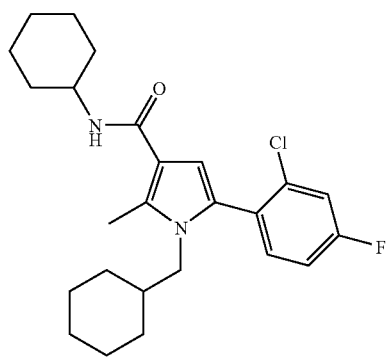

The title compound was synthesized in analogy to Example 68, using cyclohexylamine as $R^1R^2NH$, c-cyclohexyl-methylamine as $R^3—(CH_2)_m—NH_2$ and 2-bromo-1(2-chloro-4-fluoro-phenyl)-ethanone, MS (ISP) 431.5 $(M+H)^+$.

Example 242

5-(2,5-Bis-trifluoromethyl-phenyl)-1-cyclohexylmethyl-2-methyl-1H-pyrrole-3-carboxylic acid piperidin-1-ylamide

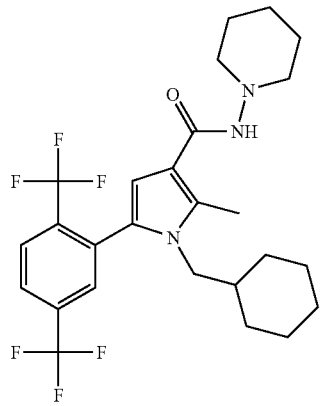

The title compound was synthesized in analogy to Example 68, using 1-piperidinamine as $R^1R^2NH$, c-cyclohexyl-methylamine as $R^3—(CH_2)_m—NH_2$ and 1-(2,5-bis-trifluoromethyl-phenyl)-2-bromo-ethanone, MS (ISP) 516.5 $(M+H)^+$.

Example 243

5-(2-Chloro-5-fluoro-phenyl)-1-cyclohexylmethyl-2-methyl-1H-pyrrole-3-carboxylic acid cyclohexylamide

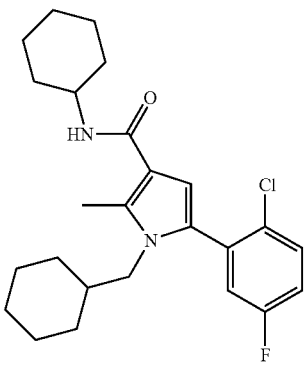

The title compound was synthesized in analogy to Example 68, using cyclohexylamine as $R^1R^2NH$, c-cyclohexyl-methylamine as $R^3—(CH_2)_m—NH_2$ and 2-bromo-1-(2-chloro-5-fluoro-phenyl)-ethanone, MS (ISP) 431.5 $(M+H)^+$.

Example 244

Cyclopropylmethyl-2-methyl-5-(3-trifluoromethyl-phenyl)-1H-pyrrole-3-carboxylic acid cyclohexylamide

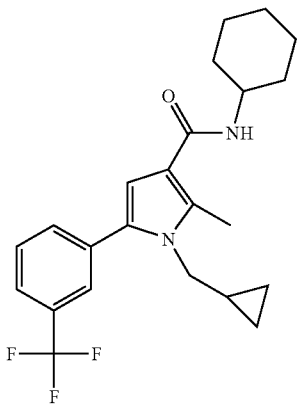

The title compound was synthesized in analogy to Example 68, using 3-oxo-butyric acid methyl ester as compound of formula R, 2-bromo-1-(3-trifluoromethyl-phenyl)-ethanone as compound of formula S, cyclopropanemethylamine as $R^3$—$(CH_2)_m$—$NH_2$ and cyclohexylamine as $R^1R^2NH$, MS (ISP) 405.5 $(M+H)^+$.

Example 245

Cyclopropylmethyl-5-(2-fluoro-3-trifluoromethyl-phenyl)-2-methyl-1H-pyrrole-3-carboxylic acid cyclohexylamide

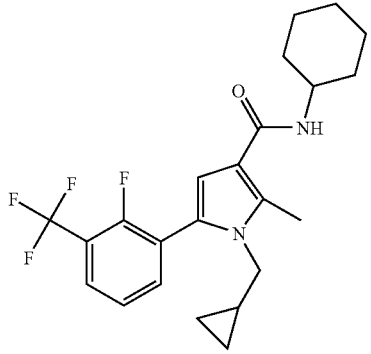

The title compound was synthesized in analogy to Example 68, using 3-oxo-butyric acid methyl ester as compound of formula R, 2-bromo-1-(2-fluoro-3-trifluoromethyl-phenyl)-ethanone as compound of formula S, cyclopropanemethylamine as $R^3$—$(CH_2)_m$—$NH_2$ and cyclohexylamine as $R^1R^2NH$, MS (ISP) 423.4 $(M+H)^+$.

Example 246

Cyclopropylmethyl-5-(2-fluoro-3-trifluoromethyl-phenyl)-2-methyl-1H-pyrrole-3-carboxylic acid piperidin-1-ylamide

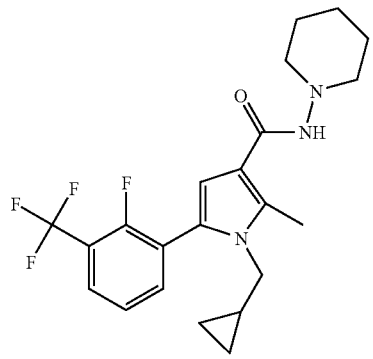

The title compound was synthesized in analogy to Example 68, using 3-oxo-butyric acid methyl ester as compound of formula R, 2-bromo-1-(2-fluoro-3-trifluoromethyl-phenyl)-ethanone as compound of formula S, cyclopropanemethylamine as $R^3$—$(CH_2)_m$—$NH_2$ and 1-piperidinamine as $R^1R^2NH$, MS (ISP) 424.4 $(M+H)^+$.

Example 247

1-(2-Cyclohexyl-ethyl)-5-(5-fluoro-2-methoxy-phenyl)-2-methyl-1H-pyrrole-3-carboxylic acid cyclohexylamide

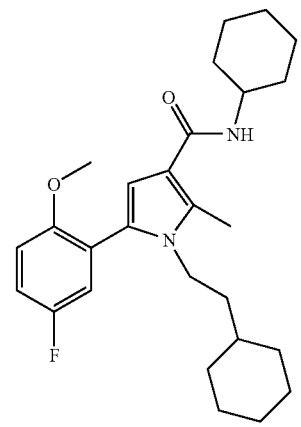

The title compound was synthesized in analogy to Example 68, using 3-oxo-butyric acid methyl ester as compound of formula R, 2-bromo-1-(5-fluoro-2-methoxy-phenyl)-ethanone as compound of formula S, 2-cyclohexyl-ethylamine as $R^3$—$(CH_2)_m$—$NH_2$ and cyclohexylamine as $R^1R^2NH$, MS (ISP) 441.6 $(M+H)^+$.

Example 248

1-(2-Cyclohexyl-ethyl)-5-(5-fluoro-2-methoxy-phenyl)-2-methyl-1H-pyrrole-3-carboxylic acid cyclohexylamide

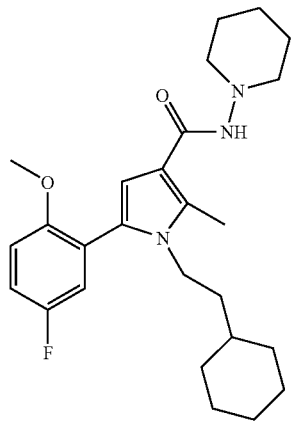

The title compound was synthesized in analogy to Example 68, using 3-oxo-butyric acid methyl ester as compound of formula R, 2-bromo-1-(5-fluoro-2-methoxy-phenyl)-ethanone as compound of formula S, 2-cyclohexyl-ethylamine as $R^3$—$(CH_2)_m$—$NH_2$ and 1-piperidinamine as $R^1R^2NH$, MS (ISP) 442.3 (M+H)$^+$.

Example 249

5-(2,4-Bis-trifluoromethyl-phenyl)-1-cyclohexylmethyl-2-methyl-1H-pyrrole-3-carboxylic acid cyclohexylamide

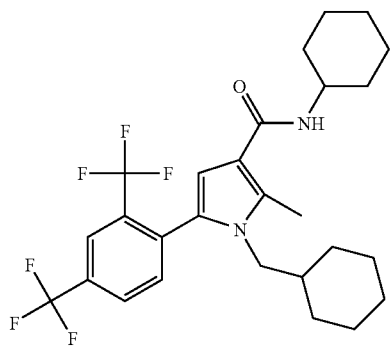

The title compound was synthesized in analogy to Example 68, using 3-oxo-butyric acid methyl ester as compound of formula R, 1-(2,4-bis-trifluoromethyl-phenyl)-2-bromo-ethanone as compound of formula S, c-cyclohexyl-methylamine as $R^3$—$(CH_2)_m$—$NH_2$ and cyclohexylamine as $R^1R^2NH$, MS (ISP) 515.3 (M+H)$^+$.

Example 250

Cyclohexylmethyl-5-(2-fluoro-5-trifluoromethyl-phenyl)-2-methyl-1H-pyrrole-3-carboxylic acid ((1SR,2RS)-2-hydroxy-cyclohexyl)-amide

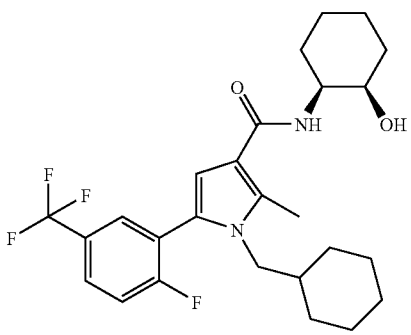

The title compound was synthesized in analogy to Example 68, using 3-oxo-butyric acid methyl ester as compound of formula R, 2-bromo-1-(2-fluoro-5-trifluoromethylphenyl)-ethanone as compound of formula S, c-cyclohexyl-methylamine as $R^3$—$(CH_2)_m$—$NH_2$ and cis-2-aminocyclohexanole as $R^1R^2NH$, MS (ISP) 481.5 (M+H)$^+$.

Example 251

5-(2-Chloro-5-trifluoromethyl-phenyl)-1-cyclohexylmethyl-2-methyl-1H-pyrrole-3-carboxylic acid ((1S,2S)-2-hydroxy-cyclohexyl)-amide

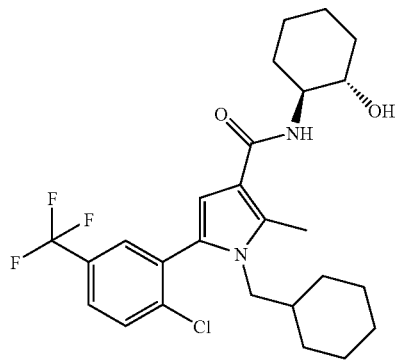

The title compound was isolated by prep. HPLC on Chiral-Pak AD from example 233, MS (ISP) 497.4 (M+H)⁺.

Example 252

5-(2-Chloro-5-trifluoromethyl-phenyl)-1-cyclohexyl-methyl-2-methyl-1H-pyrrole-3-carboxylic acid ((1R,2R)-2-hydroxy-cyclohexyl)-amide

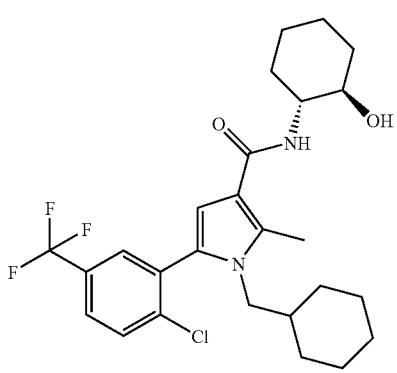

The title compound was isolated by prep. HPLC on Chiral-Pak AD from example 233, MS (ISP) 497.4 (M+H)⁺.

Example 253

Cyclohexylmethyl-5-(2-fluoro-5-trifluoromethyl-phenyl)-2-methyl-1H-pyrrole-3-carboxylic acid ((1S,2S)-2-hydroxy-cyclohexyl)-amide

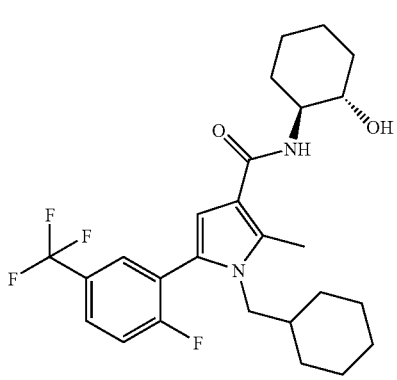

The title compound was isolated by prep. HPLC on Chiral-Pak AD from example 228, MS (ISP) 481.5 (M+H)⁺.

Example 254

Cyclohexylmethyl-5-(2-fluoro-5-trifluoromethyl-phenyl)-2-methyl-1H-pyrrole-3-carboxylic acid ((1R,2R)-2-hydroxy-cyclohexyl)-amide

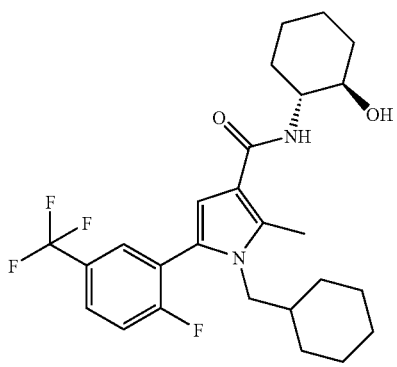

The title compound was isolated by prep. HPLC on Chiral-Pak AD from example 228, MS (ISP) 481.5 (M+H)⁺.

Example 255

Cyclohexylmethyl-5-(2,5-dichloro-phenyl)-2-methyl-1H-pyrrole-3-carboxylic acid ((1S,2S)-2-hydroxy-cyclohexyl)-amide

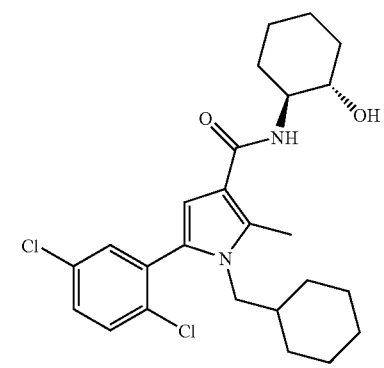

The title compound was isolated by prep. HPLC on Chiral-Pak AD from example 212 MS (ISP) 463.4 (M+H)⁺.

Example 256

Cyclohexylmethyl-5-(2,5-dichloro-phenyl)-2-methyl-1H-pyrrole-3-carboxylic acid ((1R,2R)-2-hydroxy-cyclohexyl)-amide

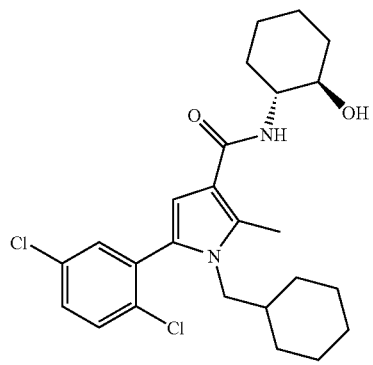

The title compound was isolated by prep. HPLC on ChiralPak AD from example 212, MS (ISP) 463.4 (M+H)+.

Example 257

Cyclohexylmethyl-5-(2,4-dichloro-phenyl)-2-methyl-1H-pyrrole-3-carboxylic acid ((1S,2R)-2-hydroxy-cyclohexyl)-amide

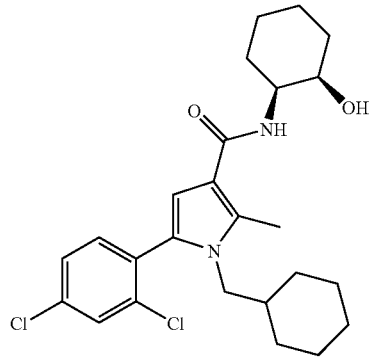

The title compound was isolated by prep. HPLC on ChiralPak AD from example 208, MS (ISP) 463.4 (M+H)+.

Example 258

Cyclohexylmethyl-5-(2,4-dichloro-phenyl)-2-methyl-1H-pyrrole-3-carboxylic acid ((1R,2S)-2-hydroxy-cyclohexyl)-amide

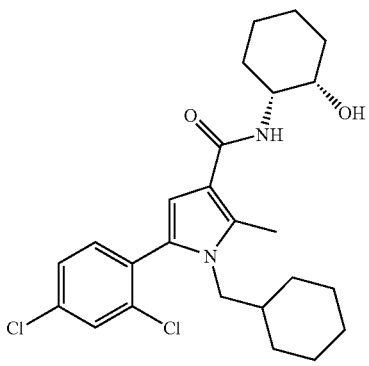

The title compound was isolated by prep. HPLC on ChiralPak AD from example 208, MS (ISP) 463.4 (M+H)+.

Example 259

1-(2-Hydroxy-cyclohexylmethyl)-2-methyl-5-(2-trifluoromethoxy-phenyl)-1H-pyrrole-3-carboxylic acid cyclohexylamide

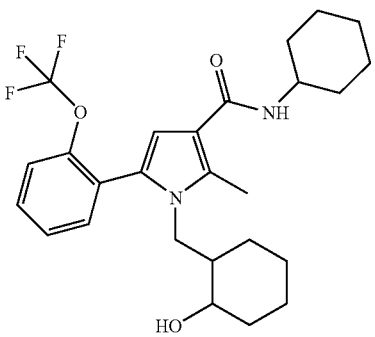

The title compound was synthesized in analogy to Example 68, using 3-oxo-butyric acid methyl ester as compound of formula R, 2-bromo-1-(2-trifluoromethoxy-phenyl)-ethanone as compound of formula S, 2-aminomethyl-1-cyclohexanol as $R^3$—$(CH_2)_m$—$NH_2$ and cyclohexylamine as $R^1R^2NH$, MS (ISP) 479.6 (M+H)+.

Example 260

Cyclohexylmethyl-5-(2,5-dichloro-phenyl)-2-methyl-1H-pyrrole-3-carboxylic acid ((1SR,2RS)-2-hydroxy-cyclohexyl)-amide

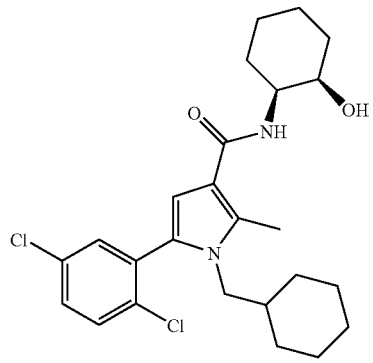

The title compound was synthesized in analogy to Example 68, using 3-oxo-butyric acid methyl ester as compound of formula R, 2-bromo-1-(2,5-dichloro-phenyl)-ethanone as compound of formula S, c-cyclohexyl-1-methylamine as $R^3$—$(CH_2)_m$—$NH_2$ and cis-2-amino-cyclohexanol as $R^1R^2NH$, MS (ISP) 463.4 (M+H)$^+$.

Example 261

Cyclohexylmethyl-5-(2,5-dichloro-phenyl)-2-methyl-1H-pyrrole-3-carboxylic acid piperidin-1-ylamide

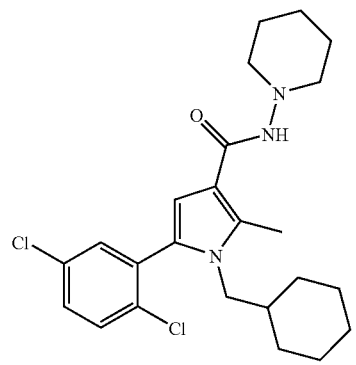

The title compound was synthesized in analogy to Example 68, using 3-oxo-butyric acid methyl ester as compound of formula R, 2-bromo-1-(2,5-dichloro-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 448.4 (M+H)$^+$.

Example 262

Cyclohexylmethyl-5-(2,4-dichloro-phenyl)-2-methyl-1H-pyrrole-3-carboxylic acid piperidin-1-ylamide

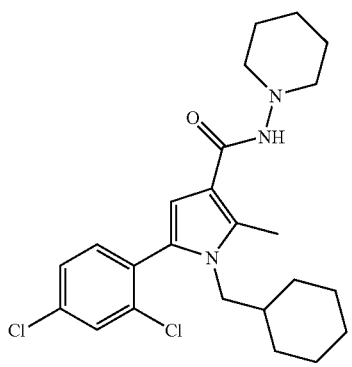

The title compound was synthesized in analogy to Example 68, using 3-oxo-butyric acid methyl ester as compound of formula R, 2-bromo-1-(2,4-dichloro-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 448.4 (M+H)$^+$.

Example 263

5-(2-Chloro-5-trifluoromethyl-phenyl)-1-cyclohexylmethyl-2-methyl-1H-pyrrole-3-carboxylic acid ((1SR,2RS)-2-hydroxy-cyclohexyl)-amide

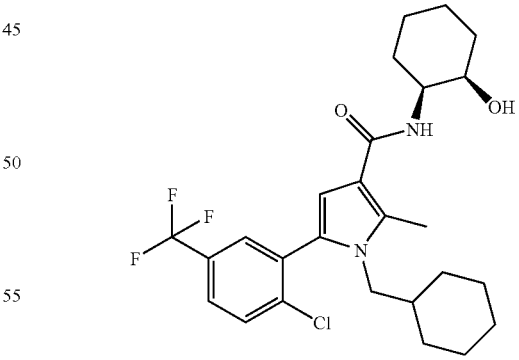

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, c-cyclohexyl-1-methylamine as $R^3$—$(CH_2)_m$—$NH_2$ and cis-2-amino-cyclohexanol as $R^1R^2NH$, MS (ISP) 497.4 (M+H)$^+$.

Example 264

5-(2-Chloro-5-trifluoromethyl-phenyl)-1-cyclohexyl-methyl-2-methyl-1H-pyrrole-3-carboxylic acid piperidin-1-ylamide

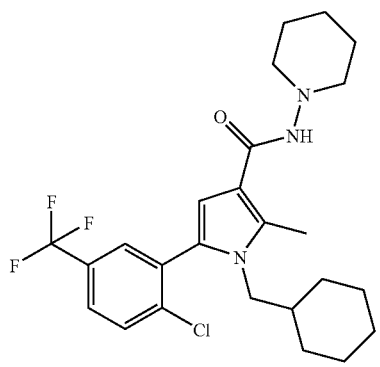

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 482.6 $(M+H)^+$.

Example 265

1-(2-Cyclopropyl-ethyl)-5-(5-fluoro-2-methoxy-phenyl)-2-methyl-1H-pyrrole-3-carboxylic acid cyclohexylamide

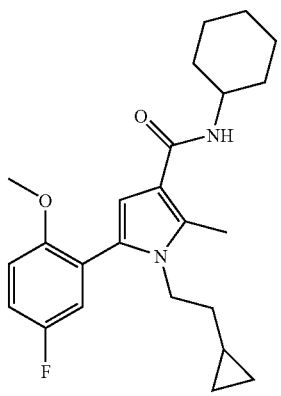

The title compound was synthesized in analogy to Example 68, using 3-oxo-butyric acid methyl ester as compound of formula R, 2-bromo-1-(5-fluoro-2-methoxy-phenyl)-ethanone as compound of formula S, 2-cyclopropyl-ethylamine as $R^3$—$(CH_2)_m$—$NH_2$ and cyclohexylamine as $R^1R^2NH$, MS (ISP) 399.5 $(M+H)^+$.

Example 266

5-(5-Chloro-2-methoxy-4-methyl-phenyl)-1-(2-cyclopropyl-ethyl)-2-methyl-1H-pyrrole-3-carboxylic acid cyclohexylamide

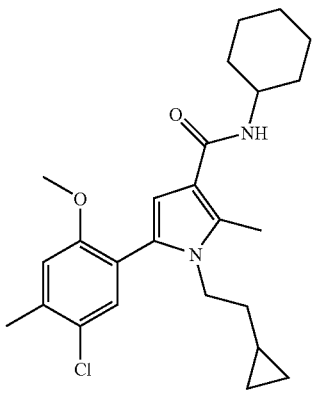

The title compound was synthesized in analogy to Example 68, using 3-oxo-butyric acid methyl ester as compound of formula R, 2-bromo-1-(5-chloro-2-methoxy-4-methyl-phenyl)-ethanone as compound of formula S, 2-cyclopropyl-ethylamine as $R^3$—$(CH_2)_m$—$NH_2$ and cyclohexylamine as $R^1R^2NH$, MS (ISP) 429.6 $(M+H)^+$.

Example 267

Cyclohexylmethyl-2-(3-fluoro-5-trifluoromethyl-phenyl)-5-methyl-1H-imidazole-4-carboxylic acid piperidin-1-ylamide

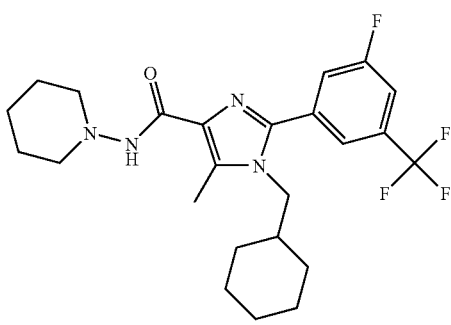

The title compound was synthesized in analogy to Example 49, using 3-Fluoro-5-trifluoromethyl-benzylamine as $R^4$—$CH_2$—$NH_2$, 1-amino-piperidine as $R^1R^2NH$ and (bromomethyl)cyclohexane as $R^3$—$(CH_2)_m$—Br, MS (ISP) 467 $(M+H)^+$.

Example 268

Cyclohexylmethyl-5-methyl-2-(2-propoxy-phenyl)-1H-imidazole-4-carboxylic acid piperidin-1-ylamide

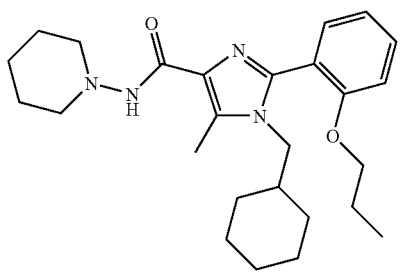

The title compound was synthesized in analogy to Example 49, using 2-propoxy-benzylamine as $R^4$—$CH_2$—$NH_2$, 1-amino-piperidine as $R^1R^2NH$ and (bromomethyl)cyclohexane as $R^3$—$(CH_2)_m$—Br, MS (ISP) 439 (M+H)$^+$.

Example 269

2-(5-Chloro-2-fluoro-phenyl)-1-(2-cyclopropyl-ethyl)-5-methyl-1H-imidazole-4-carboxylic acid [2-(tetrahydro-pyran-4-yl)-ethyl]-amide

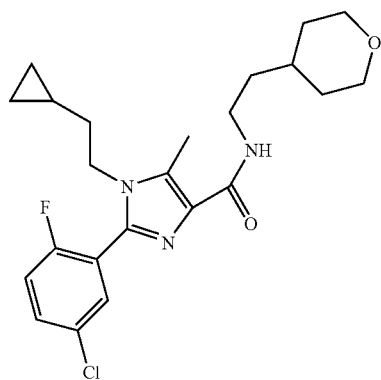

The title compound was synthesized in analogy to Example 49, using 5-chloro-2-fluoro-benzylamine as $R^4$—$CH_2$—$NH_2$, 2-(Tetrahydro-pyran-4-yl)-ethylamine as $R^1R^2NH$ and (bromoethyl)cyclopropane as $R^3$—$(CH_2)_m$—Br, MS (ISP) 434 (M+H)$^+$.

Example 270

1-(2-Cyclopropyl-ethyl)-2-(3-fluoro-5-trifluoromethyl-phenyl)-5-methyl-1H-imidazole-4-carboxylic acid piperidin-1-ylamide

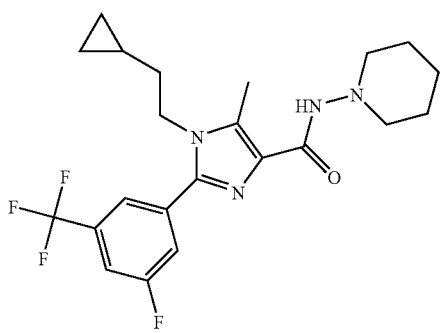

The title compound was synthesized in analogy to Example 49, using 3-fluoro-5-trifluoromethyl-benzylamine as $R^4$—$CH_2$—$NH_2$, 1-aminopiperidine as $R^1R^2NH$ and (bromoethyl)cyclopropane as $R^3$—$(CH_2)_m$—Br, MS (ISP) 439 (M+H)$^+$.

Example 271

2-(5-Chloro-2-fluoro-phenyl)-1-cyclohexylmethyl-5-methyl-1H-imidazole-4-carboxylic acid piperidin-1-ylamide

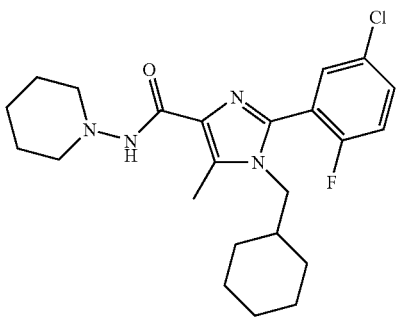

The title compound was synthesized in analogy to Example 49, using 5-chloro-2-fluoro-benzylamine as $R^4$—$CH_2$—$NH_2$, 1-aminopiperidine as $R^1R^2NH$ and (bromomethyl)cyclohexane as $R^3$—$(CH_2)_m$—Br, MS (ISP) 433 (M+H)$^+$.

Example 272

2-(2-Chloro-5-trifluoromethyl-phenyl)-1-cyclohexyl-methyl-5-methyl-1H-imidazole-4-carboxylic acid [2-(tetrahydro-pyran-4-yl)-ethyl]-amide

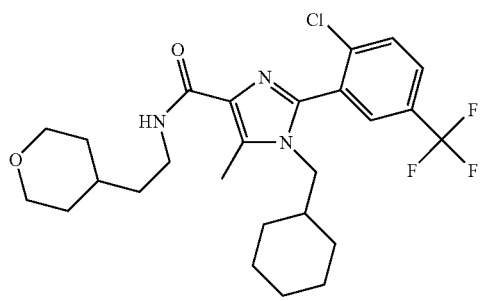

The title compound was synthesized in analogy to Example 49, using 2-chloro-5-trifluoromethyl-benzylamine as $R^4$—$CH_2$—$NH_2$, [2-(tetrahydro-pyran-4-yl)-ethyl]-amine as $R^1R^2NH$ and (bromomethyl)cyclohexane as $R^3$—$(CH_2)_m$—Br, MS (ISP) 512 (M+H)$^+$.

Example 273

Cyclohexylmethyl-2-(2,3-dichloro-phenyl)-5-methyl-1H-imidazole-4-carboxylic acid piperidin-1-ylamide

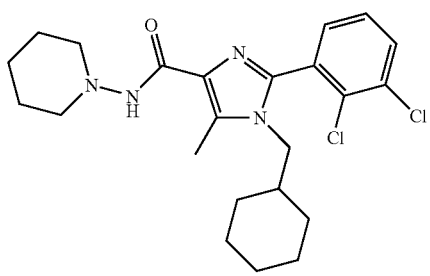

The title compound was synthesized in analogy to Example 49, using 2,3-dichloro-benzylamine as $R^4$—$CH_2$—$NH_2$, 1-aminopiperidine as $R^1R^2NH$ and (bromomethyl)cyclohexane as $R^3$—$(CH_2)_m$—Br, MS (ISP) 449 (M+H)$^+$.

Example 274

5-(2,5-Bis-trifluoromethyl-phenyl)-1-cyclohexylmethyl-2-methyl-1H-pyrrole-3-carboxylic acid (tetrahydro-pyran-4-yl)-amide

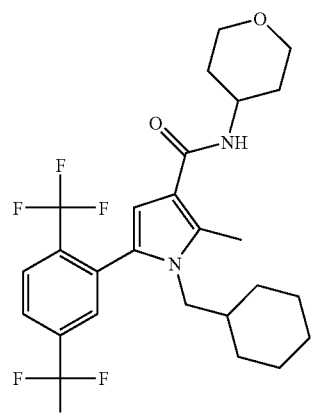

The title compound was synthesized in analogy to Example 68, using 3-oxo-butyric acid methyl ester as compound of formula R, 1-(2,5-bis-trifluoromethyl-phenyl)-2-bromo-ethanone as compound of formula S, c-cyclohexylmethylamine as $R^3$—$(CH_2)_m$—$NH_2$ and tetrahydro-pyran-4-ylamine as $R^1R^2NH$, MS (ISP) 517.2 (M+H)$^+$.

Example 275

5-(2,5-Bis-trifluoromethyl-phenyl)-1-cyclopropylmethyl-2-methyl-1H-pyrrole-3-carboxylic acid cyclohexylamide

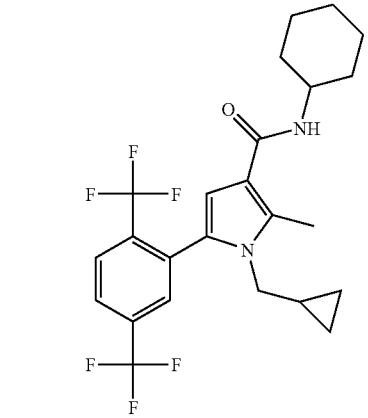

The title compound was synthesized in analogy to Example 68, using 3-oxo-butyric acid methyl ester as compound of formula R, 1-(2,5-bis-trifluoromethyl-phenyl)-2-bromo-ethanone as compound of formula S, cyclopropanemethylamine as R³—(CH₂)ₘ—NH₂ and cyclohexylamine as R¹R²NH, MS (ISP) 473.1 (M+H)⁺.

Example 276

Cyclopropylmethyl-2-methyl-5-(2-trifluoromethoxy-phenyl)-1H-pyrrole-3-carboxylic acid cyclohexylamide

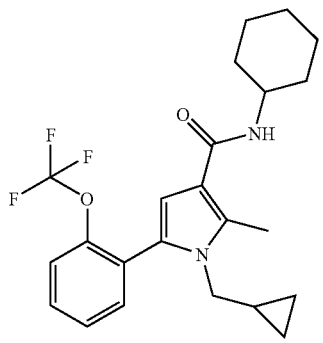

The title compound was synthesized in analogy to Example 68, using 3-oxo-butyric acid methyl ester as compound of formula R, 2-bromo-1-(2-trifluoromethoxy-phenyl)-ethanone as compound of formula S, c-cyclopropyl-1-methylamine as R³—(CH₂)ₘ—NH₂ and cyclohexylamine as R¹R²NH, MS (ISP) 421.2 (M+H)⁺.

Example 277

Cyclopropylmethyl-2-methyl-5-(2-trifluoromethoxy-phenyl)-1H-pyrrole-3-carboxylic acid ((1RS,2RS)-2-hydroxy-cyclohexyl)-amide

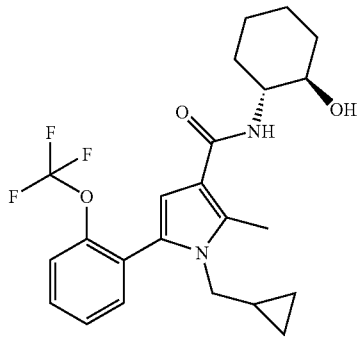

The title compound was synthesized in analogy to Example 68, using 3-oxo-butyric acid methyl ester as compound of formula R, 2-bromo-1-(2-trifluoromethoxy-phenyl)-ethanone as compound of formula S, c-cyclopropyl-1-methylamine as R³—(CH₂)ₘ—NH₂ and trans-2-amino-cyclohexanol as R¹R²NH, MS (ISP) 437.3 (M+H)⁺.

Example 278

Bromo-1-(5-chloro-2-trifluoromethoxy-phenyl)-ethanone

The title compound was synthesized from 5-chloro-2-trifluoromethoxy-benzoic acid (prepared from 1-chloro-4-trifluoromethoxy-benzene by the orth-lithiation method according to Schlosser et al. Eur. J. Org. Chem. 2001, 21, 3991-3997) according to the general scheme 12.

5-(5-Chloro-2-trifluoromethoxy-phenyl)-1-cyclohexylmethyl-2-methyl-1H-pyrrole-3-carboxylic acid cyclohexylamide

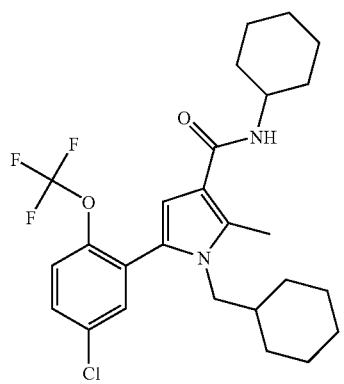

The title compound was synthesized in analogy to Example 68, using 3-oxo-butyric acid methyl ester as compound of formula R, 2-bromo-1-(5-chloro-2-trifluoromethoxyphenyl)-ethanone as compound of formula S, c-cyclohexyl-methylamine as R³—(CH₂)ₘ—NH₂ and cyclohexylamine as R¹R²NH, MS (ISP) 497.1 (M+H)⁺.

Example 279

5-(2-Fluoro-5-trifluoromethyl-phenyl)-1-(4-hydroxy-cyclohexylmethyl)-2-methyl-1H-pyrrole-3-carboxylic acid cyclohexylamide

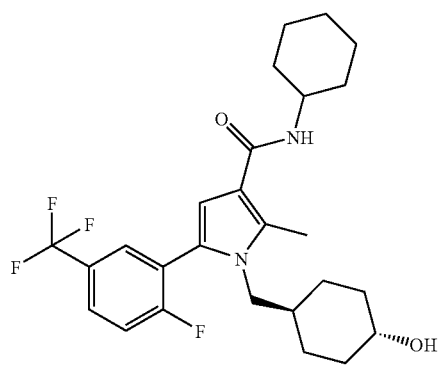

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, trans-4-(aminomethyl)-cyclohexanol, as R³—(CH₂)ₘ—NH₂ and cyclohexylamine as R¹R²NH, MS (ISP) 481.6 (M+H)⁺.

Example 280

Bromo-1-(5-bromo-2-trifluoromethoxy-phenyl)-ethanone

The title compound was synthesized from 5-bromo-2-trifluoromethoxy-benzoic acid (prepared from 1-bromo-4-trifluoromethoxy-benzene by the orth-lithiation method according to Schlosser et al. *Eur. J. Org. Chem.* 2001, 21, 3991-3997) according to the general scheme 12.

5-(5-Bromo-2-trifluoromethoxy-phenyl)-1-cyclohexylmethyl-2-methyl-1H-pyrrole-3-carboxylic acid cyclohexylamide

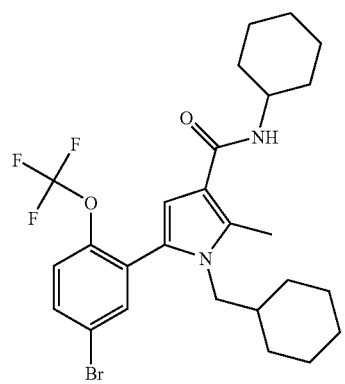

The title compound was synthesized in analogy to Example 68, using 3-oxo-butyric acid methyl ester as compound of formula R, 2-bromo-1-(5-bromo-2-trifluoromethoxy-phenyl)-ethanone as compound of formula S, c-cyclohexyl-methylamine as $R^3$—$(CH_2)_m$—$NH_2$ and cyclohexylamine as $R^1R^2NH$, MS (ISP) 542.8 (M+H)$^+$.

Example 281

Cyclopropylmethyl-5-(2-fluoro-5-trifluoromethyl-phenyl)-2-methyl-1H-pyrrole-3-carboxylic acid ((1R,2R)-2-hydroxy-cyclohexyl)-amide

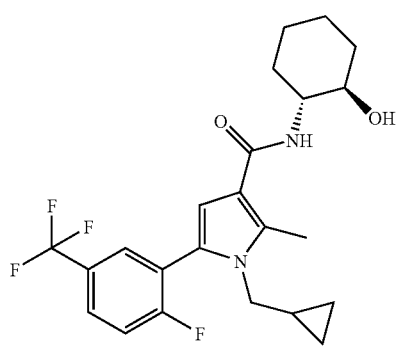

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, c-cyclopropyl-1-methylamine as $R^3$—$(CH_2)_m$—$NH_2$ and (1R,2R)-2-amino-cyclohexanol as $R^1R^2NH$, MS (ISP) 439.5 (M+H)$^+$.

Example 282

5-(2-Fluoro-5-trifluoromethyl-phenyl)-1-((1SR,2RS)-2-hydroxy-cyclohexylmethyl)-2-methyl-1H-pyrrole-3-carboxylic acid cyclohexylamide

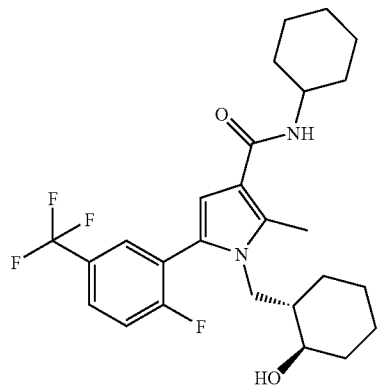

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, cis-2-aminomethyl-1-cyclohexanol as $R^3$—$(CH_2)_m$—$NH_2$ and cyclohexylamine as $R^1R^2NH$, MS (ISP) 480.2 (M+H)$^+$.

Example 283

5-(2-Fluoro-5-trifluoromethyl-phenyl)-1-((1RS,2RS)-2-hydroxy-cyclohexylmethyl)-2-methyl-1H-pyrrole-3-carboxylic acid cyclohexylamide

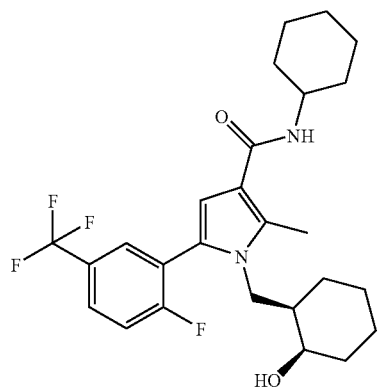

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, trans-2-aminomethyl-1-cyclohexanol as $R^3$—$(CH_2)_m$—$NH_2$ and cyclohexylamine as $R^1R^2NH$, MS (ISP) 480.2 (M+H)$^+$.

Example 284

5-(5-Chloro-2-fluoro-phenyl)-1-cyclopropylmethyl-2-methyl-1H-pyrrole-3-carboxylic acid cyclohexylamide

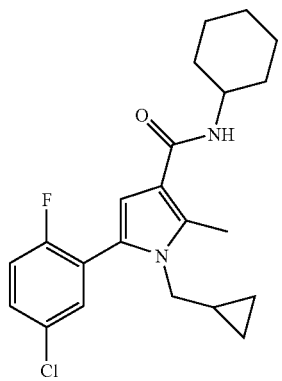

The title compound was synthesized in analogy to Example 68, using 3-oxo-butyric acid methyl ester as compound of formula R, 2-bromo-1-(5-chloro-2-fluoro-phenyl)-ethanone as compound of formula S, cyclopropanemethylamine as $R^3$—$(CH_2)_m$—$NH_2$ and cyclohexylamine as $R^1R^2NH$, MS (ISP) 389.3 $(M+H)^+$.

Example 285

5-(2-Fluoro-5-trifluoromethyl-phenyl)-1-(1RS,2SR)-2-hydroxy-cyclohexylmethyl)-2-methyl-1H-pyrrole-3-carboxylic acid ((1R,2R)-2-hydroxy-cyclohexyl)-amide

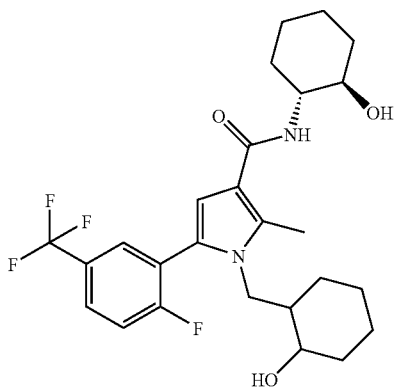

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, trans-2-aminomethyl-1-cyclohexanol as $R^3$—$(CH_2)_m$—$NH_2$ and (1R,2R)-2-amino-cyclohexanol as $R^1R^2NH$, MS (ISP) 497.4 $(M+H)^+$.

Example 286

5-(2-Fluoro-5-trifluoromethyl-phenyl)-1-(1RS,2RS)-2-hydroxy-cyclohexylmethyl)-2-methyl-1H-pyrrole-3-carboxylic acid ((1R,2R)-2-hydroxy-cyclohexyl)-amide

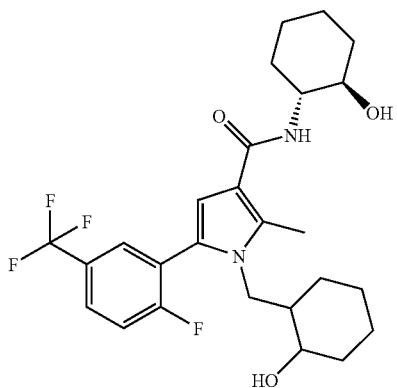

The title compound was synthesized in analogy to Example 68, using 3-oxo-butyric acid methyl ester as compound of formula R, 2-bromo-1-(2-fluoro-5-trifluoromethyl-phenyl)-ethanone as compound of formula S, cis-2-aminomethyl-1-cyclohexanol as $R^3$—$(CH_2)_m$—$NH_2$ and (1R,2R)-2-amino-cyclohexanol as $R^1R^2NH$, MS (ISP) 497.4 $(M+H)^+$.

Example 287

5-(2-Chloro-5-trifluoromethyl-phenyl)-1-cyclopropylmethyl-2-methyl-1H-pyrrole-3-carboxylic acid cyclohexylamide

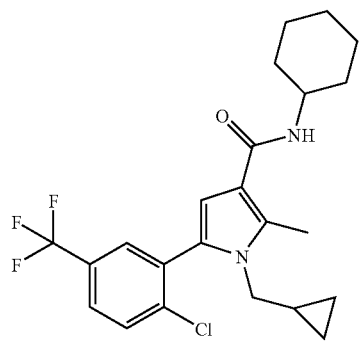

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, c-cyclopropyl-1-methylamine as $R^3$—$(CH_2)_m$—$NH_2$ and cyclohexylamine as $R^1R^2NH$, MS (ISP) 439.4 $(M+H)^+$.

Example 288

5-(2,5-Bis-trifluoromethyl-phenyl)-1-(2,2-dimethyl-cyclopropylmethyl)-2-methyl-1H-pyrrole-3-carboxylic acid cyclohexylamide

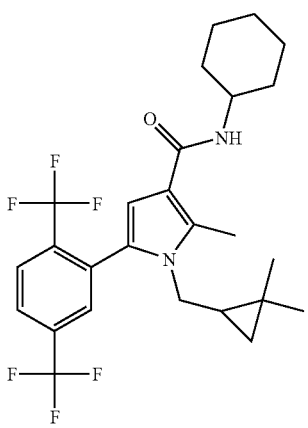

The title compound was synthesized in analogy to Example 68, using 3-oxo-butyric acid methyl ester as compound of formula R, 1-(2,5-bis-trifluoromethyl-phenyl)-2-bromo-ethanone as compound of formula S, C-(2,2-dimethyl-cyclopropyl)-methylamine (prepared from 2,2-dimethyl-cyclopropanecarboxylic acid amide by reduction with LiAlH$_4$ according to the procedure described by Saski et al. J. Org. Chem. 1971, 36, 1968-1971) as R$^3$—(CH$_2$)$_m$—NH$_2$ and cyclohexylamine as R$^1$R$^2$NH, MS (ISP) 501.3 (M+H)$^+$.

Example 289

5-(2,5-Bis-trifluoromethyl-phenyl)-1-(2-cyclopropyl-ethyl)-2-methyl-1H-pyrrole-3-carboxylic acid cyclohexylamide

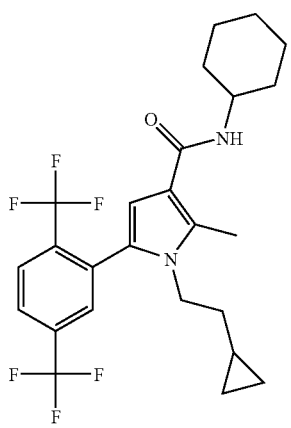

The title compound was synthesized in analogy to Example 68, using 3-oxo-butyric acid methyl ester as compound of formula R, 1-(2,5-bis-trifluoromethyl-phenyl)-2-bromo-ethanone as compound of formula S, 2-cyclopropyl-ethylamine as R$^3$—(CH$_2$)$_m$—NH$_2$ and cyclohexylamine as R$^1$R$^2$NH, MS (ISP) 487.4 (M+H)$^+$.

Example 290

5-(2,5-Bis-trifluoromethyl-phenyl)-1-(2-cyclopropyl-ethyl)-2-methyl-1H-pyrrole-3-carboxylic acid ((1R,2R)-2-hydroxy-cyclohexyl)-amide

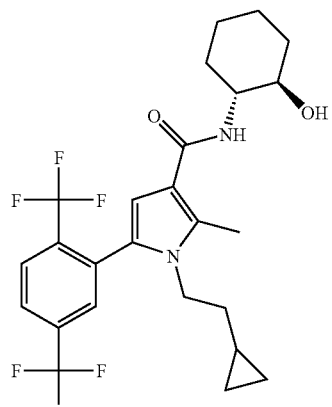

The title compound was synthesized in analogy to Example 68, using 3-oxo-butyric acid methyl ester as compound of formula R, 1-(2,5-bis-trifluoromethyl-phenyl)-2-bromo-ethanone as compound of formula S, 2-cyclopropyl-ethylamine as R$^3$—(CH$_2$)$_m$—NH$_2$ and (1R,2R)-2-amino-cyclohexanol as R$^1$R$^2$NH, MS (ISP) 503.1 (M+H)$^+$.

Example 291

5-(5-Chloro-2-fluoro-phenyl)-1-((S)-2,2-dimethyl-cyclopropylmethyl)-2-methyl-1H-pyrrole-3-carboxylic acid cyclohexylamide

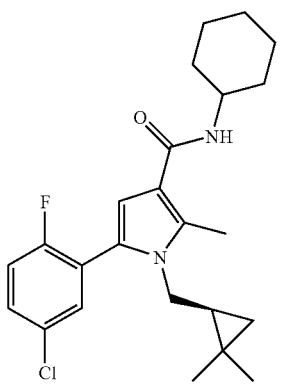

The title compound was synthesized in analogy to Example 68, using 3-oxo-butyric acid methyl ester as compound of formula R, 2-bromo-1-(5-chloro-2-fluoro-phenyl)-ethanone as compound of formula S, C—(S)-(2,2-dimethyl-cyclopropyl)-methylamine (prepared from (S)-2,2-dimethyl-cyclopropanecarboxylic acid amide by reduction with LiAlH$_4$ according to the procedure described by Saski et al. J.

Org. Chem. 1971, 36, 1968-1971) as $R^3$—$(CH_2)_m$—$NH_2$ and cyclohexylamine as $R^1R^2NH$, MS (ISP) 417.3 $(M+H)^+$.

Example 292

5-(5-Chloro-2-fluoro-phenyl)-1-((S)-2,2-dimethyl-cyclopropylmethyl)-2-methyl-1H-pyrrole-3-carboxylic acid ((1R,2R)-2-hydroxy-cyclohexyl)-amide

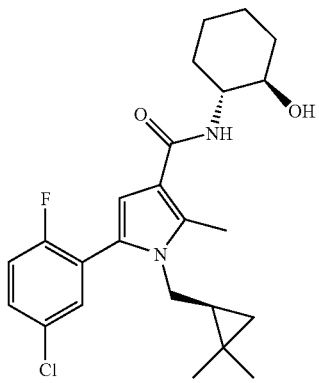

The title compound was synthesized in analogy to Example 68, using 3-oxo-butyric acid methyl ester as compound of formula R, 2-bromo-1-(5-chloro-2-fluoro-phenyl)-ethanone as compound of formula S, C—(S)-(2,2-dimethyl-cyclopropyl)-methylamine (prepared from (S)-2,2-dimethyl-cyclopropanecarboxylic acid amide by reduction with LiAlH$_4$ according to the procedure described by Saski et al. J. Org. Chem. 1971, 36, 1968-1971) as $R^3$—$(CH_2)_m$—$NH_2$ and (1R,2R)-2-amino-cyclohexanol as $R^1R^2NH$, MS (ISP) 433.4 $(M+H)^+$.

Example 293

5-(2-Chloro-5-trifluoromethyl-phenyl)-1-((1SR, 2RS)-2-hydroxy-cyclohexylmethyl)-2-methyl-1H-pyrrole-3-carboxylic acid cyclohexylamide

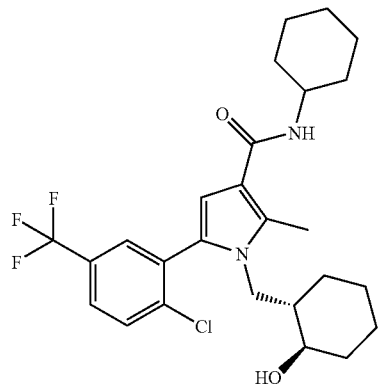

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, trans-2-aminomethyl-1-cyclohexanol as $R^3$—$(CH_2)_m$—$NH_2$ and cyclohexylamine as $R^1R^2NH$, MS (ISP) 497.4 $(M+H)^+$.

Example 294

5-(2-Chloro-5-trifluoromethyl-phenyl)-1-((1RS, 2RS)-2-hydroxy-cyclohexylmethyl)-2-methyl-1H-pyrrole-3-carboxylic acid cyclohexylamide

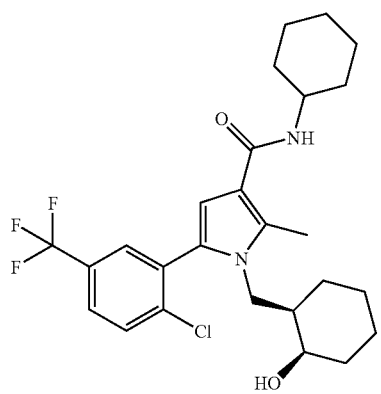

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, cis-2-aminomethyl-1-cyclohexanol as $R^3$—$(CH_2)_m$—$NH_2$ and cyclohexylamine as $R^1R^2NH$, MS (ISP) 497.4 $(M+H)^+$.

Example 295

5-(5-Chloro-2-methyl-phenyl)-1-cyclohexylmethyl-2-methyl-1H-pyrrole-3-carboxylic acid ((1R,2R)-2-hydroxy-cyclohexyl)-amide

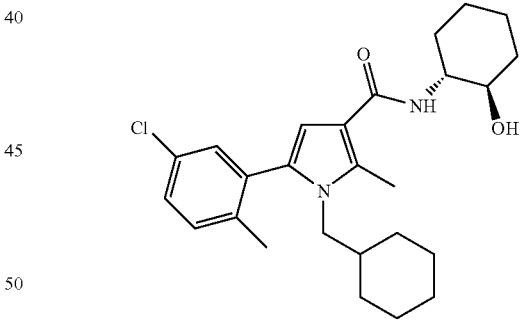

The title compound was synthesized in analogy to Example 68, using 3-oxo-butyric acid methyl ester as compound of formula R, 2-bromo-1-(5-chloro-2-methyl-phenyl)-ethanone as compound of formula S, c-cyclohexyl-1-methylamine as $R^3$—$(CH_2)_m$—$NH_2$ and (1R,2R)-2-amino-cyclohexanol as $R^1R^2NH$, MS (ISP) 443.4 $(M+H)^+$.

Preparation of 2-bromo-1-(5-chloro-2-methyl-phenyl)-ethanone

The title compound was synthesized from 1-(5-chloro-2-methylphenyl)-ethanone following the procedure described by D. M. Rotstein et al., J. Med. Chem. 35(15), 2818-2825 (1992).

Example 296

Cyclohexylmethyl-5-(5-fluoro-2-methyl-phenyl)-2-methyl-1H-pyrrole-3-carboxylic acid piperidin-1-ylamide

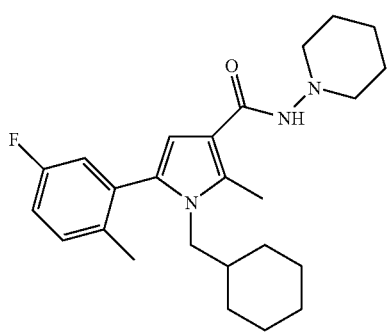

The title compound was synthesized in analogy to Example 68, using 3-oxo-butyric acid methyl ester as compound of formula R, 2-bromo-1-(5-fluoro-2-methyl-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 412.5 (M+H)$^+$.

Preparation of 2-bromo-1-(5-fluoro-2-methyl-phenyl)-ethanone

The title compound was synthesized from 1-(5-fluoro-2-methylphenyl)-ethanone following the procedure described by D. M. Rotstein et al., J. Med. Chem. 35(15), 2818-2825 (1992).

Example 297

5-(5-Chloro-2-methyl-phenyl)-1-cyclohexylmethyl-2-methyl-1H-pyrrole-3-carboxylic acid piperidin-1-ylamide

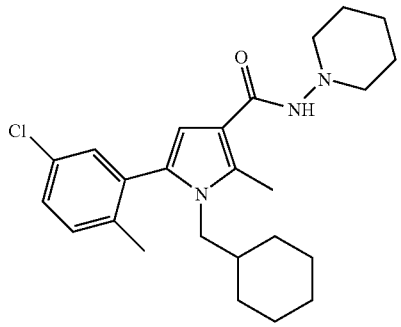

The title compound was synthesized in analogy to Example 68, using 3-oxo-butyric acid methyl ester as compound of formula R, 2-bromo-1-(5-chloro-2-methyl-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 428.6 (M+H)$^+$.

Example 298

5-(4-Chloro-2-methyl-phenyl)-1-cyclohexylmethyl-2-methyl-1H-pyrrole-3-carboxylic acid ((1R,2R)-2-hydroxy-cyclohexyl)-amide

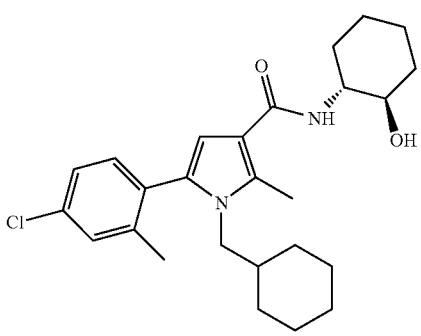

The title compound was synthesized in analogy to Example 68, using 3-oxo-butyric acid methyl ester as compound of formula R, 2-bromo-1-(4-chloro-2-methyl-phenyl)-ethanone as compound of formula S, c-cyclohexyl-1-methylamine as $R^3$—$(CH_2)_m$—$NH_2$ and (1R,2R)-2-aminocyclohexanol as $R^1R^2NH$, MS (ISP) 443.4 (M+H)$^+$.

Example 299

5-(4-Chloro-2-methyl-phenyl)-1-cyclohexylmethyl-2-methyl-1H-pyrrole-3-carboxylic acid piperidin-1-ylamide

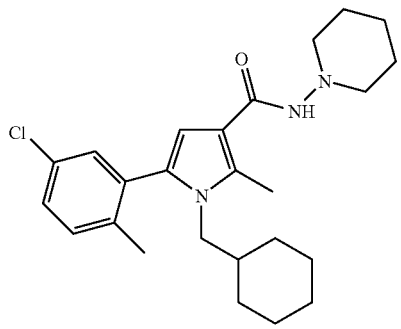

The title compound was synthesized in analogy to Example 68, using 3-oxo-butyric acid methyl ester as compound of formula R, 2-bromo-1-(4-chloro-2-methyl-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 428.6 (M+H)$^+$.

Example 300

Cyclohexylmethyl-5-(5-fluoro-2-methyl-phenyl)-2-methyl-1H-pyrrole-3-carboxylic acid ((1R,2R)-2-hydroxy-cyclohexyl)-amide

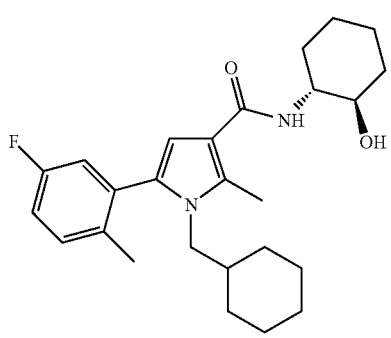

The title compound was synthesized in analogy to Example 68, using 3-oxo-butyric acid methyl ester as compound of formula R, 2-bromo-1-(5-fluoro-2-methyl-phenyl)-ethanone as compound of formula S, c-cyclohexyl-1-methylamine as $R^3$—$(CH_2)_m$—$NH_2$ and (1R,2R)-2-aminocyclohexanol as $R^1R^2NH$, MS (ISP) 427.5 (M+H)$^+$.

Example 301

Cyclohexylmethyl-2-methyl-5-(2-methyl-5-trifluoromethyl-phenyl)-1H-pyrrole-3-carboxylic acid ((1R,2R)-2-hydroxy-cyclohexyl)-amide

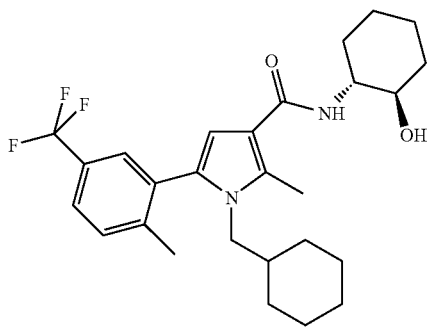

The title compound was synthesized in analogy to Example 68, using 3-oxo-butyric acid methyl ester as compound of formula R, 2-bromo-1-(2-methyl-5-trifluoromethyl-phenyl)-ethanone as compound of formula S, c-cyclohexyl-1-methylamine as $R^3$—$(CH_2)_m$—$NH_2$ and (1R,2R)-2-amino-cyclohexanol as $R^1R^2NH$, MS (ISP) 477.4 (M+H)$^+$.

Preparation of 2-bromo-1-(2-methyl-5-trifluoromethyl-phenyl)-ethanone

The title compound was synthesized from 1-(2-methyl-5-trifluoromethyl-phenyl)-ethanone following the procedure described by D. M. Rotstein et al., J. Med. Chem. 35(15), 2818-2825 (1992).

Preparation of 1-(2-methyl-5-trifluoromethyl-phenyl)-ethanone

The title compound was synthesized from 2-methyl-5-(trifluoromethyl)-benzoyl chloride via the reaction of the corresponding Weinreb amide with methyl magnesium bromide in THF.

Example 302

Cyclohexylmethyl-2-methyl-5-(2-methyl-5-trifluoromethyl-phenyl)-1H-pyrrole-3-carboxylic acid piperidin-1-ylamide

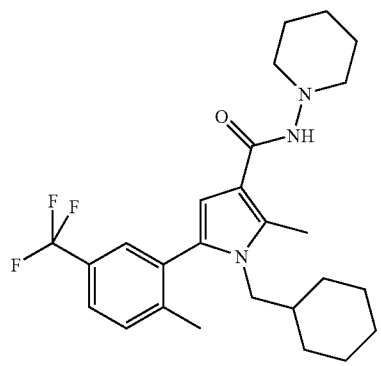

The title compound was synthesized in analogy to Example 68, using 3-oxo-butyric acid methyl ester as compound of formula R, 2-bromo-1-(2-methyl-5-trifluoromethyl-phenyl)-ethanone as compound of formula S, c-cyclohexyl-1-methylamine as $R^3$—$(CH_2)_m$—$NH_2$ and 1-piperidinamine as $R^1R^2NH$, MS (ISP) 462.4 (M+H)$^+$.

Example 303

5-(2-Chloro-5-trifluoromethyl-phenyl)-1-(2-cyclopropyl-ethyl)-2-methyl-1H-pyrrole-3-carboxylic acid ((1R,2R)-2-hydroxy-cyclohexyl)-amide

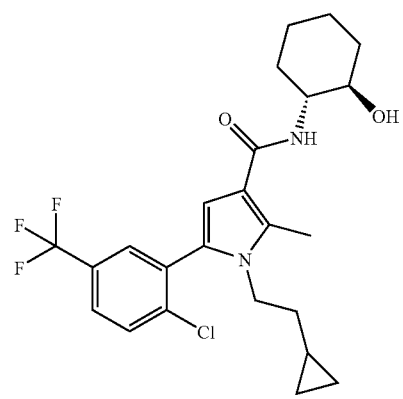

The title compound was synthesized in analogy to Example 68, using 3-oxo-butyric acid methyl ester as compound of formula R, 1-(2-chloro-5-trifluoromethyl-phenyl)-2-bromo-ethanone as compound of formula S, 2-cyclopropyl-ethylamine as $R^3$—$(CH_2)_m$—$NH_2$ and ((1R,2R)-2-hydroxy-cyclohexyl)-amine as $R^1R^2NH$, MS (ISP) 469.4 (M+H)—.

Example 304

5-(2-Chloro-5-trifluoromethyl-phenyl)-1-(2-cyclopropyl-ethyl)-2-methyl-1H-pyrrole-3-carboxylic acid piperidin-1-ylamide

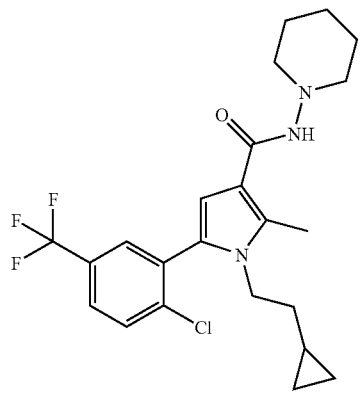

The title compound was synthesized in analogy to Example 68, using 3-oxo-butyric acid methyl ester as compound of formula R, 1-(2-chloro-5-trifluoromethyl-phenyl)-2-bromo-ethanone as compound of formula S, 2-cyclopropyl-ethylamine as $R^3$—$(CH_2)_m$—$NH_2$ and 1-piperidinamine as $R^1R^2NH$, MS (ISP) 454.5 (M+H)$^+$.

Example 306

5-(2-Chloro-5-trifluoromethyl-phenyl)-1-((1R,2R)-2-hydroxy-cyclohexylmethyl)-2-methyl-1H-pyrrole-3-carboxylic acid piperidin-1-ylamide

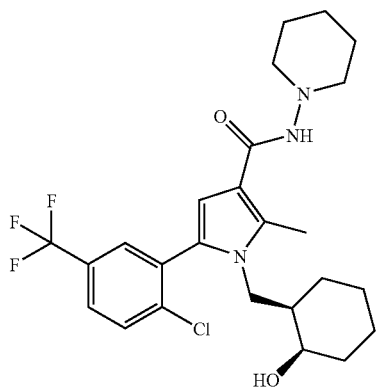

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, cis-2-aminomethyl-1-cyclohexanol as $R^3$—$(CH_2)_m$—$NH_2$ 1-piperidinamine as $R^1R^2NH$, MS (ISP) 498.3 (M+H)$^+$.

Example 307

5-(2-Chloro-5-trifluoromethyl-phenyl)-1-(2-hydroxy-cyclohexylmethyl)-2-methyl-1H-pyrrole-3-carboxylic acid ((1R,2R)-2-hydroxy-cyclohexyl)-amide

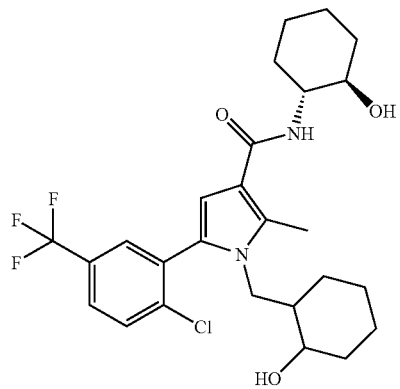

The title compound was synthesized in analogy to Example 68, using 3-oxo-butyric acid methyl ester as compound of formula R, 2-bromo-1-(2-chloro-5-trifluoromethyl-phenyl)-ethanone as compound of formula S, cis-2-aminomethyl-1-cyclohexanol as $R^3$—$(CH_2)_m$—$NH_2$ and (1R,2R)-2-amino-cyclohexanol as $R^1R^2NH$, MS (ISP) 513.5 (M+H)+

GALENICAL EXAMPLES

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.c0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

What is claimed is:

1. A compound of formula (I):

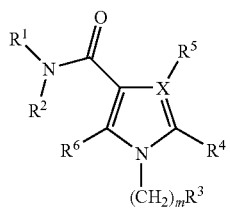

or a pharmaceutically acceptable salt thereof wherein:
(a) X is C or N;
(b) $R^1$ is hydrogen or lower alkyl;
(c) $R^2$ is $(CH_2)_n$—$R^{2a}$, wherein $R^{2a}$ is cycloalkyl which is optionally mono-substituted, di-substituted, tri-substituted or tetra-substituted, independently, by a substituent selected from the group consisting of hydroxy, lower alkyl, lower alkoxy, fluorinated lower alkyl and fluorinated lower alkoxy;
(d) $R^3$ is cycloalkyl which is optionally mono-substituted, di-substituted, tri-substituted or tetra-substituted, independently, by a substituent selected from the group consisting of hydroxy, lower alkyl, lower alkoxy, fluorinated lower alkyl and fluorinated lower alkoxy;
(e) $R^4$ is selected from the group consisting of:
  (1) naphthyl, which is optionally mono-substituted, di-substituted or tri-substituted, independently, by a substituent selected from the group consisting of hydroxy, lower alkyl, lower alkoxy, halogen, lower alkylamino, halogenated lower alkyl, halogenated lower alkoxy and nitro; and
  (2) phenyl, which is optionally mono-substituted, di-substituted or tri-substituted, independently, by a substituent selected from the group consisting of hydroxy, lower alkyl, lower alkoxy, halogen, nitro, halogenated lower alkyl, halogenated lower alkoxy, cyano, lower alkylsulfonyl and —$NR^7R^8$; or two adjacent substituents of said phenyl residue together are —O—$(CH_2)_p$—O— or —$(CH_2)_2$—C(O)NH—;
(f) $R^5$ and $R^6$ are each independently selected from the group consisting of hydrogen, lower alkyl, halogen and fluorinated methyl;
(g) $R^7$ and $R^8$ are each independently either hydrogen or lower alkyl;
(h) m is 0, 1 or 2;
(i) n is 0 or 1; and
(j) p is 1, 2 or 3.

2. A compound according to claim 1, wherein $R^1$ is hydrogen.

3. A compound according to claim 1, wherein $R^{2a}$ is cycloalkyl having three to six carbon atoms which is optionally mono-substituted, di-substituted, tri-substituted or tetra-substituted, independently, by lower alkyl or hydroxy.

4. A compound according to claim 1, wherein $R^{2a}$ is cyclohexyl which is optionally mono-substituted, di-substituted, tri-substituted or tetra-substituted, by hydroxy.

5. A compound according to claim 1, wherein $R^3$ is an unsubstituted cycloalkyl residue with five or six carbon atoms.

6. A compound according to claim 1, wherein $R^3$ is a substituted cycloalkyl residue with five or six carbon atoms.

7. A compound according to claim 1, wherein $R^4$ is naphthyl.

8. A compound according to claim 1, wherein $R^4$ is phenyl optionally mono-substituted, di-substituted or tri-substituted, independently, by a substituent selected from the group consisting of hydroxy, lower alkyl, lower alkoxy, halogen, nitro, halogenated lower alkyl, halogenated lower alkoxy, cyano, lower alkylsulfonyl, and a residue —$NR^7R^8$.

9. A compound according to claim 1, wherein two adjacent substituents of phenyl residue $R^4$ together are —O—$(CH_2)_p$—O— or —$(CH_2)_2$—C(O)NH—, and p is 2 or 3.

10. A compound according to claim 1, wherein both $R^7$ and $R^8$ are methyl or both $R^7$ and $R^8$ are ethyl.

11. A compound according to claim 1, wherein $R^7$ and $R^8$ are both hydrogen.

12. A compound according to claim 1, wherein X is C.

13. A compound according to claim 1, wherein X is N.

14. A compound according to claim 1, selected from the group consisting of:
1-Cyclohexylmethyl-5-(2,5-dimethoxy-phenyl)-2-methyl-1H-pyrrole-3-carboxylic acid cyclohexylamide,
1-Cyclohexylmethyl-5-(2,5-dimethoxy-phenyl)-2-methyl-1H-pyrrole-3-carboxylic acid cyclopentylamide,
1-Cyclohexylmethyl-5-(2,5-dimethoxy-phenyl)-2-methyl-1H-pyrrole-3-carboxylic acid cyclobutylamide,
1-Cyclohexylmethyl-5-(2,5-dimethoxy-phenyl)-2-methyl-1H-pyrrole-3-carboxylic acid cyclopropylamide,
and any pharmaceutically acceptable salt thereof.

15. A compound according to claim 1, selected from the group consisting of:
- 5-(3,5-Bis-trifluoromethyl-phenyl)-1-cyclohexylmethyl-2-methyl-1H-pyrrole-3-carboxylic acid cyclohexylamide,
- 2-(5-Chloro-2-methoxy-phenyl)-1-(2-cyclohexyl-ethyl)-5-methyl-1H-imidazole-4-carboxylic acid cyclohexylamide,
- Cyclohexylmethyl-2-(2-methoxy-phenyl)-5-methyl-1H-imidazole-4-carboxylic acid cyclohexylamide,
- 1-(2-Cyclohexyl-ethyl)-2-(2-methoxy-phenyl)-5-methyl-1H-imidazole-4-carboxylic acid cyclohexylamide,
- 5-(4-Chloro-2-fluoro-5-methyl-phenyl)-1-cyclohexylmethyl-2-methyl-1H-pyrrole-3-carboxylic acid cyclohexylamide,
- Cyclohexylmethyl-5-(2-ethyl-phenyl)-2-methyl-1H-pyrrole-3-carboxylic acid cyclohexylamide,
- 5-(5-Chloro-2-methoxy-phenyl)-1-cyclohexylmethyl-2-methyl-1H-pyrrole-3-carboxylic acid cyclohexylamide,
- Cyclohexylmethyl-5-(5-fluoro-2-methoxy-phenyl)-2-methyl-1H-pyrrole-3-carboxylic acid cyclohexylamide,
- 5-(3-Bromo-4-dimethylamino-phenyl)-1-cyclohexylmethyl-2-methyl-1H-pyrrole-3-carboxylic acid cyclohexylamide,
- Cyclohexylmethyl-5-(4-hydroxy-2-methyl-phenyl)-2-methyl-1H-pyrrole-3-carboxylic acid cyclohexylamide,
- Cyclohexylmethyl-5-(2-fluoro-4-methoxy-phenyl)-2-methyl-1H-pyrrole-3-carboxylic acid cyclohexylamide,
- 5-(3-Bromo-phenyl)-1-cyclohexylmethyl-2-methyl-1H-pyrrole-3-carboxylic acid cyclohexylamide,
- 1-(2-Cyclohexyl-ethyl)-5-methyl-2-(4-trifluoromethoxy-phenyl)-1H-imidazole-4-carboxylic acid cyclopropylamide,
- Cyclohexylmethyl-5-methyl-2-(4-trifluoromethoxy-phenyl)-1H-imidazole-4-carboxylic acid cyclohexylamide,
- 2-(5-Chloro-2-methoxy-phenyl)-1-cyclohexylmethyl-5-methyl-1H-imidazole-4-carboxylic acid cyclohexylamide,
- Cyclohexylmethyl-5-methyl-2-(4-trifluoromethoxy-phenyl)-1H-imidazole-4-carboxylic acid cyclopropylamide,
- Cyclohexylmethyl-5-methyl-2-(4-trifluoromethoxy-phenyl)-1H-imidazole-4-carboxylic acid cyclopentylamide,
- 2-(5-Chloro-2-methoxy-phenyl)-1-cyclohexylmethyl-5-methyl-1H-imidazole-4-carboxylic acid cyclopentylamide,
- 2-(5-Chloro-2-methoxy-phenyl)-1-(2-cyclohexyl-ethyl)-5-methyl-1H-imidazole-4-carboxylic acid cyclopentylamide,
- 2-(5-Chloro-2-methoxy-phenyl)-1-cyclohexylmethyl-5-methyl-1H-imidazole-4-carboxylic acid cyclopropylamide,
- 2-(5-Chloro-2-methoxy-phenyl)-1-(2-cyclohexyl-ethyl)-5-methyl-1H-imidazole-4-carboxylic acid cyclopropylamide,
- Cyclopropylmethyl-2-(2-methoxy-phenyl)-5-methyl-1H-imidazole-4-carboxylic acid cyclohexylamide,
- Cyclohexylmethyl-5-(3,5-dichloro-phenyl)-2-methyl-1H-pyrrole-3-carboxylic acid cyclohexylamide,
- Cyclohexylmethyl-5-(3,5-difluoro-phenyl)-2-methyl-1H-pyrrole-3-carboxylic acid cyclohexylamide,
- 5-(5-Bromo-2-methoxy-phenyl)-1-cyclohexylmethyl-2-methyl-1H-pyrrole-3-carboxylic acid cyclohexylamide, and any pharmaceutically acceptable salt thereof.

16. A compound according to claim 1, selected from the group consisting of:
- 1-Cyclohexylmethyl-5-(2,5-dimethoxy-phenyl)-2-methyl-1H-pyrrole-3-carboxylic acid cyclopropylmethylamide,
- 5-(2-Chloro-5-trifluoromethyl-phenyl)-1-cyclohexylmethyl-2-methyl-1H-pyrrole-3-carboxylic acid ((1RS,2RS)-2-hydroxy-cyclohexyl)-amide,
- Cyclohexylmethyl-2-(5-fluoro-2-methyl-phenyl)-5-methyl-1H-imidazole-4-carboxylic acid cyclohexylamide,
- 5-(3-Bromo-2-hydroxy-5-methoxy-phenyl)-1-cyclohexylmethyl-2-methyl-1H-pyrrole-3-carboxylic acid cyclohexylamide,
- Cyclohexylmethyl-5-methyl-2-p-tolyl-1H-imidazole-4-carboxylic acid cyclohexylamide,
- Cyclohexylmethyl-2-(5-fluoro-2-methyl-phenyl)-5-methyl-1H-imidazole-4-carboxylic acid cyclobutylamide,
- 2-(5-Chloro-2-methyl-phenyl)-1-(2-cyclohexyl-ethyl)-5-methyl-1H-imidazole-4-carboxylic acid cyclopentylamide,
- 2-(4-Chloro-2-methyl-phenyl)-1-cyclohexylmethyl-5-methyl-1H-imidazole-4-carboxylic acid cyclohexylamide,
- 2-(5-Chloro-2-methyl-phenyl)-1-(2-cyclohexyl-ethyl)-5-methyl-1H-imidazole-4-carboxylic acid cyclohexylamide,
- 2-(4-Chloro-2-methyl-phenyl)-1-(2-cyclohexyl-ethyl)-5-methyl-1H-imidazole-4-carboxylic acid cyclohexylamide,
- 5-(2,5-Dimethoxy-phenyl)-2-methyl-1-phenethyl-1H-pyrrole-3-carboxylic acid cyclohexylamide,
- Cyclohexylmethyl-5-(4-methoxy-2-methyl-phenyl)-2-methyl-1H-pyrrole-3-carboxylic acid cyclohexylamide,
- Cyclohexylmethyl-5-(4-ethoxy-2-methyl-phenyl)-2-methyl-1H-pyrrole-3-carboxylic acid cyclohexylamide,
- Cyclohexylmethyl-2-methyl-5-[2-methyl-4-(2,2,2-trifluoro-ethoxy)-phenyl]-1H-pyrrole-3-carboxylic acid cyclohexylamide,
- 5-(3,5-Bis-trifluoromethyl-phenyl)-1-cyclohexylmethyl-2,4-dimethyl-1H-pyrrole-3-carboxylic acid cyclohexylamide,
- Cyclopropylmethyl-5-(5-fluoro-2-methoxy-phenyl)-2-methyl-1H-pyrrole-3-carboxylic acid cyclohexylamide,
- Cyclopropylmethyl-5-(5-fluoro-2-methoxy-phenyl)-2-methyl-1H-pyrrole-3-carboxylic acid (trans-2-hydroxy-cyclohexyl)-amide,
- 5-(5-Chloro-2-fluoro-phenyl)-1-cyclohexylmethyl-2-methyl-1H-pyrrole-3-carboxylic acid cyclohexylamide,
- 5-(2,5-Bis-trifluoromethyl-phenyl)-1-cyclohexylmethyl-2-methyl-1H-pyrrole-3-carboxylic acid cyclohexylamide,
- 5-(4-Chloro-2-fluoro-phenyl)-1-cyclohexylmethyl-2-methyl-1H-pyrrole-3-carboxylic acid cyclohexylamide,
- Cyclohexylmethyl-5-(2,4-dichloro-phenyl)-2-methyl-1H-pyrrole-3-carboxylic acid cyclohexylamide,
- Cyclohexylmethyl-5-(2,4-dichloro-phenyl)-2-methyl-1H-pyrrole-3-carboxylic acid ((1SR,2RS)-2-hydroxy-cyclohexyl)-amide,
- Cyclohexylmethyl-5-(2,4-dichloro-phenyl)-2-methyl-1H-pyrrole-3-carboxylic acid ((1S,2S)-2-hydroxy-cyclohexyl)-amide,
- Cyclohexylmethyl-5-(2,4-dichloro-phenyl)-2-methyl-1H-pyrrole-3-carboxylic acid ((1R,2R)-2-hydroxy-cyclohexyl)-amide,
- Cyclohexylmethyl-5-(2,5-dichloro-phenyl)-2-methyl-1H-pyrrole-3-carboxylic acid cyclohexylamide, Cyclohexylmethyl-5-(2,5-dichloro-phenyl)-2-methyl-1H-pyrrole-3-carboxylic acid ((1RS,2RS)-2-hydroxy-cyclohexyl)-amide, and any pharmaceutically acceptable salt thereof.

17. A compound according to claim 1, selected from the group consisting of:

5-(2-Chloro-5-trifluoromethyl-phenyl)-1-cyclohexylmethyl-2-methyl-1H-pyrrole-3-carboxylic acid ((1R,2R)-2-hydroxy-cyclohexyl)-amide,
5-(2-Fluoro-5-trifluoromethyl-phenyl)-1-((1SR,2RS)-2-hydroxy-cyclohexylmethyl)-2-methyl-1H-pyrrole-3-carboxylic acid cyclohexylamide,
5-(2-Fluoro-5-trifluoromethyl-phenyl)-1-((1RS,2RS)-2-hydroxy-cyclohexylmethyl)-2-methyl-1H-pyrrole-3-carboxylic acid cyclohexylamide,
5-(2-Fluoro-5-trifluoromethyl-phenyl)-1-(1RS,2RS)-2-hydroxy-cyclohexylmethyl)-2-methyl-1H-pyrrole-3-carboxylic acid ((1R,2R)-2-hydroxy-cyclohexyl)-amide,
5-(2,5-Bis-trifluoromethyl-phenyl)-1-(2-cyclopropyl-ethyl)-2-methyl-1H-pyrrole-3-carboxylic acid ((1R,2R)-2-hydroxy-cyclohexyl)-amide,
5-(2-Chloro-5-trifluoromethyl-phenyl)-1-((1RS,2RS)-2-hydroxy-cyclohexylmethyl)-2-methyl-1H-pyrrole-3-carboxylic acid cyclohexylamide,
1-Cyclohexylmethyl-2-methyl-5-(2-methyl-5-trifluoromethyl-phenyl)-1H-pyrrole-3-carboxylic acid ((1R,2R)-2-hydroxy-cyclohexyl)-amide,
Cyclohexylmethyl-5(2,5-difluoro-phenyl)-2-methyl-1H-pyrrole-3-carboxylic acid cyclohexylamide,
Cyclohexylmethyl-5-(2,5-difluoro-phenyl)-2-methyl-1H-pyrrole-3-carboxylic acid ((1RS,2RS)-2-hydroxy-cyclohexyl)-amide,
Cyclohexylmethyl-5-(2,5-difluoro-phenyl)-2-methyl-1H-pyrrole-3-carboxylic acid ((1RS,2SR)-2-hydroxy-cyclohexylmethyl)-amide,
Cyclohexylmethyl-5-(2,5-difluoro-phenyl)-2-methyl-1H-pyrrole-3-carboxylic acid ((1RS,2RS)-2-hydroxy-cyclohexylmethyl)-amide,
Cyclohexylmethyl-5-(2,4-dichloro-5-fluoro-phenyl)-2-methyl-1H-pyrrole-3-carboxylic acid cyclohexylamide,
Cyclohexylmethyl-5-(2,4-dichloro-5-fluoro-phenyl)-2-methyl-1H-pyrrole-3-carboxylic acid ((1RS,2RS)-2-hydroxy-cyclohexyl)-amide,
Cyclohexylmethyl-5-(2,4-dichloro-5-fluoro-phenyl)-2-methyl-1H-pyrrole-3-carboxylic acid (1-hydroxy-cyclohexylmethyl)-amide,
Cyclohexylmethyl-5-(2,4-dichloro-5-fluoro-phenyl)-2-methyl-1H-pyrrole-3-carboxylic acid cyclopropylmethyl-amide,
Cyclohexylmethyl-2-methyl-5-(2-trifluoromethoxy-phenyl)-1H-pyrrole-3-carboxylic acid cyclohexylamide,
Cyclohexylmethyl-2-methyl-5-(2-trifluoromethoxy-phenyl)-1H-pyrrole-3-carboxylic acid ((1RS,2RS)-2-hydroxy-cyclohexyl)-amide,
Cyclohexylmethyl-2-methyl-5-(2-trifluoromethoxy-phenyl)-1H-pyrrole-3-carboxylic acid cyclohexylmethyl-amide,
Cyclohexylmethyl-2-methyl-5-(2-trifluoromethoxy-phenyl)-1H-pyrrole-3-carboxylic acid cycloheptylmethyl-amide,
Cyclohexylmethyl-5-(2-fluoro-5-trifluoromethyl-phenyl)-2-methyl-1H-pyrrole-3-carboxylic acid cyclohexylamide,
Cyclohexylmethyl-5-(2-fluoro-5-trifluoromethyl-phenyl)-2-methyl-1H-pyrrole-3-carboxylic acid ((1RS,2RS)-2-hydroxy-cyclohexyl)-amide,
5-(5-Chloro-2-methoxy-4-methyl-phenyl)-1-cyclopropylmethyl-2-methyl-1H-pyrrole-3-carboxylic acid cyclohexylamide,
5-(2-Chloro-5-trifluoromethyl-phenyl)-1-cyclohexylmethyl-2-methyl-1H-pyrrole-3-carboxylic acid cyclohexylamide and any pharmaceutically acceptable salt thereof.

18. 5-(2,5-Bis-trifluoromethyl-phenyl)-1-(2-cyclopropyl-ethyl)-2-methyl-1H-pyrrole-3-carboxylic acid ((1R,2R)-2-hydroxy-cyclohexyl)-amide.

19. Cyclopropylmethyl-5-(2-fluoro-5-trifluoromethyl-phenyl)-2-methyl-1H-pyrrole-3-carboxylic acid ((1R,2R)-2-hydroxy-cyclohexyl)-amide.

20. 5-(3,5-Bis-trifluoromethyl-phenyl)-1-cyclopropylmethyl-2-methyl-1H-pyrrole-3-carboxylic acid cyclohexylamide.

21. A compound manufactured by a process for the manufacture of the compounds Of formula (I) as defined in claim 1 where X is C, which process comprises:

reacting an enamine of formula A:

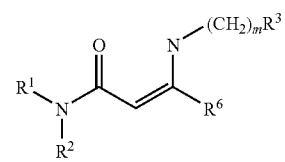

wherein $R^1$, $R^2$, $R^3$, $R^6$ and m are as defined in claim 1;
with an alfa-bromoketone of formula B:

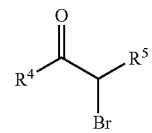

wherein $R^4$ and $R^5$ are as defined in claim 1.

22. A compound manufactured by a process for the manufacture of the compounds of formula (I) as defined in claim 1 where X is N, which process comprises:

alkylating an imidazole of formula F:

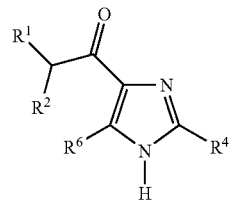

wherein $R^1$, $R^2$, $R^4$ and $R^6$ are as defined in claim 1;
with an alkyl bromide of formula G:

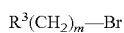

wherein $R^3$ and m are as defined in claim 1.

23. A compound manufactured by a process for the manufacture of compounds of formula (I) as defined in claim 1 where X is C, which process comprises:
reacting a carboxylic acid of formula N:

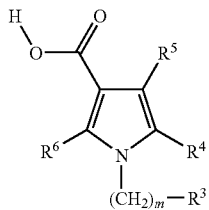

wherein $R^3$, $R^4$, $R^5$, $R^6$ and m are as defined in claim 1; with an amine of formula J:

wherein $R^1$ and $R^2$ are as defined in claim 1.

24. A pharmaceutical composition comprising a compound of claim 1 and a pharmaceutically acceptable carrier and/or adjuvant.

25. A compound according to claim 1, selected from the group consisting of:
Cyclohexylmethyl-2-methyl-5-(2,4,5-trifluoro-phenyl)-1H-pyrrole-3-carboxylic acid cyclohexylamide,
Cyclohexylmethyl-2-methyl-5-(2,4,5-trifluoro-phenyl)-1H-pyrrole-3-carboxylic acid ((1RS,2RS)-2-hydroxy-cyclohexyl)-amide,
Cyclohexylmethyl-5-(2,4-difluoro-phenyl)-2-methyl-1H-pyrrole-3-carboxylic acid cyclohexylamide,
Cyclopropylmethyl-2-methyl-5-(4-trifluoromethoxy-phenyl)-1H-pyrrole-3-carboxylic acid piperidin-1-ylamide,
Cyclohexylmethyl-5-(2,4-difluoro-phenyl)-2-methyl-1H-pyrrole-3-carboxylic acid ((1RS,2RS)-2-hydroxy-cyclohexyl)-amide,
5-(2-Chloro-4,5-difluoro-phenyl)-1-cyclohexylmethyl-2-methyl-1H-pyrrole-3-carboxylic acid cyclohexylmethyl-amide,
5-(2-Chloro-4-fluoro-phenyl)-1-cyclohexylmethyl-2-methyl-1H-pyrrole-3-carboxylic acid cyclohexylamide,
5-(2-Chloro-5-fluoro-phenyl)-1-cyclohexylmethyl-2-methyl-1H-pyrrole-3-carboxylic acid cyclohexylamide,
Cyclopropylmethyl-2-methyl-5-(3-trifluoromethyl-phenyl)-1H-pyrrole-3-carboxylic acid cyclohexylamide,
Cyclopropylmethyl-5-(2-fluoro-3-trifluoromethyl-phenyl)-2-methyl-1H-pyrrole-3-carboxylic acid cyclohexylamide,
1-(2-Cyclohexyl-ethyl)-5-(5-fluoro-2-methoxy-phenyl)-2-methyl-1H-pyrrole-3-carboxylic acid cyclohexylamide,
5-(2,4-Bis-trifluoromethyl-phenyl)-1-cyclohexylmethyl-2-methyl-1H-pyrrole-3-carboxylic acid cyclohexylamide,
Cyclohexylmethyl-5-(2-fluoro-5-trifluoromethyl-phenyl)-2-methyl-1H-pyrrole-3-carboxylic acid ((1SR, 2RS)-2-hydroxy-cyclohexyl)-amide,
5-(2-Chloro-5-trifluoromethyl-phenyl)-1-cyclohexylmethyl-2-methyl-1H-pyrrole-3-carboxylic acid ((1S,2S)-2-hydroxy-cyclohexyl)-amide,
Cyclohexylmethyl-5-(2-fluoro-5-trifluoromethyl-phenyl)-2-methyl-1H-pyrrole-3-carboxylic acid ((1S,2S)-2-hydroxy-cyclohexyl)-amide,
Cyclohexylmethyl-5-(2-fluoro-5-trifluoromethyl-phenyl)-2-methyl-1H-pyrrole-3-carboxylic acid ((1R,2R)-2-hydroxy-cyclohexyl)-amide,
Cyclohexylmethyl-5-(2,5-dichloro-phenyl)-2-methyl-1H-pyrrole-3-carboxylic acid ((1S,2S)-2-hydroxy-cyclohexyl)-amide,
Cyclohexylmethyl-5-(2,5-dichloro-phenyl)-2-methyl-1H-pyrrole-3-carboxylic acid ((1R,2R)-2-hydroxy-cyclohexyl)-amide,
Cyclohexylmethyl-5-(2,4-dichloro-phenyl)-2-methyl-1H-pyrrole-3-carboxylic acid ((1S,2R)-2-hydroxy-cyclohexyl)-amide,
Cyclohexylmethyl-5-(2,4-dichloro-phenyl)-2-methyl-1H-pyrrole-3-carboxylic acid ((1R,2S)-2-hydroxy-cyclohexyl)-amide,
1-(2-Hydroxy-cyclohexylmethyl)-2-methyl-5-(2-trifluoromethoxy-phenyl)-1H-pyrrole-3-carboxylic acid cyclohexylamide,
Cyclohexylmethyl-5-(2,5-dichloro-phenyl)-2-methyl-1H-pyrrole-3-carboxylic acid ((1SR,2RS)-2-hydroxy-cyclohexyl)-amide,
5-(2-Chloro-5-trifluoromethyl-phenyl)-1-cyclohexylmethyl-2-methyl-1H-pyrrole-3-carboxylic acid ((1SR, 2RS)-2-hydroxy-cyclohexyl)-amide,
1-(2-Cyclopropyl-ethyl)-5-(5-fluoro-2-methoxy-phenyl)-2-methyl-1H-pyrrole-3-carboxylic acid cyclohexylamide,
5-(5-Chloro-2-methoxy-4-methyl-phenyl)-1-(2-cyclopropyl-ethyl)-2-methyl-1H-pyrrole-3-carboxylic acid cyclohexylamide,
and any pharmaceutically acceptable salt thereof.

26. A compound according to claim 1, selected from the group consisting of: 5-(2,5-Bis-trifluoromethyl-phenyl)-1-cyclopropylmethyl-2-methyl-1H-pyrrole-3-carboxylic acid cyclohexylamide,
Cyclopropylmethyl-2-methyl-5-(2-trifluoromethoxy-phenyl)--1H-pyrrole-3-carboxylic acid cyclohexylamide,
Cyclopropylmethyl-2-methyl-5-(2-trifluoromethoxy-phenyl)--1H-pyrrole-3-carboxylic acid ((1RS ,2RS)-2-hydroxy-cyclohexyl)-amide,
5 -(5-Chloro-2-trifluoromethoxy-phenyl)--1-cyclohexylmethyl-2-methyl--1H-pyrrole-3-carboxylic acid cyclohexylamide,
5-(2-Fluoro-5-trifluoromethyl-phenyl)--1-(4-hydroxy-cyclohexylmethyl)-2-methyl--1H-pyrrole-3-carboxylic acid cyclohexylamide,
5-(5-Bromo-2-trifluoromethoxy-phenyl)--1-cyclohexylmethyl-2-methyl--1H-pyrrole-3-carboxylic acid cyclohexylamide,
5-(5-Chloro-2-fluoro-phenyl)-1-cyclopropylmethyl-2-methyl-1H-pyrrole-3-carboxylic acid cyclohexylamide,
5-(2-Fluoro-5-trifluoromethyl-phenyl)-1-(1RS ,2SR)-2-hydroxy-cyclohexylmethyl)-2-methyl-1H-pyrrole-3-carboxylic acid ((1R,2R)-2-hydroxy-cyclohexyl)-amide,
5-(2-Chloro-5-trifluoromethyl-phenyl)-1-cyclopropylmethyl-2-methyl-1H-pyrrole-3-carboxylic acid cyclohexylamide,
5-(2,5-Bis-trifluoromethyl-phenyl)-1-(2,2-dimethyl-cyclopropylmethyl)-2-methyl-1H-pyrrole-3-carboxylic acid cyclohexylamide,
5-(2,5-Bis-trifluoromethyl-phenyl)-1-(2-cyclopropyl-ethyl)-2-methyl-1H-pyrrole-3-carboxylic acid cyclohexylamide, 5-(5-Chloro-2-fluoro-phenyl)-1-((S)-2,2-dimethyl-cyclopropylmethyl)-2-methyl-1H-pyrrole-3-carboxylic acid cyclohexylamide, 5-(5-Chloro-2-fluoro-phenyl)-1-((S)-2,2-dimethyl-cyclopropylmethyl)-2-methyl-1H-pyrrole-3-carboxylic acid ((1R,2R)-2-hydroxy-cyclohexyl)-amide, 5-(2-Chloro-5-trifluoromethyl-phenyl)-1-((1SR,2RS)-2-hydroxy-cyclohexylmethyl)-2-methyl-1H-pyrrole-3-carboxylic acid cyclohexylamide, 5-(5-Chloro-2-methyl-phenyl)-1-cyclohexylmethyl-2-methyl-1H-pyrrole-3-carboxylic acid ((1R,2R)-2-hydroxy-cyclohexyl)-amide, Cyclohexylmethyl-5-(5-fluoro-2-methyl-phenyl)-2-methyl-1H-pyrrole-3-carboxylic acid piperidin-1-ylamide, 5-(5-Chloro-2-methyl-phenyl)-1-cyclohexylmethyl-2-methyl-1H-pyrrole-3-carboxylic acid piperidin-1-ylamide, 5-(4-Chloro-2-methyl-phenyl)-1-cyclohexylmethyl-2-methyl-1H-pyrrole-3-carboxylic acid ((1R,2R)-2-hydroxy-cyclohexyl)-amide, Cyclohexylmethyl-5-(5-fluoro-2-methyl-phenyl)-2-methyl-1H-pyrrole-3-carboxylic acid ((1R,2R)-2-hydroxy-cyclohexyl)-amide, 5-(2-Chloro-5-trifluoromethyl-phenyl)-1-(2-cyclopropyl-ethyl)-2-methyl-1H-pyrrole-3-carboxylic acid ((1R,2R)-2-hydroxy-cyclohexyl)-amide, 5-(2-Chloro-5-trifluoromethyl-phenyl)-1-(2-hydroxy-cyclohexylmethyl)-2-methyl-1H-pyrrole-3-carboxylic acid ((1R,2R)-2-hydroxy-cyclohexyl)-amide, and any pharmaceutically acceptable salt thereof.

* * * * *